US010842871B2

(12) United States Patent
Ferrero et al.

(10) Patent No.: US 10,842,871 B2
(45) Date of Patent: Nov. 24, 2020

(54) METHODS FOR TREATING ALZHEIMER'S DISEASE

(71) Applicant: Biogen International Neuroscience GmbH, Baar (CH)

(72) Inventors: James L. Ferrero, Carlsbad, CA (US); Leslie Lugene Williams, Sherborn, MA (US); Jeffrey Joseph Sevigny, Lexington, MA (US)

(73) Assignee: Biogen International Neuroscience GmbH, Baar (CH)

( * ) Notice: Subject to any disclaimer, the term of this patent is extended or adjusted under 35 U.S.C. 154(b) by 489 days.

(21) Appl. No.: 15/531,960

(22) PCT Filed: Dec. 2, 2015

(86) PCT No.: PCT/IB2015/002465
§ 371 (c)(1),
(2) Date: May 31, 2017

(87) PCT Pub. No.: WO2016/087944
PCT Pub. Date: Jun. 9, 2016

(65) Prior Publication Data
US 2018/0333487 A1 Nov. 22, 2018

Related U.S. Application Data

(60) Provisional application No. 62/086,674, filed on Dec. 2, 2014, provisional application No. 62/111,874, filed
(Continued)

(51) Int. Cl.
*A61K 39/395* (2006.01)
*C07K 16/18* (2006.01)
(Continued)

(52) U.S. Cl.
CPC .......... *A61K 39/3955* (2013.01); *C07K 16/18* (2013.01); *C07K 16/28* (2013.01); *A61K 2039/505* (2013.01); *A61K 2039/545* (2013.01)

(58) Field of Classification Search
CPC .... C07K 16/18; C07K 16/28; C07K 2317/24; C07K 2317/56; C07K 2317/565;
(Continued)

(56) References Cited

U.S. PATENT DOCUMENTS 5,876,950 A   3/1999  Siadak et al.
6,180,370 B1  1/2001  Queen
(Continued)

FOREIGN PATENT DOCUMENTS

EP   1 033 996    9/2000
EP   1 172 378    1/2002
(Continued)

OTHER PUBLICATIONS

Sevigny J et al. The antibody aducanumab reduces Abeta plaques in Alzheimer's disease. Nature, 537, 50-56 (Year: 2016).*
(Continued)

*Primary Examiner* — Kimberly Ballard
(74) *Attorney, Agent, or Firm* — Fish & Richardson P.C.

(57) ABSTRACT

A method for treatment of a human patient for Alzheimer's disease (AD) comprises sequentially administering multiple doses of a recombinant, fully human, anti-amyloid beta monoclonal antibody to the patient. In preferred embodiments, the antibody is administered in increasing amounts over a period of time. In preferred embodiments, the susceptibility of the patient to amyloid related imaging abnormalities (ARIA) is thereby reduced.

63 Claims, 24 Drawing Sheets
Specification includes a Sequence Listing.

Related U.S. Application Data on Feb. 4, 2015, provisional application No. 62/149,133, filed on Apr. 17, 2015, provisional application No. 62/195,119, filed on Jul. 21, 2015.

(51) Int. Cl.
*C07K 16/28* (2006.01)
*A61K 39/00* (2006.01)

(58) Field of Classification Search
CPC .......... C07K 2317/76; A61K 39/3955; A61K 2039/505; A61K 2039/545
See application file for complete search history.

(56) References Cited

U.S. PATENT DOCUMENTS

| | | |
|---|---|---|
| 6,187,309 B1 | 2/2001 | McMichael et al. |
| 6,294,171 B2 | 9/2001 | McMichael |
| 6,436,401 B1 | 8/2002 | McMichael |
| 6,586,656 B2 | 7/2003 | McLonlogue et al. |
| 6,703,015 B1 | 3/2004 | Solomon et al. |
| 6,710,226 B1 | 3/2004 | Schenk |
| 6,713,058 B2 | 3/2004 | McMichael |
| 6,743,427 B1 | 6/2004 | Schenk |
| 6,750,324 B1 | 6/2004 | Schenk et al. |
| 6,761,888 B1 | 7/2004 | Shecnk |
| 6,787,637 B1 | 9/2004 | Schenk |
| 6,913,745 B1 | 7/2005 | Schenk |
| 7,582,733 B2 | 9/2009 | Basi et al. |
| 7,700,751 B2 | 4/2010 | Basi et al. |
| 7,727,957 B2 | 6/2010 | Schenk et al. |
| 7,763,249 B2 | 7/2010 | Suginura et al. |
| 7,893,214 B2 | 2/2011 | Schenk |
| 7,964,192 B1 | 6/2011 | Schenk |
| 8,003,097 B2 | 8/2011 | Schroeter et al. |
| 8,022,268 B2 | 9/2011 | Grimm et al. |
| 8,034,339 B2 | 10/2011 | Schenk |
| 8,106,164 B2 | 1/2012 | Gellerfors et al. |
| 8,128,928 B2 | 3/2012 | Basi et al. |
| 8,173,127 B2 | 5/2012 | Chain |
| 8,263,558 B2 | 9/2012 | Holzman et al. |
| 8,337,848 B2 | 12/2012 | Kidd et al. |
| 8,378,081 B2 | 2/2013 | Matsubara et al. |
| 8,389,226 B2 | 3/2013 | Ray et al. |
| 8,497,246 B2 | 7/2013 | Pardridge et al. |
| 8,753,610 B2 | 6/2014 | Pardridge et al. |
| 8,906,367 B2 | 12/2014 | Nitsch et al. |
| 9,670,272 B2 | 6/2017 | Nitsch et al. |
| 9,828,420 B2 | 11/2017 | Nitsch et al. |
| 10,131,708 B2 | 11/2018 | Nitsch et al. |
| 10,202,445 B2 | 2/2019 | Nitsch et al. |
| 2002/0086847 A1 | 7/2002 | Chain |
| 2003/0028904 A1 | 2/2003 | Gumienny et al. |
| 2003/0232758 A1 | 12/2003 | St. George-Hyslop et al. |
| 2004/0197324 A1 | 10/2004 | Liu et al. |
| 2004/0219146 A1 | 11/2004 | Schenk |
| 2004/0265301 A1 | 12/2004 | Schenk et al. |
| 2005/0009150 A1 | 1/2005 | Basi et al. |
| 2005/0013815 A1 | 1/2005 | Schenk |
| 2005/0048049 A1 | 3/2005 | Schenk |
| 2005/0118651 A1 | 6/2005 | Basi et al. |
| 2005/0249725 A1 | 11/2005 | Schenk et al. |
| 2005/0249727 A1 | 11/2005 | Schenk |
| 2005/0260697 A1 | 11/2005 | Wang et al. |
| 2006/0062859 A1 | 3/2006 | Blum |
| 2006/0165682 A1 | 7/2006 | Basi et al. |
| 2006/0235207 A1 | 10/2006 | Tsuchiya et al. |
| 2006/0240485 A1 | 10/2006 | Hock |
| 2006/0257396 A1 | 11/2006 | Jacobsen |
| 2007/0031416 A1 | 2/2007 | Shoji et al. |
| 2007/0190046 A1 | 8/2007 | DeMaattos et al. |
| 2008/0050367 A1 | 2/2008 | Basi et al. |
| 2008/0281082 A1 | 11/2008 | Basi et al. |
| 2008/0292625 A1 | 11/2008 | Schroeter et al. |
| 2008/0300204 A1 | 12/2008 | Federoff et al. |
| 2009/0035295 A1 | 2/2009 | Hillen et al. |
| 2009/0041771 A1 | 2/2009 | St. George-Hyslop et al. |
| 2009/0069268 A1 | 3/2009 | Shepard et al. |
| 2009/0069544 A1 | 3/2009 | Basi et al. |
| 2009/0104629 A1 | 4/2009 | Fiala |
| 2009/0191190 A1 | 7/2009 | Barghorn et al. |
| 2009/0191231 A1 | 7/2009 | Schenk et al. |
| 2009/0214515 A1 | 8/2009 | Holzman et al. |
| 2009/0238831 A1 | 9/2009 | Hillen et al. |
| 2009/0246145 A1 | 10/2009 | Small |
| 2010/0120787 A1 | 5/2010 | Sutcliffe et al. |
| 2010/0202968 A1 | 8/2010 | Nitsch et al. |
| 2010/0209417 A1 | 8/2010 | Lee et al. |
| 2010/0209422 A1 | 8/2010 | Ravetch et al. |
| 2010/0221187 A1 | 9/2010 | Lieberburg et al. |
| 2010/0239591 A1 | 9/2010 | Kidd et al. |
| 2010/0266596 A1 | 10/2010 | Cox |
| 2010/0279433 A1 | 11/2010 | Holtzman et al. |
| 2010/0297108 A1 | 11/2010 | Henco et al. |
| 2011/0044985 A1 | 2/2011 | Rosenthal et al. |
| 2011/0052498 A1 | 3/2011 | Lannfelt et al. |
| 2011/0059092 A1 | 3/2011 | Vannechelen et al. |
| 2011/0044986 A1 | 4/2011 | Biere-Citron et al. |
| 2011/0135660 A1 | 6/2011 | Schenk et al. |
| 2011/0152341 A1 | 6/2011 | Schilling et al. |
| 2011/0182809 A1 | 7/2011 | Nitsch et al. |
| 2011/0200609 A1 | 8/2011 | Glabe et al. |
| 2011/0212109 A1 | 9/2011 | Barghorn et al. |
| 2011/0229413 A1 | 9/2011 | Lieberburg et al. |
| 2011/0237537 A1 | 9/2011 | Lombard et al. |
| 2011/0287005 A1 | 11/2011 | Hillen et al. |
| 2011/0306756 A1 | 12/2011 | Schenk |
| 2012/0027755 A1 | 2/2012 | Lannfelt et al. |
| 2012/0082667 A1 | 4/2012 | Yokoseki et al. |
| 2012/0156193 A1 | 6/2012 | Yokoseki et al. |
| 2012/0177664 A1 | 7/2012 | Yokoseki et al. |
| 2013/0164367 A1 | 6/2013 | Oddo et al. |
| 2013/0216555 A1 | 8/2013 | Nitsch et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2014/0272950 A1 | 9/2014 | Wang et al. |
| 2014/0274764 A1 | 9/2014 | Zhu et al. |
| 2014/0323424 A1 | 10/2014 | Lombard et al. |
| 2015/0147343 A1 | 5/2015 | Nitsch et al. |
| 2015/0315267 A1 | 11/2015 | Bussiere et al. |
| 2016/0177390 A1 | 6/2016 | Feng et al. |
| 2016/0289310 A1 | 10/2016 | Nitsch et al. |
| 2017/0283491 A1 | 10/2017 | Nitsch et al. |
| 2018/0134773 A1 | 5/2018 | Nitsch et al. |
| 2019/0079077 A1 | 3/2019 | Co et al. |
| 2019/0263896 A1 | 8/2019 | Nitsch et al. |

FOREIGN PATENT DOCUMENTS

| | | |
|---|---|---|
| EP | 1 185 296 | 3/2002 |
| EP | 1 185 298 | 3/2002 |
| EP | 1 212 088 | 6/2002 |
| EP | 1 358 213 | 11/2003 |
| EP | 1 613 347 | 1/2006 |
| EP | 1 679 080 | 7/2006 |
| EP | 1 690 547 | 8/2006 |
| EP | 1 720 909 | 11/2006 |
| EP | 1 741 783 | 1/2007 |
| EP | 1 766 396 | 3/2007 |
| EP | 1 861 422 | 5/2007 |
| EP | 1 994 937 | 11/2008 |
| EP | 2 045 267 | 4/2009 |
| EP | 2 108 376 | 10/2009 |
| EP | 2 204 381 | 7/2010 |
| EP | 2 210 901 | 7/2010 |
| EP | 2 305 282 | 4/2011 |
| EP | 2 305 709 | 4/2011 |
| EP | 2 361 629 | 8/2011 |
| EP | 2 364 719 | 9/2011 |
| JP | 2003-509020 | 3/2003 |
| JP | 2006-265189 | 10/2006 |
| JP | 2007-536895 | 12/2007 |
| JP | 2008-524247 | 7/2008 |

(56) References Cited

FOREIGN PATENT DOCUMENTS

| | | |
|---|---|---|
| JP | 2008-309778 | 12/2008 |
| JP | 2009-519708 | 5/2009 |
| SG | 177954 | 2/2012 |
| WO | WO 1993/014125 | 7/1993 |
| WO | WO 1999/050300 | 10/1999 |
| WO | WO 2001/018169 | 3/2001 |
| WO | WO 2001/031056 | 5/2001 |
| WO | WO 2001/098361 | 12/2001 |
| WO | WO 2003/069332 | 8/2003 |
| WO | WO 2003/074081 | 9/2003 |
| WO | WO 2003/077858 | 9/2003 |
| WO | WO 2004/032868 | 4/2004 |
| WO | WO 2004/095031 | 11/2004 |
| WO | WO 2004/108895 | 12/2004 |
| WO | WO 2005/018424 | 3/2005 |
| WO | WO 2005/025616 | 3/2005 |
| WO | WO 2005/047860 | 5/2005 |
| WO | WO 2005/060641 | 7/2005 |
| WO | WO 2005/123775 | 12/2005 |
| WO | WO 2006/020581 | 2/2006 |
| WO | WO 2006/050041 | 5/2006 |
| WO | WO 2006/066171 | 6/2006 |
| WO | WO 2006/103116 | 10/2006 |
| WO | WO 2006/116192 | 11/2006 |
| WO | WO 2006/118959 | 11/2006 |
| WO | WO 2007/011907 | 1/2007 |
| WO | WO 2007/012061 | 1/2007 |
| WO | WO 2007/021255 | 2/2007 |
| WO | WO 2007/068412 | 6/2007 |
| WO | WO-2007067959 A2 * 6/2007 ......... C07K 16/2818 |
| WO | WO 2008/081008 | 7/2008 |
| WO | WO 2008/086395 | 7/2008 |
| WO | WO 2008/103472 | 8/2008 |
| WO | WO 2008/110372 | 9/2008 |
| WO | WO 2008/131298 | 10/2008 |
| WO | WO 2008/148884 | 12/2008 |
| WO | WO 2009/033743 | 3/2009 |
| WO | WO 2009/040134 | 4/2009 |
| WO | WO 2009/094592 | 7/2009 |
| WO | WO 2010/004434 | 1/2010 |
| WO | WO 2010/032059 | 3/2010 |
| WO | WO 2010/069603 | 6/2010 |
| WO | WO 2011/064225 | 6/2011 |
| WO | WO 2011/072091 | 6/2011 |
| WO | WO 2012/005838 | 1/2012 |
| WO | WO 2012/021469 | 2/2012 |
| WO | WO 2012/049570 | 4/2012 |
| WO | WO 2012/080518 | 6/2012 |
| WO | WO 2012/174262 | 12/2012 |
| WO | WO 2013/020723 | 2/2013 |
| WO | WO 2013/061163 | 5/2013 |
| WO | WO 2013/140349 | 9/2013 |
| WO | WO 2014/041069 | 3/2014 |
| WO | WO 2014/089500 | 6/2014 |
| WO | WO 2014/182631 | 11/2014 |
| WO | WO 2015/092077 | 6/2015 |
| WO | WO 2015/120233 | 8/2015 |
| WO | WO 2015/175769 | 11/2015 |
| WO | WO 2015/191825 | 12/2015 |
| WO | WO 2016/016278 | 2/2016 |
| WO | WO 2016/087944 | 6/2016 |

OTHER PUBLICATIONS

Blennow K et al. Fluid biomarkers in Alzheimer disease. Cold Spring Harbor Perspect. Med. 2, a006221, 23 pages. (Year: 2012).*
History of Changes for Study NCT01677572, Multiple dose study of BIIB037 in subjects with prodromal or mild Alzheimer's disease. Sep. 12, 2013. (Year: 2013).*
Shen LZ et al. Design and analysis of dose escalation studies to mitigate dose-limiting adverse effects. Drug Information Journal, 40, 69-78. (Year: 2006).*
"Aducanumab" [online]. Alzforum, by Biomedical Research Forum, LLC, first available online Jan. 29, 2014, [Retrieved on Mar. 3, 2016], Retrieved from the Internet: URL www.alzforum.org/therapeutics/aducanumab>, 6 pages.
"Biogen Antibody Buoyed by Phase 1 Data and Hungry Investors" [online] Alzforum, by Biomedical Research Forum, LLC, first available online Mar. 25, 2015, [Retrieved on Jun. 12, 2015], 9 pages.
"Human-Derived SOD1 Antibodies Show Promise in ALS Mice," [online] Alzforum, by Biomedical Research Forum, LLC, first available online Apr. 17, 2013, [Retrieved on Jul. 28, 2014], Retrieved from the Internet: URL www.alzforum.org/news/conference-coverage/human-derived-sod1-antibodies-show-promis-als-mice> 1 pages.
"Multiple Dose Study of BIIB037 in Subjects With Prodromal or Mild Alzheimer's Disease," [online] ClinicalTrials.gov, U.S. National Library of Medicine, first available online Aug. 30, 2012, [Retrieved on Jul. 28, 2014], Retrieved from the Internet: URL clinicaltrials.gov/ct2/show/study/NCT01677572> 1 page.
"The advantages of using recombinant antibodies," [online] Absolute Antibody, [Retrieved on Jun. 28, 2016], Retrieved from the Internet: URL absoluteantibody.com/about-us/advantages-of-recombinant-antibodies/>, 1 page.
"The Dictionary of Immunology," Academic Press, Fourth Edition, Harcourt Brace & Company, (1995), 3 pages.
Abcam, "Anti-pan Synuclein antibody (ab6176)," Abeam Inc., United States, available online on or before Jun. 26, 2012, Retrieved from the Internet: URL www.abcam.com/pan-synuclein-antibody-ab6176.html>, 2 pages.
Adderson et al., "Molecular Analysis of Polyreactive Monoclonal Antibodies from Rheumatic Carditis: Human Anti-N-Acetylglucosamine/Anti-Myosin Antibody V Region Genes," J Immunol, 161:2020-2031, Aug. 15, 1998, 13 pages.
Alloul et al., "Alzheimer's disease: a review of the disease, its epidemiology and economic impact," Arch Gerontol Geriatr, 27:198-221, Nov. 2, 1998, 33 pages.
Andreasen et al., "First Administration of the Fc-Attenuated Anti-[beta] Amyloid Antibody GSK933776 to Patients with Mild Alzheimer's Disease: A Randomized, Placebo-Controlled Study," PLOS One 10(3):e0098153 (2015).
Baba et al., "Aggregation of a-Synuclein in Lewy Bodies of Sporadic Parkinson's Disease and Dementia with Lewy Bodies," Am J Pathol 152(4):879-884, Apr. 1998, 6 pages.
Bard et al., "Epitope and isotype specificities of antibodies to β-amyloid peptide for protection against Alzheimer's disease-like neuropathology," PNAS 100(4):2023-2028, Feb. 2003, 6 pages.
Bard et al., "Peripherally administered antibodies against amyloid β-peptide enter the central nervous system and reduce pathology in a mouse model of Alzheimer disease," Nat Med 6(8):916-919, Aug. 2000, 4 pages.
Basi et al., "Structural Correlates of Antibodies Associated with Acute Reversal of Amyloid 13-related Behavioral Deficits in a Mouse Model of Alzheimer Disease," J Biol Chem, 285(5):3417-3427, Jan. 2010, 12 pages.
Bayer and Wirths, "Intraneuronal Aβ as a trigger for neuron loss: Can this be translated into human pathology?" Biochem Soc Trans, 39(4):857-861, Jan. 1, 2011, 5 pages.
BD Transduction Laboratories, "Technical Data Sheet: Purified Mouse Anti-a-Synuclein," BD Biosciences, available online on or before Jun. 27, 2012, [Retrieved on Mar. 3, 2016], Retrieved from the Internet: URL www.bdbiosciences.com/ds/pm/tds/610787.pdf>, 2 pages.
Becker et al., "Stimulation of endogenous neurogenesis by anti-EFRH immunization in a transgenic mouse model of Alzheimer's disease," Proc. Natl. Acad. Sci. USA 104(5):1691-1696, Jan. 2007, 6 pages.
Bernasconi et al., "Maintenance of Serological Memory by Polyclonal Activation of Human Memory B Cells," Science 298:2199-2202, Dec. 2002, 3 pages.
Biscaro et al., "Aβ immunotherapy Protects Morphology and Survival of Adult-Born Neurons in Doubly Transgenic APP/PS1 Mice," J Neurosci 29(45): 14108-14119, Nov. 2009, 12 pages.
Bohrmann et al., "Gantenerumab: A Novel Human Anti-A13 Antibody Demonstrates Sustained Cerebral Amyloid-13 Binding and

(56) References Cited

OTHER PUBLICATIONS

Elicits Cell-Mediated Removal of Human Amyloid-β," J Alzheimer's Dis, 28(1):49-69, 2012, 21 pages.
BusinessWire [online], "Biogen Presents New Data from Phase 1B Study of Investigational Alzheimer's Disease Treatment Aducanumab (BIIB037) at Alzheimer's Association International Conference® 2015," Jul. 22, 2015, [Retrieved on Mar. 3, 2016], Retrieved from the Internet: URL www.businesswire.com/news/home/20150722005352/en/Biogen-Presents-Data-Phase-1B-Study-Investigational>, 5 pages.
Buttini et al., "β-Amyloid Immunotherapy Presents Synaptic Degeneration in a Mouse Model of Alzheimer's Disease," J Neurosci 25:9096-9101, Oct. 2005, 6 pages.
Buxbaum, "The systemic amyloidoses," Current Opinion in Rheumatology, 16:67-75 (2004).
Buxbaum et al. "Molecular dissection of NRG1-ERBB4 signaling implicates PTPRZ1 as a potential schizophrenia susceptibility gene," Mol. Psychiatry 2008;13:162-172.
Campbell, "β-amyloid: friend or foe," Med Hypot, 56(3):388-391, Mar. 2001, 4 pages.
Casset et al., "A peptide mimetic of an anti-CD4 monoclonal antibody by rational design," Biochem and Biophys Res Comm 307:198-205, Jul. 2003, 8 pages.
Chen et al., "Selection and Analysis of an Optimized Ant-VEGF Antibody: Crystal Structure of an Affinity-matured Fab in Complex with Antigen," J Mol Biol 293:965-881, Nov. 1999, 17 pages.
Choi et al. "Fine epitope mapping of monoclonal antibodies specific to human alpha-synuclein," Neuroscience Letters, 397(1-2):53-58, Apr. 2006, 6 pages.
Cohn, "Introduction to Surrogate Markers," Circulation, 109[suppll IV]: IV-20-IV-21 (2004).
Das et al. "Amyloid-β Immunization Effectively Reduces Amyloid Deposition in FcRy Knock-Out Mice," J Neurosci, 23(24):8532-8538, Sep. 2003, 7 pages.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084, Sep. 2002, 9 pages.
DeMattos et al., "Peripheral anti-Aβ antibody alters CNS and plasma Aβ clearance and decreases brain Aβ burden in a mouse model of Alzheimer's disease," Proc Natl Acad Sci USA, 98:8850-8855, Jul. 2001, 6 pages.
Department of Health and Human Services, Food and Drug Administration, Memorandum of Meeting Minutes with Biogen Idec, with cover letter and signature page By Director Russell G. Katz, dated Nov. 19, 2009; received Dec. 2, 2009, 9 pages.
Du et al., "Human anti-β-amyloid antibodies block β-amyloid fibril formation and prevent β-amyloid-induced neurotoxicity," Brain 126:1935-1939, Sep. 2003, 5 pages.
Dunn et al., "The Immunobiology of Cancer Immunosurveillance and Immunoediting," Immunity 21:137-1498, Aug. 2004, 12 pages.
Dunstan et al., "The role of brain macrophages on the clearance of amyloid plaques following the treatment of Tc2576 with BIIB037," Alzheimer's & Dementia: The Journal of the Alzheimer's Association, 7(4):S700, Jul. 2011, 3 pages.
El-Agnaf et al., "a-Synuclein implicated in Parkinson's disease is present in extracellular biological fluids, including human plasma," FASEB J., 17( 13): 1945-1947, Oct. 2003, 3 pages.
El-Agnaf et al., "Detection of oligomeric forms of a-synuclein protein in human plasma as a potential biomarker for Parkinson's disease," FASEB J., 20:419-425, 2006, 7 pages.
Emadi et al "Inhibiting Aggregation of a-Synuclein with Human Single Chain Antibody Fragments," Biochem, 43(10):2871-2878, Mar. 2004, 10 pages.
Emadi et al., "Isolation of a human single chain antibody fragment against oligomeric a-synuclein that inhibits aggregation and prevents a-synuclein-induced toxicity" J. Mol Biol, 368(4):1132-1144, May 2007, 13 pages.
Email from Edward Stuart, CEO of Neurimmune Therapeutics AG, to Leslie Coney, Biogen IDEC, dated Nov. 1, 2007, 1 page.
Email from Jan Grimm of Neurimmune, to Ken Rhodes of Biogen IDEC, dated Oct. 13, 2009, 1 page.
Emmanouilidou et al., "Assessment of a-Synuclein Secretion in Mouse and Human Brain Parenchyma," PLoS One, 6(6):e22225, doi: 10.1371/journal.pone.0022225, Jul. 2011, 9 pages.
Esposito et al., "Neuronal Differentiation in the Adult Hippocampus Recapitulates Embryonic Development," J. Neurosci. 25(44):10074-10086, Nov. 2005, 13 pages.
European Office Action in European Application No. 09786187.6, dated Nov. 11, 2016, 8 pages.
European Search Report and Written Opinion in European Application No. 11185486, dated Mar. 7, 2012, 11 pages.
European Search Report and Written Opinion in European Application No. 12802721, dated Feb. 2, 2015, 16 pages.
Extended Search Report and Written Opinion in European Application No. 12846452, dated May 21, 2015, 4 pages.
European Search Report in European Application No. 17169749.3, dated Aug. 1, 2017, 14 pages.
Ge et al., "GABA regulates synaptic integration of newly generated neurons in the adult brain," Nature 439(2):589-593, Jul. 2006, 10 pages.
Gelfanova et al., "Quantitative analysis of amyloid-beta peptides in cerebrospinal fluid using immunoprecipitation and MALDI-Tof mass spectrometry," Briefings in Functional Genomics and Proteomics, 6(2):149-158, Jun. 1, 2007, 10 pages.
George et al., "a-Synuclein transgenic mice exhibit reduced anxiety-like behavior," Exp Neural, 210:788-792, Apr. 2008, 5 pages.
George, "The Synucleins," Genome Biol, 3(1):reviews 3002.1-3002.6, Dec. 2001, 6 pages.
Geylis and Steinitz, "Immunotherapy of Alzheimer's disease (AD): From murine models to anti-amyloid beta (Aβ) human monoclonal antibodies," Autoimmunity Reviews 5:33-39, Jan. 2006, 7 pages.
Geylis et al., "Human monoclonal antibodies against amyloid-beta from healthy adults," Neurobiol of Aging, 26:597-606, May 2005, 10 pages.
Giasson et al., "A Panel of Epitope-Specific Antibodies Detects Protein Domains Distributed Throughout Human a-Synuclein in Lewy Bodies of Parkinson's Disease," J Neurosci Res, 59:528-533, 2000, 6 pages.
Giasson et al., "Neuronal a-Synucleinopathy with Severe Movement Disorder in Mice Expressing A53T Human a-Synuclein," Neuron, 34:521-533, May 2002, 13 pages.
Giraudon et al., "Semaphorin CD100 from Activated T Lymphocytes Induces Process Extension Collapse in Oligodendrocytes and Death of Immature Neural Cells," J lmmunol, 172:1246-1255, Jan. 2004, 11 pages.
Gupta et al., "A Novel human-derived antibody against NY-ESO-1 improves the efficacy of chemotherapy," Cancer Immunity, 13:1-9 (Jan. 2013).
Haass et al., "Amyloid β-peptide is produced by cultured cells during normal metabolism," Nature, 359:322-325, Sep. 1992, 4 pages.
Hantman and Perl, "Molecular and Genetic Features of a Labeled Class of Spinal Substantia Gelatinosa Neurons in a Transgenic Mouse," J Comp Neurol, 492:90-100, Wiley-Liss, Inc., 2005, 11 pages.
Hasan Mohajeri et al., "Passive immunization against beta-amyloid peptide protects central nervous system (CNS) neurons from increased vulnerability associated with an Alzheimer's disease-causing mutation," Journal of Biological Chemistry, American Society for Biochemistry and Molecular Biology U.S., 277(36):33012-33017 (Sep. 2002).
Hashimoto et al., "A novel approach for Aβ1-40 quantification using immuno-PCR," J Neurosci Meth, 205(2):364-367, Jan. 25, 2012, 4 pages.
Ho et al., "In vivo imaging of adult human hippocampal neurogenesis: progress, pitfalls and promise," Mol Psychiatry, 18(4):404-416, Nature Publishing Group, Feb. 2013, 14 pages.
Hock and Nitsch, "Clinical Observations with AN-1792 Using TAPIR Analyses," Neurodeg Dis 2:273-276, 2005, 4 pages.
Hock et al., "Antibodies against β-Amyloid Slow Cognitive Decline in Alzheimer's Disease," Neuron, 38(4):547-554, May 2003, 8 pages.

(56) References Cited

OTHER PUBLICATIONS

Hock et al., "Generation of antibodies specific for β-amyloid by vaccination of patients with Alzheimer disease," Nat Med, 8(11):1270-1275, 2002, 6 pages.
Holcomb et al., "Accelerated Alzheimer-type phenotype in transgenic mice carrying both mutant amyloid precursor protein and presenilin I transgenes," Nat. Med. 4(1):97-100, Nature Publishing Group, Jan. 1998, 4 pages.
Holm et al., "Functional mapping and single chain construction of the anti-cytokeratin 8 monoclonal antibody TS1," Mol Immunol 44:1075-1084, 2007, 10 pages.
Hsiao et al., "Correlative Memory Deficits, Aβ Elevation, and Amyloid Plaques in Transgenic Mice," Science 274(5284):99-102, American Associate for the Advancement of Science, Oct. 1996, 4 pages.
Hyman et al., "Autoantibodies to Amyloid-β and Alzheimer's Disease," Ann Neurol 49:808-810, 2001, 5 pages.
International Preliminary Report on Patentability and Written Opinion in International Application No. PCT/EP2008/000053, dated Jul. 7, 2009, 10 pages.
International Preliminary Report on Patentability and Written Opinion in International Application No. PCT/IB2009/006666, dated Jan. 11, 2011, 10 pages.
International Preliminary Report on Patentability and Written Opinion in International Application No. PCT/US2013/073700, dated Jun. 9, 2015, 10 pages.
International Preliminary Report on Patentability and Written Opinion in International Application No. PCT/US2014/045994, dated Jan. 12, 2016, 15 pages.
International Search Report and Written Opinion in International Application No. PCT/US2012/062430, dated Jan. 24, 2013, 10 pages.
International Search Report and Written Opinion in International Application No. PCT/EP2009/009186, dated Mar. 12, 2010, 11 pages.
International Search Report and Written Opinion in International Application No. PCT/IB2009/006666, dated Feb. 22, 2010, 16 pages.
International Search Report and Written Opinion in International Application No. PCT/IB2015/002465, dated Jun. 9, 2016, 18 pages.
International Search Report and Written Opinion in International Application No. PCT/US2012/043701, dated Sep. 26, 2012, 11 pages.
International Search Report and Written Opinion in International Application No. PCT/US2013/073700, dated Mar. 3, 2014, 13 pages.
International Search Report and Written Opinion in International Application No. PCT/US2014/045994, dated Nov. 3, 2014, 19 pages.
International Search Report and Written Opinion in International Application No. PCT/US2015/030753, dated Aug. 27, 2015, 11 pages.
International Search Report and Written Opinion in International Application No. PCT/US2015/035282, dated Sep. 29, 2015, 18 pages.
Invitrogen Corp, "Mouse anti-a-Synuclein: For In Vitro Diagnostic Use," Product information, revision date Aug. 2008, accessed on Jul. 2, 2012, 3 pages.
Iwai et al., "Non-Aβ Component of Alzheimer's Disease Amyloid (NAG) Is Amyloidogenic," Biochemistry, 34:10139-10145, 1995, 8 pages.
Jakes et al., "Epitope mapping of LB509, a monoclonal antibody directed against human a-synuclein," Neurosci Lett, 269:13-16, 1999, 4 pages.
Janus et al., "Aβ peptide immunization reduces behavioral impairment and plaques in a model of Alzheimer's disease," Nature 408:979-982, Dec. 2000, 4 pages.
Janus et al., "Spatial learning in transgenic mice expressing human presenilin 1 (PS1) transgenes," Neurobiol Aging, 21(4):541-549, 2000, 9 pages.
Jawhar et al., "Pyroglutamate amyloid-β (Aβ): a hatchet man in Alzheimer disease," J Biol Chem, 286(45):38825-38832, Nov. 11, 2011, 9 pages.
Jensen et al., "Residues in the synuclein consensus motif of the a-synuclein fragment, NAG, participate in transglutaminase-catalysed cross-linking to Alzheimer-disease amyloid 13A4 peptide," Biochem J, 310:91-94, Aug. 1995, 4 pages.
Jin et al., "Vascular endothelial growth factor (VEGF) stimulates neurogenesis in vitro and in vivo," Proc Natl Acad Sci USA 99(18): 11946-11950, National Academy of Sciences, Sep. 2002, 5 pages.
Kadir et al., "Positron emission tomography imaging and clinical progression in relation to molecular pathology in the first Pittsburgh Compound B positron emission tomography patient with Alzheimer's disease," Brain, 134(1):301-317, Jan. 1, 2011, 17 pages.
Kahle et al., "Selective Insolubility of a-Synuclein in Human Lewy Body Diseases Is Recapitulated in a Transgenic Mouse Model," Am J Pathol, 159(6):2215-2225, Dec. 2001, 11 pages.
Kahle et al., "Subcellular Localization of Wild-Type and Parkinson's Disease-Associated Mutant a-Synuclein in Human and Transgenic Mouse Brain," J Neurosci, 20(17):6365-6373, Sep. 2000, 9 pages.
Kastanenka et al., "Amelioration of calcium dyshomeostasis by immunotherapy with BIIB037 in Tg2576 mice," Alzheimer's & Dementia: The Journal of the Alzheimer's Association, 9(4):P508, Jul. 2013.
Kawarabayashi et al., "Age-Dependent Changes in Brain, CSF, and Plasma Amyloid 13 Protein in the Tg2576 Transgenic Mouse Model of Alzheimer's Disease," J Neurosci, 21 (2):372-381, Jan. 2001, 10 pages.
Knobloch et al., "Intracellular Aβ and cognitive deficits precede β-amyloid deposition in transgenic arcAβ mice," Neurobiol Aging 28(9):1297-1306, Sep. 2007, 10 pages.
Kohler and Milstein, "Continuous cultures of fused cells secreting antibody of predefined specificity," Nature 256:495-497, 1975, 5 pages.
Kumanogoh et al., "Requirement for the Lymphocyte Semaphorin, CD100, in the Induction of Antigen-Specific T Cells and the Maturation of Dendritic Cells," J lmmunol, 169:1175-1181, Aug. 2002, 7 pages.
Larrick et al., "Recombinant antibodies," Hum Antibod Hybridoma, 2:172-189 (1991), abstract.
Laske et al., "Higher BDNF serum levels predict slower cognitive decline in Alzheimer's disease patients," International Journal of Neuropsychopharmacology, 14(3):399-404 (Apr. 2011).
Laurén et al., "Cellular prion protein mediates impairment of synaptic plasticity by amyloid-beta oligomers," Nature 457: 1128-1132, Macmillan Publishers Limited, 2009, 13 pages.
Lee et al., "Enzyme-linked immunosorbent assays for alpha-synuclein with species and multimeric state specificities," J Neurosci Meth, 199(2):249-257, 2011, 9 pages.
Lee et al., "Stereological analysis of microvascular parameters in a double transgenic model of Alzheimer's disease," Brain Res Bull 65(4) :3 17-322, Elsevier Science, 2005, 6 pages.
Lee et al., "Targeting Amloid-beta Peptide (Abeta) Oligomers by Passive Immunization with a Conformation-selective Monoclonal Antibody Improves Learning and Memory in abeta Precursor Protein (APP) Transgenic Mice," Journal of Biological Chemistry, American Society for Biochemistry and Molecular Biology, 281(7):4292-4299, Feb. 2006.
Lehman et al., "Amino acid sequence of the variable region of a human chain: Location of a possible JH segment," Proc Natl Acad Sci USA, 77(6):3239-3243, Jun. 1980, 5 pages.
Lim et al., "APOE and BDNF polymorphisms moderate amyloid β-related cognitive decline in preclinical Alzheimer's disease," Mol Psychi, 1-7, Oct. 7, 2014, 7 pages.
Lim et al., "BDNF Val66Met, Ab amyloid, and cognitive decline in preclinical Alzheimer's disease," Neurobiol of Aging, 34(11):2457-2464, Jun. 13, 2013, 8 pages.
Lim et al., "Effect of BDNF Val66Met on Memory Decline and Hippocampal Atrophy in Prodromal Alzheimer's Disease: A Preliminary Study," PLoS One, 9(1):1-5, Jan. 27, 2014, 5 pages.

(56) References Cited

OTHER PUBLICATIONS

Lippa et al., "Antibodies to a-Synuclein Detect Lewy Bodies in Many Down's Syndrome Brains with Alzheimer's Disease," Ann Neural, 45(3):353-357, Mar. 1999, 7 pages.
Liu et al., "Amyloid β peptide alters intracellular vesicle trafficking and cholesterol homeostasis," Proc Natl Acad Sci USA, 95:13266-13271, Oct. 1998, 6 pages.
Lobello et al., "Targeting Beta Amyloid: A Clinical Review of Immunotherapeutic Approaches in Alzheimer's Disease," International Journal of Alzheimer's Disease 6(4):S305-14 (2012).
Lopez-Toledano and Shelanksi, "Neurogenic Effect of β-Amyloid Peptide in the Development of Neural Stem Cells," J Neurosci, 24:5439-5444, Jun. 2004, 6 pages.
Lewczuk et al., "Amyloid β peptides in cerebrospinal fluid as profiled with surface enhanced laser desorption/ionization time-of-flight mass spectrometry: evidence of novel biomarkers in Alzheimer's disease," Biol Psych, 55(5):524-530, Mar. 1, 2004, 7 pages.
Lu et al., "BDNF-based synaptic repair as a disease-modifying strategy for neurodegenerative diseases," Nature Reviews Neuroscience, 14:401-416 (May 2013).
Lynch et al., "An ScFv Intrabody Against the Non-Amyloid Component of Alpha Synuclein Reduces Intracellular Aggregation and Toxicity," NIH Public Access Author Manuscript; final publication in J. Mol Biol. 377(1):136-147, Mar. 2008, 17 pages.
MacCallum et al., "Antibody-antigen Interactions: Contact Analysis and Binding Site Topography," J Mol Biol 262:732-745, 1996, 14 pages.
Maguire-Zeiss et al., "Identification of human alpha-synuclein specific single chain antibodies," Biochem Biophys Res Commun, 349(4):1198-1205, 2006, 25 pages.
Masliah et al., "Dopaminergic loss and inclusion body formation in alpha-synuclein mice: implications for neurodegenerative disorders," Science, 287(5456):1265-1269, Feb. 2000, 5 pages.
Masliah et al., "Effects of a-Synuclein Immunization in a Mouse Model of Parkinson's Disease," Neuron, 46:857-868, 2005, 12 pages.
Masters et al., "Amyloid plaque core protein in Alzheimer disease and Down syndrome," Proc Natl Acad Sci USA 82:4245-4249, Jun. 1985, 5 pages.
Masuda et al., "Inhibition of a-synuclein fibril assembly by small molecules: Analysis using epitopespecific antibodies," FEBS Lett, 583(4):787-791, Feb. 2009, 5 pages.
Mcheyzer-Williams and Ahmed, "B cell memory and the long-lived plasma cell," Curr Opin Immunol, 11:172-179, Apr. 1999, 10 pages.
McLaurin et al., "Therapeutically effective antibodies against amyloid-13 peptide target amyloid-β residues 4-10 and inhibit cytotoxicity and fibrillogenesis," Nat Med, 8: 1263-1269, Oct. 2002, 7 pages.
Miller and Messer, "Intrabody Applications in Neurological Disorders: Progress and Future Prospects," Molecular Therapy, 12(3):394-401, Sep. 2005, 8 pages.
Mollenhauer et al., "Direct quantification of CSF a-synuclein by ELISA and first cross-sectional study in patients with neurodegeneration," Exp Neural, 213(2):315-325, Oct. 2008, 11 pages.
Mollenhauer et al., "Quantification of alpha-synuclein in cerebrospinal fluid as a biomarker candidate: review of the literature and considerations for future studies," Biomarkers in Medicine, 4(5):683-699, 2010, 17 pages.
Moreth et al., "Passive anti-amyloid immunotherapy in Alzheimer's disease: What are the most promising targets?," Immunity and Ageing, Biomed Central, London, GB, 10(1):18, May 2013.
Morgan et al., "Aβ peptide vaccination prevents memory loss in an animal model of Alzheimer's disease," Nature, 408:982-985, Dec. 2000, 13 pages.
Mougenot et al., "Production of a monoclonal antibody, against human a-synuclein, in a subpopulation of C57BL/6J mice, presenting a deletion of the a-synuclein locus," J Neurosci Meth, 192(2):268-276, 2010, 9 pages.
Mruthinti et al., "Autoimmunity in Alzheimer's disease: increased levels of circulating IgGs binding Aβ and RAGE peptides," Neurobiol Aging, 25:1023-1032, 2004, 10 pages.

Mueggler et al., "Compromised Hemodynamic Response in Amyloid Precursor Protein Transgenic Mice," J Neurosci, 22:7218-7224, Aug. 2002, 7 pages.
Muller et al., "TransMabs: cell penetrating antibodies, the next generation," Expert Opin Biol Ther, 5(2):237-241, Apr. 2005, 5 pages.
GenBank Accession No. S56746, GI No. 1362748, "alpha-synuclein, NAC—human (fragment)," dated Jul. 17, 2007, 1 page.
GenBank Accession No. P37640.1, GI No. 586067, "RecName: Full=Alpha-synuclein; AltName: Full=Non-A beta component of AD amyloid; AltName: Full=Non-A4 component of amyloid precursor; Short=NACP," dated Jun. 15, 2012, 11 pages.
Neff et al., "Immunotherapy and naturally occurring autoantibodies in neurodegenerative disorders," Autoimmunity Reviews, 7:501-507, Jun. 2008, 7 pages.
O'Nuallain et al., "Conformational Abs recognizing a generic amyloid fibril epitope," Proceedings National Academy of Sciences, 99(3):1485-1490, Feb. 2002.
Orgogozo et al., "Subacute meningoencephalitis in a subset of patients with AD after Aβ 42 immunization," Neurology, 61 (1):46-54, Jul. 2003, 11 pages.
Padlan et al., "Structure of an antibody-antigen complex: Crystal structure of the HyHEL-10 Fab-lysozyme complex," Proc Natl Acad Sci USA, 86(15):5938-5942, Aug. 1989, 5 pages.
Palop et al., "Aberrant Excitatory Neuronal Activity and Compensatory Remodeling of Inhibitory Hippocampal Circuits in Mouse Models of Alzheimer's Disease," Neuron 55(5):697-711, Cell Press, Sep. 2007, 15 pages.
Papachroni et al., "Autoantibodies to alpha-synuclein in inherited Parkinson's disease," J Neurochem, 101:749-756, May 2007, 8 pages.
Patrias et al., "Specific antibodies to soluble alpha-synuclein conformations in intravenous immunoglobulin preparations," Clin. Exp. Immunol., 161:527-535, Sep. 2010, 9 pages.
Paul, Editor, Fundamental Immunology, Third Edition, Raven Press, New York, pp. 292-295, 1993, 6 pages.
Perrin et al., "Epitope mapping and specificity of the anti-a-synuclein monoclonal antibody Syn-1 in mouse brain and cultured cell lines," Neurosci. Lett., 349(2):133-135, 2003, 3 pages.
Peters and Kaiserman-Abramof, "The Small Pyramidal Neuron of the Rat Cerebral Cortex. The Perikaryon, Dendrites and Spines," Am J Anat, 127:321-356, 1970, 35 pages.
Pfeifer et al., "Cerebral Hemorrhage After Passive Anti-Aβ Immunotherapy," Science, 298:1379, 2002, 3 pages.
Piantadosi et al., "Abstracts from the Program of the Second Annual Meeting of the American Society for Experimental Neurotherapeutics, Washington, DC, Mar. 23-25, 2000." American Society for Experimental Neurotherapeutics Abstracts, Arch Neurol., 57:1233-1239 (2000).
Plant et al., "The production of amyloid beta peptide is a critical requirement for the viability of central neurons," J Neurosci, 23(13):5531-5535, Society for Neuroscience, Jul. 2003, 5 pages.
Plümpe et al., "Variability of doublecortin-associated dendrite maturation in adult hippocampal neurogenesis is independent of the regulation of precursor cell proliferation," BMC Neurosci, 7:77, Nov. 2006, 14 pages.
Portelius et al., "Characterization of Amyloid β Peptides in Cerebrospinal Fluid by an Automated Immunoprecipitation Procedure Followed by Mass Spectrometry," J Proteome Res, 6(11):4433-4439, Nov. 1, 2007, 7 pages.
Portelius et al., "Determination of β-Amyloid Peptide Signatures in Cerebrospinal Fluid Using Immunoprecipitation-Mass Spectrometry," J Proteome Res, 5(4):1535-3893, Apr. 1, 2006, 7 pages.
Priller et al., "Synapse Formation and Function Is Modulated by the Amyloid Precursor Protein," J Neurosci, 26(27):7212-7221, Jul. 2006, 10 pages.
Qui et al., "Small antibody mimetics comprising two complementarity-determining regions and a framework region for tumor targeting," Nature Biotech 25:921-929, Aug. 2007, 9 pages.
Racke et al., "Exacerbation of Cerebral Amyloid Angiopathy-Associated Microhemorrhage in Amyloid Precursor Protein Trans-

(56) References Cited

OTHER PUBLICATIONS genic Mice by Immunotherapy is Dependent on Antibody Recognition of Deposited Forms of Amyloid β," J Neurosci 25:629-636, Jan. 2005, 8 pages.
Robert et al., "Engineered antibody intervention strategies for Alzheimer's disease and related dementias by targeting amyloid and toxic oligomers" Protein Eng Des Sel, 22(3):199-208, 2009, 10 pages.
Rudikoff et al., "Single amino acid substitution altering antigen-binding specificity," Proc Natl Acad Sci, 79:1979-1983, Mar. 1982, 5 pages.
Ruszczycki et al., "Sampling issues in quantitative analysis of dendritic spines morphology," BMC Bioinformatics, 13:213, 2012, 12 pages.
Ryu and Chen, "Development of Alzheimer's disease imaging agents for clinical studies," Front Biosci, 13:777-789, Jan. 2008, 13 pages.
Schenk et al., "Amyloid-β immunotherapy for Alzheimer's disease: the end of the beginning," Nat Rev Neurosci, 3(10):824-828, Oct. 2002, 6 pages.
Schenk et al., "Immunization with amyloid-beta attenuates Alzheimer-disease-like pathology in the PDAPP mouse," Nature, 400:173-177, Jul. 1999, 5 pages.
Seitz et al., "Isolation und Charakterisierung eines physiologisch vorkommenden Autoantikorpers gegen humanes alpha-Synuclein," 35:S86, Abstract P528, Sep. 2008, 6 pages.
Serrano-Pozo et al., "Neuropathological Alterations in Alzheimer Disease," Cold Spring Harb. Perspect. Med., 1 :a006189, 23 pages, 2011, 23 pages.
Sevigny, et al., "Randomized double-blind, placebo-controlled, phase 1b study of aducanumab (BIIB037), an anit-ab monoclonal antibody, in patients with prodromal or mild Alzheimer's disease; interim results by disease stage and ApoE4 status," Neurology 85(4):E44 (2015).
Shankar et al., "Natural oligomers of the Alzheimer amyloid-beta protein induce reversible synapse loss by modulating an NMDA-type glutamate receptor-dependent signaling pathway," J Neurosci, 27(11):2866-2875, Mar. 2007, 10 pages.
Shi et al., "The Class IV Semaphorin CD100 Plays Non redundant Roles in the Immune System: Defective Band T Cell Activation in CD100-Deficient Mice," Immunity, 13:633-642, Nov. 2000, 10 pages.
Sierra et al., "Adult human neurogenesis: from microscopy to magnetic resonance imaging," Front Neurosci, 5(47):1-18, Apr. 2011, 18 pages.
Sigma-Aldrich, Inc., "Monoclonal Anti-a-Synuclein. Clone Syn211. Purified mouse immunoglobulin. Product No. S 5566," Product Information, updated Jan. 2003, accessed on Mar. 3, 2016, 2 pages.
Sigmund, C., "Viewpoint: Are studies in genetically altered mice out of control?" Arterioscler. Thromb. Vasc. Biology 20:1425-1429 (2000).
Simpson et al., "Antibodies to normal and Alzheimer human brain structures from non-immunized mice of various ages," FEBS Letters 217:62-64, Jun. 1987, 3 pages.
Simpson et al., "Autoantibodies to Alzheimer and Normal Brain Structures from Virus-Transformed Lymphocytes," J Neuroimmunol, 13:1-8, 1986, 4 pages.
Skovronsky et al., "Neurodegenerative Diseases: New Concepts of Pathogenesis and Their Therapeutic Implications," Annu. Rev. Pathol. Mech. Disease, 1:151-170 (2006).
SNP Cluster Report: rs6946211, [accessed: Apr. 19, 2017], retrieved from the internet: URL <www.ncbi.nlm.nih.gov/SNP/snp_ref.cgi?rs=6946211&pt=1V7XNyo5DVBB_0NHALSkRXG4eofetRo6uOUrVB6VklwEM4a5d>, 3 pages.
Sorra and Harris, "Overview on the Structure, Composition, Function, Development and Plasticity of Hippocampal Dendritic Spines," Hippocampus 10:501-511, 2000, 11 pages.
Supplementary European Search Report in European Application No. 13860755, dated Sep. 20, 2016, 13 pages.
Supplementary European Search Report in European Application No. 14822788, dated Dec. 16, 2016, 8 pages.
Thakker et al., "lntracerebroventricular amyloid-β antibodies reduce cerebral amyloid angiopathy and associated micro-hemorrhages in aged Tg2576 mice" Proc Natl Acad Sci USA, 106(11):4501-4506, Mar. 2009, 6 pages.
Traggiai et al., "An efficient method to make human monoclonal antibodies from memory B cells: potent neutralization of SARS coronavirus," Nat Med, 10:871-875, Aug. 2004, 5 pages.
Turner et al., "Roles of amyloid precursor protein and its fragments in regulating neural activity, plasticity and memory," Prog Neurobiol 70(1):1-32, 2003, 32 pages.
Ueda et al., "Molecular cloning of cDNA encoding an unrecognized component of amyloid in Alzheimer's disease," Proc Natl Acad Sci, 90:11282-11286, Dec. 1993, 5 pages.
United States Office Action in U.S. Appl. No. 12/522,031, dated Dec. 10, 2012, 20 pages.
United States Office Action Summary in U.S. Appl. No. 12/522,031, dated May 23, 2012, 10 pages.
United States Office Action in U.S. Appl. No. 12/522,031, dated Jun. 26, 2013, 6 pages.
United States Office Action in U.S. Appl. No. 13/003,245, dated Apr. 23, 2013, 13 pages.
United States Office Action in U.S. Appl. No. 13/003,245, dated Aug. 28, 2012, 33 pages.
U.S. Appl. No. 09/724,319, filed Nov. 27, 2012, 111 pages.
Vajdos et al., "Comprehensive Functional Maps of the Antigen-binding Site of an Anti-ErbB2 Antibody Obtained with Shotgun Scanning Mutagenesis," J Mol Biol 320:415-428, 2002, 14 pages.
Van Der Putten et al., "Neuropathology in Mice Expressing Human a-Synuclein," J Neurosci, 20(16):6021-6029, Aug. 2000, 9 pages.
Van Praag et al., "Functional neurogenesis in the adult hippocampus," Nature 415:1030-1034, Feb. 2002, 5 pages.
Wall, RJ, "Transgenic livestock: Progress and prospects for the future," Theriogenology 45:57-68 (1996).
Wang et al., "A subpopulation of precursor cells in the mouse dentate gyrus receives synaptic GABAergic input," Mol Cell Neurosci, 29:181-189, Jun. 2005, 9 pages.
Wang et al., "Clearance of amyloid-beta in Alzheimer's disease: progress, problems and perspectives," Drug Disc. Today, 11 (19-20):931-938, Oct. 2006, 9 pages.
Wang et al., "Functional soluble CD1 OO/Sema4D released from activated lymphocytes: possible role in normal and pathologic immune responses," Blood, 97(11 ):3498-3504, Jun. 2001, 7 pages.
Watanabe et al., "Enhanced Immune Responses in Transgenic Mice Expressing a Truncated Form of the Lymphocyte Semaphorin CD100," J lmmunol, 167(8):4321-4328, Oct. 2001, 9 pages.
Waxman and Giasson, "Characterization of antibodies that selectively detect a-synuclein in pathological inclusions," Acta Neuropathol, 116(1):37-46, Jul. 2008, 17 pages.
Weksler et al., "Patients with Alzheimer disease have lower levels of serum anti-amyloid peptide antibodies than healthy elderly individuals," Experimental Gerontology, 37:43-948, 2002, 8 pages.
Wilcock et al., "Amyloid-β vaccination, but Not Nitro-Nonsteroidal Anti-Inflammatory Drug Treatment, Increases Vascular Amyloid and Microhemorrhage While Both Reduce Parenchymal Amyloid," Neuroscience 144:950-960, Feb. 2007, 11 pages.
Wilcock et al., "Intracranially Administered Anti-A13 Antibodies Reduce β-Amyloid Deposition by Mechanisms Both Independent of and Associated with Microglial Activation," J Neurosci, 23(9):3745-3751, May 2003, 7 pages.
Wilcock et al., "Passive immunotherapy against Aβ in aged APP=transgenic mice reverses cognitive deficits and depletes parenchymal amyloid deposits in spite of increased vascular amyloid and microhemorrhate," J Neuroinfmallation, 1:24, Dec. 8, 2004, 11 pages.
Wilcock et al., "Quantification of cerebral amyloid angiopathy and parenchymal amyloid plaques with Congo red histochemical stain," Nat Protoc 1(3):1591-1595, 2006, 5 pages.
Wittnam et al., "Pyroglutamate amyloid β (Aβ) aggravates behavioral deficits in transgenic amyloid mouse model for Alzheimer disease," J Biol Chem, 287(11):8154-8162, Mar. 9, 2012, 15 pages.

(56) References Cited

OTHER PUBLICATIONS

Woulfe et al., "Absence of elevated anti-a-synuclein and anti-EBV latent membrane protein antibodies in PD," Neurology, 58: 1435-1436, May 2002, 4 pages.
Wu et al., "Humanization of a Murine Monoclonal Antibody by Simultaneous Optimization of Framework and CDR Residues," J Mol Biol 294:151-162, 1999, 12 pages.
Zhang et al., "Semi-quantitative analysis of a-synuclein in subcellular pools of rat brain neurons: An immunogold electron microscopic study using a C-terminal specific monoclonal antibody," Brain Res, 1244:40-52, 2008, 13 pages.
Zhao et al., "Distinct Morphological Stages of Dentate Granule Neuron Maturation in the Adult Mouse Hippocampus," J Neurosci. 26(1):3-11, Society for Neuroscience, Jan. 2006, 9 pages.
Zlokovic "The Blood-Brain Barrier in Health and Chronic Neurodegenerative Disorders," Neuron 57: 178-201, 2008, 24 pages.
"Biogen plans regulatory filing for aducanumab in Alzheimer's disease based on new analysis of larger dataset from phase 3 studies", Biogen News Release, Oct. 22, 2019, 12 pages.
"Biogen and Eisai to discontinue phase 3 engage and emerge trials of aducanumab in Alzheimer's disease", Biogen News Release, Mar. 21, 2019, 8 pages.
ClinicalTrials.gov [online], "221AD301 Phase 3 Study of Aducanumab (BIIB037) in Early Alzheimer's Disease (ENGAGE)," Last updated Apr. 24, 2019, [Retrieved on May 19, 2019], 6 pages.
DiFrancesco et al., "Anti-Aβ autoantibodies in amyloid related imaging abnormalities (ARIA): candidate biomarker for immunotherapy in Alzheimer's disease and cerebral amyloid angiopathy," Frontiers in Neurology, 2015, 6:1-6.
European Extended Search Report in European Application No. 14822788.7, dated Dec. 15, 2016, 8 pages.
Ferrero et al., "First-in-human, double-blind, placebo-controlled, single-dose escalation study of aducanumab (BIIB037) in mild-to-moderate Alzheimer's disease," Alzheimer's & Dementia: Translational Research & Clinical Interventions, 2016, 2(3):169-176.
Gregory et al., "What is the dominant Aβ species in human brain tissue? A review," Neurotoxicity research, 2005, 7(1-2):29-41.
Hampel et al., "Biological markers of amyloid β-related mechanisms in Alzheimer's disease," Experimental neurology, 2010, 223(2):334-346.
Hock, "Biochemical Aspects of Dementias," Dialogues in Clinical Neuroscience, 2003, 5(1):27-33.
International Preliminary Report on Patentability and Written Opinion in International Application No. PCT/EP2017/056031, dated Sep. 18, 2018, 8 pages.
International Preliminary Report on Patentability and Written Opinion in International Application No. PCT/IB2015/002465, dated Jun. 6, 2017, 9 pages.
International Preliminary Report on Patentability and Written Opinion in International Application No. PCT/US2015/030753, dated Nov. 15, 2016, 7 pages.
International Preliminary Report on Patentability and Written Opinion in International Application No. PCT/US2015/035282, dated Dec. 15, 2016, 12 pages.
International Preliminary Report on Patentability and Written Opinion in International Application No. PCT/EP2017/063711, dated Dec. 11, 2018, 14 pages.
International Search Report and Written Opinion in International Application No. PCT/EP2017/056031, dated May 10, 2017, 11 pages.
International Search Report and Written Opinion in International Application No. PCT/EP2017/063711, dated Oct. 23, 2017, 21 pages.
International Search Report and Written Opinion in International Application No. PCT/US2018/047508, dated Oct. 20, 2018, 17 pages.
Knowles et al., "The p75 neurotrophin receptor promotes amyloid-β (1-42)-induced neuritic dystrophy in vitro and in vivo," Journal of Neuroscience, 2009, 29(34):10627-10637.
Lai et al., "A First-In-Human Study of Ban2401, A Novel Monoclonal, Antibody Against Beta-Amyloid Protofibrils", Oral Sessions: 04-05: Therapeutics: Clinical Trials III, Jul. 2013, 9(4):P689.
Meyer-Luehmann et al., "A reporter of local dendritic translocation shows plaque-related loss of neural system function in APP-transgenic mice," Journal of Neuroscience, 2009, 29(40):12636-12640.
Morar-Mitrica et al., "Development of a stable low-dose aglycosylated antibody formulation to minimize protein loss during intravenous administration," MAbs, 2015, 7(4):792-803.
Novak et al., "Efficacy and Safety of Monthly Subcutaneous Bapineuzumab", Alzheimer's and Dementia, Jul. 2014, 10(4):P25, Abstract IC-P-041.
Piazza et al., "Amyloid-Related Imaging Abnormalities (ARIA) in Immunotherapy Trials for Alzheimer's Disease: Need for Prognostic Biomarkers?," Journal of Alzheimer's Disease, 2016, 52(2):417-420.
Selkoe, "Alzheimer's Disease," Cold Spring Harbor Perspectives in Biology, 2011, 3(7):a004457.
Sevigny et al., "Aducanumab (BIIB037), an anti-amyloid beta monoclonal antibody, in patients with prodromal or mild Alzheimer's disease: Interim results of a randomized, double-blind, placebo-controlled, phase 1b study," Alzheimer's & Dementia: The Journal of the Alzheimer's Association, 2015, 11(7):277, 1 page.
Sevigney et al., "A Single Ascending Dose Study of BIIB037 in People with Mild to Moderate Alzheimer's Disease", Alzheimer's and Dementia, Jul. 2013, 9(4):P290, Abstract P1-359.
Van Muiswinkel et al., "The amino-terminus of the amyloid-β protein is critical for the cellular binding and consequent activation of the respiratory burst of human macrophages," Journal of Neuroimmunology, 1999, 96(1):121-130.
Webster et al., "Antibody-mediated phagocytosis of the amyloid β-peptide in microglia is differentially modulated by C1q," The Journal of Immunology, 2001, 166(12):7496-7503.
Zago et al., "Vascular alterations in PDAPP mice after anti-Aβ immunotherapy: Implications for amyloid-related imaging abnormalities," Alzheimer's & Dementia, 2013, 9(5):S105-S115.
U.S. Appl. No. 12/522,031, filed Mar. 10, 2010, Nitsch et al.
U.S. Appl. No. 13/827,673, filed Mar. 14, 2013, Nitsch et al.
U.S. Appl. No. 13/838,526, filed Mar. 15, 2013, Nitsch et al.
U.S. Appl. No. 13/841,485, filed Mar. 15, 2013, Nitsch et al.
U.S. Appl. No. 14/322,096, filed Jul. 2, 2014, Nitsch et al.
U.S. Appl. No. 15/066,304, filed Mar. 10, 2016, Nitsch et al.
U.S. Appl. No. 15/791,632, filed Oct. 24, 2017, Nitsch et al.
U.S. Appl. No. 16/154,920, filed Oct. 9, 2018, Nitsch et al.
U.S. Appl. No. 13/003,245, filed Apr. 4, 2011, Nitsch et al.
U.S. Appl. No. 14/650,200, filed Jun. 5, 2015, Bussiere.
U.S. Appl. No. 14/904,388, filed Jan. 11, 2016, Feng.
U.S. Appl. No. 16/307,364, filed Dec. 5, 2018, Boot.
Sperling et al., "Amyloid related abnormalities in patients with Alzheimer's disease treated with bapineuzumab: a retrospective analysis", The Lancet Neurology, 2012, 11(3):241-249.
Sperling et al., "Amyloid related imaging abnormalities (ARIA) in amyloid modifying therapeutic trials: recommendations from the Alzheimer's association research roundtable workgroup", Alzheimer's & Dementia, Jul. 2011, 7(4):367-385.

\* cited by examiner

| | 1 mg/kg DB ONLY | 3 mg/kg DB ONLY | 3 mg/kg DB + LTE | 1 mg/kg → 3 mg/kg LTE | 3-6 mg/kg TITRATION LTE | 6 mg/kg* DB | 10 mg/kg DB |
|---|---|---|---|---|---|---|---|
| TOTAL ARIA | 1/31 (3%) | 2/32 (6%) | 5/42 (12%) | 2/17 (12%) | 1/11 (9%) | 10/30 (33%) | 13/32 (41%) |
| ApoE4 CARRIERS** | 1/19 (5%) | 1/21 (5%) | 3/25 (12%) | 2/11 (18%) | 1/7 (14%) | 9/21 (43%) | 11/20 (55%) |
| ApoE4 NON-CARRIERS | 0/12 (0%) | 1/11 (9%) | 2/17 (12%) | 0/6 (0%) | 0/4 (0%) | 1/9 (11%) | 2/11 (17%) |
| TOTAL SYMPTOMATIC ARIA | 1/1 (100%) | 0/2 (0%) | 2/5 (40%) | 1/2 (50%) | 1/1 (100%) | 4/10 (40%) | 4/13 (31%) |
| CARRIERS | 1 | 0 | 1 | 1 | 1 | 3 | 3 |
| NON-CARRIERS | 0 | 0 | 1 | 0 | 0 | 1 | 1 |

ESTIMATED INCIDENCE OF ARIA-E AND/OR ARIA-H IN Ph1b STUDY

FIG. 4

| ENDPOINTS | |
|---|---|
| PRIMARY<br>• SAFETY AND TOLERABILITY<br>SECONDARY<br>• SERUM PK<br>• ANTI-ADUCANUMAB ANTIBODIES<br>• AMYLOID PET, CHANGE FROM BASELINE TO WEEK 26 | EXPLORATORY<br>• CDR-sb, MMSE<br>• AMYLOID PET, CHANGE FROM BASELINE TO WEEK 54 | EXPLORATORY - ONGOING<br>• NTB, FCSRT, NPI-Q<br>• FLUID BIOMARKERS<br>• VOLUMETRIC MRI<br>• FDG-PET<br>• rs-fMRI<br>• ASL-MRI |

ASL-MRI = ARTERIAL SPIN LABELING MAGNETIC RESONANCE IMAGING; CDR-sb = CLINICAL DEMENTIA RATING SUM OF BOXES; FCSRT = FREE AND CUED SELECTIVE REMINDING TEST; FDG-PET = 18F-FLUORODEOXYGLUCOSE POSITRON EMISSION TOMOGRAPHY; MMSE = MINI-MENTAL STATE EXAMINATION; NPI-Q = NEUROPSYCHIATRIC INVENTORY-QUESTIONNAIRE; NTB = NEUROPSYCHOLOGICAL TEST BATTERY; PK = PHARMACOKINETIC; PET = POSITRON EMISSION TOMOGRAPHY; rs-fMRI = RESTING STATE FUNCTIONAL MAGNETIC RESONANCE IMAGING

*FIG. 15*

| BASELINE DEMOGRAPHIC AND DISEASE CHARACTERISTICS | | | | | |
|---|---|---|---|---|---|
| | | ADUCANUMAB | | | |
| | PLACEBO (n=40) | 1 mg/kg (n=31) | 3 mg/kg (n=32) | 6 mg/kg (n=30) | 10 mg/kg (n=32) |
| AGE YEARS, MEAN ± SD | 72.8 ± 7.2 | 72.6 ± 7.8 | 70.5 ± 8.2 | 73.3 ± 9.3 | 73.7 ± 08.3 |
| FEMALES, n (%) | 23 (58) | 13 (42) | 17 (53) | 15 (50) | 15 (47) |
| RACE, n (%) WHITE | 40 (100) | 31 (100) | 31 (97) | 28 (93) | 30 (94) |
| WEIGHT (kg), MEAN ± SD | 70.2 ± 15.1 | 73.0 ± 11.9 | 73.0 ± 16.7 | 73.3 ± 15.4 | 75.4 ± 18.1 |
| APoE ε4, n (%) | | | | | |
|   CARRIERS | 26 (65) | 19 (61) | 21 (66) | 21 (70) | 20 (63) |
|   NON-CARRIERS | 14 (35) | 12 (39) | 11 (34) | 9 (30) | 12 (38) |
| CLINICAL STAGE, n (%) | | | | | |
|   PRODROMAL | 19 (48) | 10 (32) | 14 (44) | 12 (40) | 13 (41) |
|   MILD | 21 (53) | 21 (68) | 18 (56) | 18 (60) | 19 (59) |
| MMS, MEAN ± SD | 24.7 ± 3.6 | 23.6 ± 3.3 | 23.2 ± 4.2 | 24.4 ± 2.9 | 24.8 ± 3.1 |
| GLOBAL CDR, n (%) | | | | | |
|   0.5 | 34 (85) | 22 (71) | 22 (69) | 25 (83) | 24 (75) |
|   1 | 6 (15) | 9 (29) | 10 (31) | 5 (17) | 8 (25) |
| CDR-sb, MEAN ± SD | 2.66 ± 1.50 | 3.40 ± 1.76 | 3.50 ± 2.06 | 3.32 ± 1.54 | 3.14 ± 1.71 |
| PET SUVR, MEAN COMPOSITE ± SD | 1.441 ± 0.173 | 1.441 ± 0.146 | 1.464 ± 0.149 | 1.429 ± 0.199 | 1.441 ± 0.192 |
| AD MEDICATIONS USE,[a] n (%) | 24 (60) | 19 (61) | 28 (88) | 20 (67) | 17 (53) |

AD = ALZHEIMER'S DISEASE; CDR = CLINICAL DEMENTIA RATING; CDR-sb = CLINICAL DEMENTIA RATING SUM OF BOXES; MMSE = MINI-MENTAL STATE EXAMINATION; PET = POSITRON EMISSION TOMOGRAPHY; SD = STANDARD DEVIATION; SUVR = STANDARD UPTAKE VALUE RATIO
[a]CHOLINESTRASE INHIBITORS AND/OR MEMANTINE.

*FIG. 18*

| SUMMARY OF ARIAa FINDINGS AND PATIENT DISPOSITION FOLLOWING ARIA-E | | | | | | |
|---|---|---|---|---|---|---|
| | PLACEBO | ADUCANUMAB | | | | |
| | | 1 mg/kg | 3 mg/kg | 6 mg/kg | 10 mg/kg | |
| PATIENT WITH ≥1 POST-BASELINE MRI | 38 | 31 | 32 | 30 | 32 | |
| ISOLATED ARIA-H, n/N (%) | 2/38 (5) | 2/31 (6) | 3/32 (9) | 0/30 | 2/32 (6) | |
| ARIA-E, n/N (%) | 0/38 | 1/31 (3) | 2/32 (6) | 10/30 (33) | 13/32 (41) | |
| BY ApoE ε4 | | | | | | |
| ApoE ε4 CARRIER | 0/24 | 1/19 (5) | 1/21 (5) | 9/21 (43) | 11/20 (55) | |
| ApoE ε4 NON-CARRIER | 0/14 | 0/12 | 1/11 (9) | 1/9 (11) | 2/12 (17) | |
| BY BASELINE CLINICAL STAGE | | | | | | |
| PRODROMAL | 0/18 | 0/10 | 2/12 (14) | 3/12 (25) | 5/13 (38) | |
| ApoE ε4 CARRIER | 0/10 | 0/7 | 1/11 (9) | 2/8 (25) | 4/8 (50) | |
| ApoE ε4 NON-CARRIER | 0/8 | 0/3 | 1/3 (33) | 1/4 (25) | 1/5 (20) | |
| MILD | 0/20 | 1/21 (5) | 0/18 | 7/18 (39) | 8/19 (42) | |
| ApoE ε4 CARRIER | 0/14 | 1/12 (8) | 0/10 | 7/13 (54) | 7/12 (58) | |
| ApoE ε4 NON-CARRIER | 0/6 | 0/9 | 0/8 | 0/5 | 1/7 (14) | |

AD = ALZHEIMER'S DISEASE; ARIA (-E) (-H) = AMYLOID-RELATED IMAGING ABNORMALITIES (-EDEMA) (-MICROHEMORRHAGE/HEMOSIDEROSIS)
aARIA BASED ON NEURIIMMUNE MRI.
bONE PATIENT WITHDREW CONSENT BUT WAS ELIGIBLE TO CONTINUE DOSING.

FIG. 19

METHODS FOR TREATING ALZHEIMER'S DISEASE

CROSS-REFERENCE TO RELATED APPLICATIONS

This application is the National Stage of International Application No. PCT/IB2015/002465, filed on Dec. 2, 2015, which claims the benefit of U.S. Provisional Application No. 62/086,674, filed on Dec. 2, 2014; U.S. Provisional Application No. 62/111,874, filed on Feb. 4, 2015; U.S. Provisional Application No. 62/149,133, filed on Apr. 17, 2015; and U.S. Provisional Application No. 62/195,119, filed on Jul. 21, 2015. The entire contents of each of these prior applications is incorporated herein by reference in their entirety.

Alzheimer's disease (AD) is a progressive neurodegenerative disorder clinically characterized by cognitive impairment, behavioral disturbances, psychiatric symptoms, and disability in activities of daily living. These clinical manifestations constitute AD dementia.

AD International estimates that the number of people living with dementia worldwide will increase from the current value of 35.6 million to 115.4 million by 2050 [Alzheimer's Disease International]. Being the most common cause of dementia, AD accounts for 60 to 80% of dementia cases. In the United States, it is estimated that 5.3 million Americans suffer from dementia caused by AD, and that by 2050 the prevalence will double or triple unless an effective treatment is found [Alzheimer's Association 2010].

Clinical research criteria for dementia due to AD have been recently updated and conforming with the current concept of the disease, a diagnostic framework was developed to embrace pre-dementia stages of AD (e.g., prodromal AD) [Dubois 2010; Sperling 2011]. The main neuropathological hallmarks of the disease are (i) extracellular senile (neuritic) plaques containing aggregated β-amyloid (Aβ) peptides and (ii) intraneuronal neurofibrillary tangles (NFTs) composed of abnormal hyperphosphorylated Tau protein. Although the pathogenesis of these plaques and tangles and how they contribute to the clinical syndrome remain to be fully elucidated, the leading hypothesis—the "amyloid cascade"—proposes that the driving force behind the disease process is the accumulation of Aβ resulting from an imbalance between Aβ production and Aβ clearance in the brain [Hardy and Selkoe 2002].

Aβ is a peptide generated from the metabolism of amyloid precursor protein. Several Aβ peptide alloforms exist (e.g., Aβ40, Aβ42). These monomeric peptides have a variable tendency to aggregate into higher order dimers and oligomers. Through a process of fibrillogenesis, soluble oligomers may transition into insoluble deposits having a β pleated sheet structure. These deposits are also referred to as amyloid plaques and hence are composed of predominantly fibrillar amyloid [Hampel et al. 2010; Gregory and Halliday 2005]. Both soluble and fibrillar forms of Aβ appear to contribute to the disease process [Meyer-Luehmann 2009; Hock 2003; Selkoe 2011].

Biomarker [Jack 2010], clinicopathologic [Delacourte 2002], and cohort [Amieva 2008] studies suggest that the disease process commences 10 to 20 years before the clinical onset of symptoms, and some of the early pathological findings include the deposition of neocortical neuritic plaques and mesial temporal NFTs followed years later by neocortical NFTs [Nelson et al. 2009].

There are currently no therapies that modify the course of Alzheimer's disease. Currently approved therapies provide only modest symptomatic benefit and do not attenuate the course of the disease [Birks 2006; McShane 2006]. Several potential disease-modifying drug candidates are currently under investigation. These candidates include small molecules and immunotherapy (active and passive) that target the Aβ pathway and aim to provide therapeutic benefit by reducing either soluble or insoluble forms of Aβ in the brain and cerebrospinal fluid (CSF).

In response to guidance issued by the U.S. Food and Drug Administration (FDA) to various sponsors on the conduct of clinical trials of amyloid-modifying agents for the treatment of AD, the Alzheimer's Association Research Roundtable convened a Workgroup in July 2010. The Workgroup was composed of academic and industry representatives identified on the basis of their expertise and interest in this area. It was tasked with the objective of providing expert advice regarding the FDA's concerns related to MRI abnormalities, including signal changes thought to represent vasogenic edema (VE) and microhemorrhages (mH). MRI signal changes were first observed in trials of a monoclonal antibody against amyloid β [Black 2010; Salloway 2009; Sperling 2009], and have since been associated with other amyloid-modifying therapies.

While the exact pathophysiologic mechanisms of these MRI abnormalities have not been determined, VE and mH are typically detected on different MRI sequences. They appear to represent a spectrum of image abnormalities which may share some common underlying pathophysiological mechanism, both in the natural history of AD and in the setting of amyloid-modifying therapeutic approaches. The Workgroup suggested referring to this spectrum as Amyloid Related Imaging Abnormalities (ARIA).

Despite the likelihood of shared underlying mechanisms, there may be instances in which it is useful to describe specific phenomena. Thus, the Workgroup further refined the terminology: ARIA-E refers to the MRI signal alterations thought to represent VE and related extravasated fluid phenomena. ARIA-H refers to the MRI signal alterations attributable to mH and hemosiderosis.

ARIA-E most commonly manifests as increased MRI signal intensity on FLAIR or other T2-weighted sequences in the parenchyma and/or leptomeninges in the parietal, occipital, and frontal lobes, but has also been observed in the cerebellum and brainstem [Sperling 2009]. The presence of Apolipoprotein E ε4 allele, ApoE ε4, has been found to be a significant risk factor for the development of ARIA-E.

There are currently very limited publicly available data regarding the clinical course associated with ARIA-E occurring in the setting of clinical trials of amyloid modifying therapies. The Workgroup reviewed the data from bapineuzumab trials, but it noted that it was unknown whether ARIA seen in other amyloid-modifying therapies will have similar clinical course. In any event, the pathophysiological mechanisms underlying vasogenic edema remain to be elucidated.

mH are generally attributed to one of two etiologies: small vessel angiopathy and cerebral amyloid angiopathy (CAA). The prevalence of mH is significantly increased in elderly individuals with cardiovascular risk factors and/or evidence of a previous cerebrovascular event [Goos 2010]. In AD, mH and superficial siderosis are attributed to leakage of blood from CAA vessels [Nakata-Kudo 2006]. CAA is believed to weaken the vessel wall, increasing the risk of micro leaks of blood into adjacent brain, forming mH. Moreover, there are limited publicly available data on incident mH in the setting of ARIA-E associated with amyloid-modifying therapies.

Preliminary reports of ARIA occurrence in therapeutic strategies aimed at decreasing production of specific A-β peptides suggest that decreasing A-β1-42 or altering the ratio of various A-β species might change the dynamics of amyloid production and clearance, resulting in ARIA. It is possible that direct removal of amyloid from the vessel wall would be associated with compromise in the vascular integrity. Alternatively, there may be amyloid related endothelial cell dysfunction resulting in increased vascular permeability, which might explain the similarity to increased permeability. It is also possible that there is a focal inflammatory component that would result in both ARIA-E and ARIA-H, as suggested by the pathology reports from patients with CAA. Normal CSF has also been reported in inflammatory CAA, and it is possible that focal amyloid-related vascular inflammation may play a role in some cases of ARIA. It also remains unknown whether different forms of immunotherapy or specific antibodies are more or less likely to be associated with ARIA [Siemers 2008].

The incidence of ARIA in patients undergoing treatment for Alzheimer's disease continues to be a persistent problem. While there are a number of potential mechanisms of action to target, solutions to the problem have not been found.

Thus, there is a need in the art for methods to reduce the incidence of ARIA in susceptible Alzheimer's disease patients during AD treatment protocols. In some embodiments, the methods are effective in treating AD patients without screening the patients to exclude those with ARIA risk factors, such as ApoE4 carriers. In other embodiments, the methods are for use in treating ApoE4 carriers. In still other embodiments, the methods are for use in treating ApoE4 non-carriers. In preferred embodiments, the methods are particularly adapted for the treatment of patients using immunotherapeutic approaches for lowering Aβ associated with AD, and especially treatments involving the use of anti-amyloid beta monoclonal antibodies in AD patients.

This invention aids in fulfilling these needs in the art by providing a method for treatment of a human patient for Alzheimer's disease (AD). The method comprises sequentially administering multiple doses of a recombinant, fully human, anti-amyloid beta monoclonal antibody. In preferred embodiments, the antibody is administered to the patient in increasing amounts over a period of time.

In one embodiment of the invention, multiple doses of 1 mg/kg of body weight of the patient are administered to the patient at periodic intervals.

In another embodiment of the invention, multiple doses of 3 mg/kg of body weight of the patient are administered to the patient at periodic intervals, optionally with or without the prior administration of the 1 mg/kg doses.

In a further embodiment of the invention, after the administration of the 1 mg/kg doses and/or after the administration of the 3 mg/kg doses, multiple doses of 6 mg/kg of body weight of the patient are administered to the patient at periodic intervals.

In another embodiment of the invention, after the administration of the 1 mg/kg doses and/or after the administration of the 3 mg/kg doses, and/or after the administration of the 6 mg/kg doses, multiple doses of 10 mg/kg of body weight of the patient are administered to the patient at periodic intervals.

In a preferred embodiment of the invention, the dosing protocol is selected based on the ApoE4 status of the patient being treated.

In another preferred embodiment of the invention, each of the intervals is about 4 weeks.

In a typical treatment method according to the invention, 1-5 doses of 1 mg/kg of body weight of the patient are administered at periodic intervals to the patient; this is followed by the administration of 1-5 doses of 3 mg/kg of body weight of the patient at periodic intervals to the patient; and then 6 mg/kg of body weight of the patient are administered to the patient at periodic intervals until the termination of treatment.

In preferred embodiments, the methods of the invention reduce cerebral amyloid burden. In further preferred embodiments, the methods of the invention reduce the susceptibility of the patient to ARIA.

BRIEF DESCRIPTION OF THE DRAWINGS

FIG. 4 reports the estimated incidence of ARIA-E and/or ARIA-H in a study of AD subjects treated with antibody BIIB037.

FIG. 7A shows mean composite SUVR over time for PD analysis population. The dashed line indicates the SUVR cut-point for florbetapir. FIGS. 7B-7F show adjusted mean (±SE) change from baseline in composite SUVR at 26 and 54 weeks among (FIG. 7B) the overall PD analysis population, (FIG. 7C) ApoE ε4 carriers, (FIG. 7D) non-carriers, and patients with (FIG. 7E) prodromal, and (FIG. 7F) mild AD.

FIG. 15 depicts primary and secondary endpoints for the PRIME study.

FIG. 18 depicts baseline demographic and disease characteristics for the PRIME study.

FIG. 19 provides a summary of ARIA findings and patient disposition following ARIA-E.

DESCRIPTION OF EMBODIMENTS

Alzheimer's Disease

Figure 1:
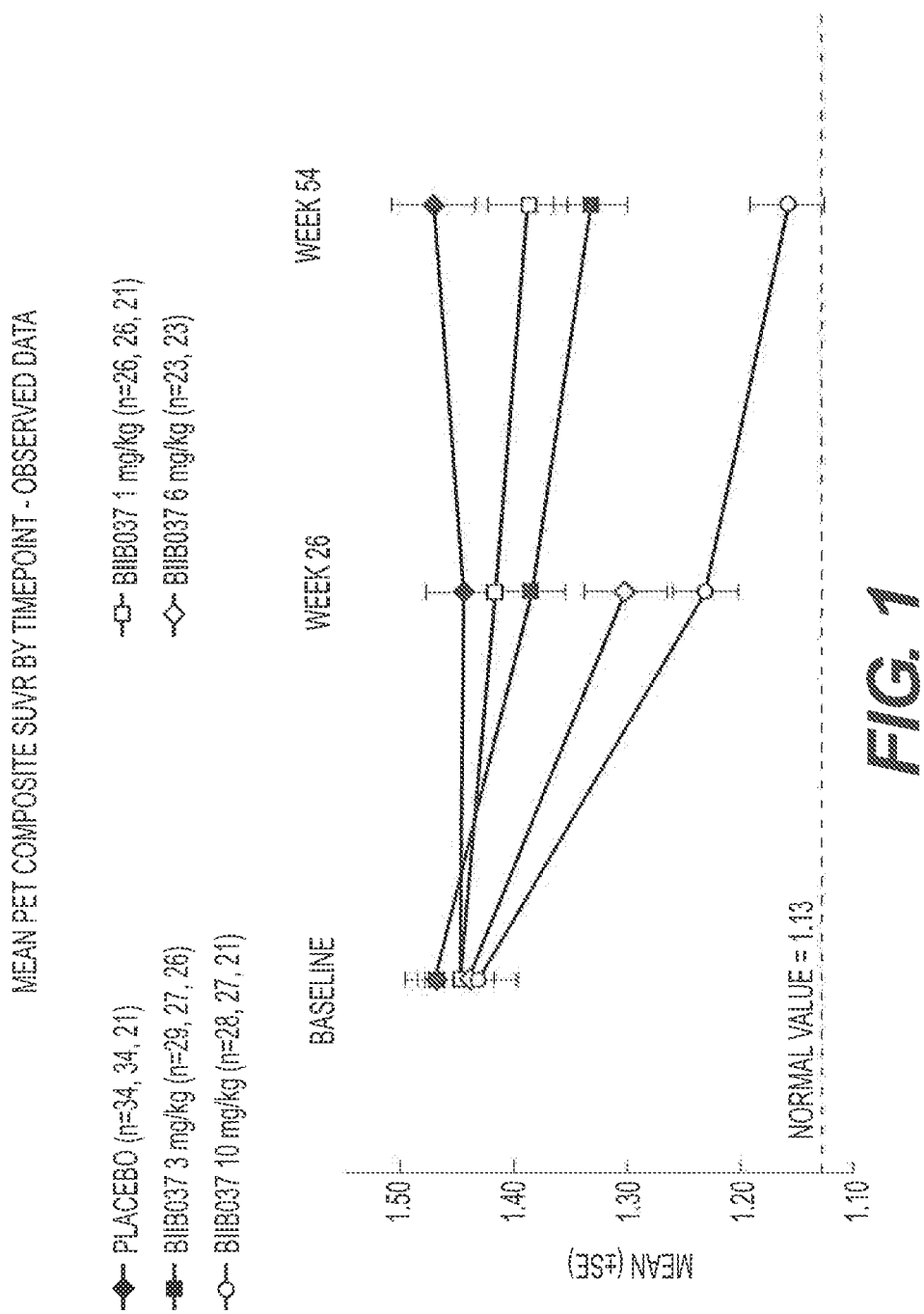
FIG. 1 shows the mean positron emission tomography (PET) composite standardized uptake ratio values (SUVR) by time point as determined by PET scans in a study of subjects treated with antibody BIIB037.

As used herein, the term "Alzheimer's disease", also referred to herein as "AD", means a dementia which is primarily identified by clinical diagnosis and established by markers of the disease.

AD is a continuum having certain operationally defined stages of disease progression. AD pathology begins prior to the onset of clinical symptoms. For example, amyoid plaques, one marker of AD pathology, form 10-20 years prior to the onset of AD dementia. The currently recognized stages of AD include preclinical, prodromal, mild, moderate, and severe. These stages may be further divided into sub-categories based on the severity of symptoms and measures of AD progression.

Because AD does not occur in discrete stages, those skilled in the art will recognize that the differences between patient groups may not be distinct in a particular clinical setting. Nevertheless, the clinical disease stage can be characterized by measures, and changes in these measures over time, such as amyloid-β accumulation (CSF/PET), synaptic dysfunction (FDG-PET/fMRI), tau-mediated neuronal injury (CSF), brain structure (volumetric MRI), cognition, and clinical function. Clifford Jack et al. Lancet. Neurol. 2010 January; 9(1):119.

Current core clinical criteria for all dementia, referred to as the NINCDS-ADRDA criteria (McKhann, 2011.), are known in the art and can be employed in practicing this invention. They include cognitive or behavioral impairment involving impaired ability to acquire and remember new information, impaired reasoning and handling of complex tasks, impaired visuospatial abilities, impaired language functions (speaking, reading, writing), and changes in personality, behavior, or comportment. Id. Alzheimer's disease is currently diagnosed using the core criteria and is typically characterized by symptoms which have a gradual onset over months to years, not sudden over hours or days (insidious onset). There is usually a clear-cut history of worsening of cognition by report or observation in Alzheimer's disease subjects. Id.

Other diagnostic classification systems have evolved as new information on AD has become available. These systems include the International Working Group (IWG) new research criteria for diagnosis of AD (Dubois B et al. *Lancet Neurol* 2007; 6(8):734-736), IWG research criteria, (Dubois et al. *Lancet Neurol* 2010; 9(11):1118-27), NIA/AA Criteria (Jack C R et al. *Alzheimer's Dement* 2011; 7(3):257-62), and DSM-5 criteria (American Psychiatric Association, DSM-5, 2013). These classification systems can also be employed in diagnosing AD subjects for treatment according to the methods of this invention.

Patients

The term "patient" is meant to include any human subject for whom diagnosis, prognosis, prevention, or therapy for Alzheimer's disease is desired, and includes a human subject in need of treatment. Those in need of treatment include those already with AD, as well as those prone to have AD, or those in which the manifestation of AD is to be prevented.

Typical patients will be men or women aged 50 to 90. In a preferred embodiment, the invention provides a method of treating a patient with AD (including, without limitation, patients with preclinical, prodromal, mild, moderate, or severe AD). In a further preferred embodiment, the patient has amyloid pathology confirmed, e.g., by PET imaging.

AD patients in need of treatment range from subjects with amyloid pathology and early neuronal degeneration to subjects with widespread neurodegeneration and irreversible neuronal loss with progressive cognitive and functional impairment to subjects with dementia.

Patients with preclinical AD can be identified by asymptomatic stages with or without memory complaints and emerging episodic memory and executive function deficits. This stage is typically characterized by the appearance of in vivo molecular biomarkers of AD and the absence clinical symptoms.

Prodromal AD patients are pre-dementia stage characterized predominantly by cognitive deficits and emerging functional impairment with disease progression. Prodromal AD patients typically have MMSE scores between 24-30 (inclusive), a spontaneous memory complaint, objective memory loss defined as a free recall score of ≤27 on the FCSRT, a global CDR score of 0.5, absence of significant levels of impairment in other cognitive domains, and essentially preserved activities of daily living, and an absence of dementia.

Patients with mild AD typically have MMSE scores between 20-26 (inclusive), a global CDR of 0.5 or 1.0, and meet the National Institute on Aging-Alzheimer's Association core clinical criteria for probable AD (see Section 22).

Basing AD diagnosis on clinical symptoms, mild stage AD patients will exhibit conspicuous behavior at work, forgetfulness, mood swings, and attention disturbances. Moderate stage AD patients will exhibit cognitive deficits, restricted everyday activities, orientation disturbance, apraxia, agnosia, aphasia, and behavioral abnormalities. Severe stage AD patients are characterized by loss of independence, decay of memory and speech, and incontinence, Treatment of earlier-stage patients who are amyloid positive as assessed by $^{18}$F-AV-45 PET scans is preferred. The patient may be asymptomatic for, or exhibit only transient symptoms of, headache, confusion, gait difficulties, or visual disturbances. The patient may or may not be an ApoE4 carrier as determined by ApoE genotyping.

Less preferred are patients having any medical or neurological condition (other than AD) that might be a contributing cause of the subject's cognitive impairment, such as stroke or other cerebrovascular condition, other neurodegenerative disease, a history of clinically significant psychiatric illness, acute or sub-acute micro- or macro hemorrhage, prior macrohemorrhage, or superficial siderosis, but even these patients can be treated following screening and selection by a qualified clinician.

Treatment

As used herein, the terms "treat" or "treatment" generally mean obtaining a desired pharmacological and/or physiological effect. The effect can be prophylactic in terms of completely or partially preventing Alzheimer's disease (AD) or symptoms thereof and/or can be therapeutic in terms of partially or completely curing AD and/or one or more adverse effects attributed to AD. Hence, the term "treatment" as used herein includes: (a) preventing AD from occurring in a subject who may be predisposed to AD, but has not yet been diagnosed as having it; (b) inhibiting AD, e.g. arresting its development; (c) relieving AD, e.g. causing regression of AD; or (d) prolonging survival as compared to expected survival if not receiving treatment.

In a preferred embodiment of the invention, the treatment is prophylactic for completely or partially preventing AD or symptoms thereof in the patient, or the treatment is therapeutic for partially or completely curing AD or symptoms attributed to AD in the patient.

In another preferred embodiment of the invention, treatment has a disease modifying effect. This means that the treatment slows or delays the underling pathological or pathophysiological disease processes and there is an improvement in clinical signs and symptoms of AD relative to placebo.

In a further preferred embodiment, treatment results in symptomatic improvement. This may consist of enhanced cognition, more autonomy, and/or improvement in neuropsychiatric and behavioral dysfunction, even if for only a limited duration.

While the goal of any therapy is the prevention or cure of disease, it will be understood that this invention contemplates a delay of clinical decline or progression of disease or relief of symptoms. Delaying clinical decline or disease progression directly impacts the patient and care-givers. It delays disability, maintains independence, and allows the patient to live a normal life for a longer period of time. Relief of symptoms to the best degree possible can incrementally improve cognition, function, and behavioral symptoms, as well as mood.

In the method of treatment of AD according to the invention, a recombinant, fully human, anti-amyloid beta monoclonal antibody is administered to the human patient. In a preferred embodiment, the monoclonal antibody has an excellent safety profile while being selective for soluble Aβ oligomer and fibril binding without substantial monomer binding. These properties improve Pk, reduce antibody sink, and minimize off-target cross-reactivity with APP-expressing tissues. A preferred monoclonal antibody meeting these criteria is antibody BIIB037.

Antibody BIIB037 is a biologic treatment for Alzheimer's disease. It is a non-naturally occurring, recombinant, fully human, anti-Aβ monoclonal antibody that recognizes aggregated forms of Aβ, including plaques. BIIB037 is an IgG$_1$ consisting of 2 heavy and 2 kappa light chains connected by inter-chain disulfide bonds.

In vitro characterization studies have established that antibody BIIB037 recognizes a conformational epitope present in Aβ aggregates, the accumulation of which is believed to underlie the development and progression of AD.

In vivo pharmacology studies indicate that a murine IgG2a chimeric version of the antibody (chI 2F6A) with similar properties significantly reduces amyloid plaque burden in the brains of aged Tg2576 mice, a mouse model of AD. The reduction in parenchymal amyloid was not accompanied by a change in vascular amyloid, as has been reported for certain anti-Aβ antibodies [Wilcock and Colton 2009].

Antibody BIIB037 has an amino acid sequence identical to the amino acid sequence of antibody 12F6A, which is a recombinant, fully human anti-AβIgG$_1$ mAb produced in a different Chinese hamster ovary cell line than BIIB037. Antibody BIIB037 has an antigen binding domain comprising $V_H$ and/or $V_L$ variable regions depicted in Table 1 ($V_H$) and Table 2 ($V_L$) and corresponding complementarity determining regions (CDRs) depicted in Table 3.

TABLE 1

Amino acid sequences of the $V_H$ region of neoepitope specific antibody BIIB037.

Variable heavy chain sequence

QVQLVESGGGVVQPGRSLRLSCAASGFAFSSYGMHWVRQAPGKGLEWVAV
IWFDGTKKYYTDSVKGRFTISRDNSKNTLYLQMNTLRAEDTAVYYCARDR
GIGARRGPYYMDVWGKGTTVYVSS (SEQ ID NO: 1)

TABLE 2

Amino acid sequences of the $V_L$ region of neoepitope specific antibody BIIB037.

Variable light chain sequence (kappa or lambda)

DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPLTFGG
GTKVEIKR (SEQ ID NO: 2)

TABLE 3

Denomination of CDR protein sequences in Kabat Nomenclature of $V_H$ and $V_L$ regions of neoepitope specific antibody BIIB037.

| CDR | Variable heavy chain | Variable light chain |
|---|---|---|
| CDR1 | SYGMH (SEQ ID NO: 3) | RASQSISSYLN (SEQ ID NO: 6) |
| CDR2 | VIWEDGMKYYTDSVKG (SEQ ID NO: 4) | AASSLQS (SEQ ID NO: 7) |
| CDR3 | DRGIGARRGPYYMDV (SEQ ID NO: 5) | QQSYSTPLI (SEQ ID NO: 8) |

In addition to antibody BIIB037, this invention contemplates the use of the other antibodies, such as antibodies comprising the VH region in Table 1 and the VL region in Table 2. Other antibodies contemplated for use in the invention include antibodies comprising the variable heavy chain CDRs and the variable light chain CDRs in Table 3.

Antibody BIIB037 and other antibodies employed in the invention can be prepared using known methods. In some embodiments, the antibody is expressed in an appropriate Chinese hamster ovary cell line.

The patient's response to treatment according to the invention is generally dose-dependent. One embodiment of the invention comprises administering at least one dose of the monoclonal antibody to the patient in an amount that is less than the minimum therapeutic amount required to treat the patient for AD. This is followed by at least one dose administered to the patient in an amount that is about equal to the minimum therapeutic amount required to treat the patient for AD. And then at least one dose is administered to the patient in an effective amount that is more than the minimum therapeutic amount, but less than the maximum tolerated amount required to treat the patient for AD. In a preferred embodiment, cerebral amyloid burden is reduced. In a further preferred embodiment, the susceptibility of the patient to ARIA is reduced.

A therapeutically effective amount refers to the amount of the antibody sufficient to ameliorate a symptom or condition associated with Alzheimer's disease. Therapeutic efficacy and toxicity of the monoclonal antibody can be determined by standard pharmacological procedures. Ideally, the monoclonal antibody is employed in an amount sufficient to restore normal behavior and/or cognitive properties in case of Alzheimer's disease, or at least delay or prevent the progression of AD in the patient.

In Tg2576 mice, a dose-dependent reduction in cerebral amyloid was observed after chronic dosing with monoclonal antibody BIIB037 (0.3 mg/kg to 30 mg/kg). A significant amyloid reduction was observed at 3 mg/kg, deemed the minimum therapeutic dose for antibody BIIB037 in this animal model.

An effective amount of the monoclonal antibody is that quantity of the antibody that will produce a clinically significant response in the treatment of Alzheimer's disease. Effective amounts of about 1 to 30 mg/kg per month can be employed. Efficacy of antibody BIIB037 can reach a plateau at effective amounts between about 10 mg/kg and about 30 mg/kg of the patient's body weight, consistent with safety. An effective amount of about 3 mg/kg to about 10 mg/kg of the patient's body weight is contemplated. Preferred effective amounts are about 3 mg/kg, about 6 mg/kg, and about 10 mg/kg of the patient's body weight.

The maximum tolerated amount of the monoclonal antibody is that quantity of the antibody which will produce a clinically significant response in the treatment of Alzheimer's disease consistent with safety. A principal safety concern in treating patients according to the method of the invention is the occurrence of ARIA, especially ARIA-E or ARIA-H. Consistent with achieving these outcomes, doses above about 60 mg/kg should be avoided. The methods of the invention make it possible to employ higher doses of antibody BIIB037 for the treatment of patients for AD than was feasible using previously known protocols.

It will be understood that dose adjustments can be implemented during the treatment protocol. For example, for reasons of safety or efficacy, doses can be increased so that the effects of the monoclonal antibody on AD can be enhanced or doses can be decreased so that the ARIA rate and severity can be mitigated. If a dose is missed, the patient should preferably resume dosing by receiving the missed dose and continuing thereafter according to the described regimen.

The monoclonal antibody is preferably administered to the patient by intravenous infusion following dilution into saline. When using this mode of administration, each infusion step in the titration regime of the invention will typically take about 1 hour.

The dose ranges and other numerical values herein include a quantity that has the same effect as the numerically stated amount as indicated by treatment of Alzheimer's disease in the patient and a reduction in the incidence or susceptibility of the patient to ARIA when compared to an individual not treated by the method of the invention. At the very least, each numerical parameter should be construed in light of the number of significant digits, applying ordinary rounding techniques. In addition, any numerical value inherently contains certain errors from the standard deviation of its measurement and such values are within the scope of the invention.

Titration (Sequential Administration)

It has been observed that the occurrence of the ARIA in AD patients treated with the BIIB037 antibody is dose-dependent. ARIA has been observed in patients receiving 1 mg/kg and 3 mg/kg of the antibody after the third and fifth doses. At doses of 6 mg/kg and 10 mg/kg of body weight, ARIA has been observed after the second dose. The methods of the invention include treatment regimens selected to decrease the incidence of ARIA.

More particularly, in the method of treatment of Alzheimer's disease (AD) according to the invention, the recombinant, fully human, anti-amyloid beta monoclonal antibody is administered to the human patient in increasing amounts over a period of time. This procedure of sequentially administering the antibody to the patient is referred to herein as "titration" because it involves administering a standardized pharmaceutical of known concentration in carefully measured amounts until completion of the procedure as evidenced by specific endpoints. In the present invention, the endpoints include the effect of the treatment on Alzheimer's disease in the patient and the effect of the treatment in reducing the incidence of ARIA, especially ARIA-E or ARIA-H, in the treated patient population.

One of the advantages of the titration regime of the invention is that it makes it possible to administer higher doses of the monoclonal antibody to AD patients, especially apolipoprotein E4 (ApoE4) carriers, without incurring the same extent of ARIA observed with a fixed-dose regimen. Without intending to be limited to any particular mechanism, it is believed that titration results in lower initial amyloid removal and slower removal during the overall treatment.

Titration of the monoclonal antibody is carried out in multiple doses. For example, two doses of the antibody can be administered to the patient in an amount per dose that is less than the minimum therapeutic amount, followed by 4 doses of the antibody in an amount per dose that is about equal to the minimum therapeutic amount. This regime can then be followed by multiple doses in an amount per dose that is more than the minimum therapeutic amount, but less than the maximum tolerated amount until there is an acceptable change in AD in the patient. For example, doses can be administered approximately 4 weeks apart over approximately 52 weeks (a total of 14 doses). Progress can be monitored by periodic assessment.

A particularly preferred protocol according to the invention, designated Protocol (1), comprises:

(A) administering the recombinant, fully human anti-amyloid beta monoclonal antibody to the patient in an amount of 1 mg/kg of body weight of the patient;

(B) 4 weeks after step (A), administering the antibody to the patient in an amount of 1 mg/kg of body weight of the patient;

(C) 4 weeks after step (B), administering the antibody to the patient in an amount of 3 mg/kg of body weight of the patient;

(D) 4 weeks after step (C), administering the antibody to the patient in an amount of 3 mg/kg of body weight of the patient;

(E) 4 weeks after step (D), administering the antibody to the patient in an amount of 3 mg/kg of body weight of the patient;

(F) 4 weeks after step (E), administering the antibody to the patient in an amount of 3 mg/kg of body weight of the patient;

(G) 4 weeks after step (F), administering the antibody to the patient in an amount of 6 mg/kg of body weight of the patient; and (H) in consecutive intervals of 4 weeks after step (G), administering the antibody to the patient in an amount of 6 mg/kg of body weight of the patient.

In other words, Protocol (1) comprises administering a first dose of recombinant, fully human anti-amyloid beta monoclonal antibody to the patient in an amount of 1 mg/kg of body weight of the patient, followed by a second dose in an amount of 1 mg/kg of body weight four weeks after the first dose. In four week intervals after the second dose, doses 3, 4, 5, and 6 of the antibody are administered to the patient in an amount of 3 mg/kg of body weight. And then, in four week intervals after administration of dose 6, doses 7 and 8 of the antibody are administered to the patient in an amount of 6 mg/kg of body weight.

Protocol (1) may comprise a total of 14 doses administered about 4 weeks apart over about 52 weeks, optionally continuing to dose about every 4 weeks thereafter, to thereby treat AD with reduced susceptibility of the patient to amyloid related imaging abnormalities (ARIA). In other words, four weeks after the administration of dose 8, doses 9-14 may be administered to the patient in an amount of 6 mg/kg body weight in four week intervals. In some embodiments, the antibody continues to be administered to the patient in an amount of 6 mg/kg of body weight every 4 weeks to at least week 76. In other words, in some embodiments, the method comprises administering doses 9-20 to the patient in an amount of 6 mg/kg body weight in four week intervals following dose 8. In some embodiments, after dose 8, the antibody is administered to the patient in an amount of 6 mg/kg of body weight every 4 weeks indefinitely. In some embodiments, in 12 week intervals following the last dose at 6 mg/kg body weight, the amount of antibody administered to the patient is 3 mg/kg body weight. In some embodiments, this reduced dose is initially administered to the patient 12 weeks after week 52 (i.e., 12 weeks after dose 14); in other embodiments, this reduced dose is administered to the patient 12 weeks after week 76 (i.e., 12 weeks after dose 20). In some embodiments, in four week intervals after the last dose at 6 mg/kg body weight, the amount of antibody administered to the patient is 1 mg/kg body weight. In some embodiments, this reduced dose is initially administered to the patient four weeks after week 52 (i.e., four weeks after dose 14); in other embodiments, this reduced dose is initially administered to the patient four weeks after week 76 (i.e., four weeks after dose 20).

Protocol (1) may be employed with patients designated as an ApoE4 carrier or an ApoE4 non-carrier as determined by ApoE genotyping. In any of the alternative embodiments of Protocol (1), the antibody may comprise a heavy chain variable region (VH) and a light chain variable region (VL), wherein the VH comprises a first complementarity determining region (VHCDR1) with the amino acid sequence SEQ ID NO:3, a VHCDR2 with the amino acid sequence SEQ ID NO:4, and a VHCDR3 with the amino acid sequences SEQ ID NO:5, and wherein the VL comprises a VLCDR1 with the amino acid sequence SEQ ID NO:6, a VLCDR2 with the amino acid sequence SEQ ID NO:7, and a VLCDR3 with the amino acid sequence SEQ ID NO:8. In preferred embodiments of Protocol (1), the antibody comprises a human IgG1 constant region. In particularly preferred embodiments of Protocol (1), the VH comprises SEQ ID NO:1 and the VL comprises SEQ ID NO:2.

Another particularly preferred protocol according to the invention, designated Protocol (2), comprises:
  (A) administering the recombinant, fully human anti-amyloid beta monoclonal antibody to the patient in an amount of 1 mg/kg of body weight of the patient;
  (B) 4 weeks after step (A), administering the antibody to the patient in an amount of 1 mg/kg of body weight of the patient;
  (C) 4 weeks after step (B), administering the antibody to the patient in an amount of 3 mg/kg of body weight of the patient;
  (D) 4 weeks after step (C), administering the antibody to the patient in an amount of 3 mg/kg of body weight of the patient;
  (E) 4 weeks after step (D), administering the antibody to the patient in an amount of 6 mg/kg of body weight of the patient;
  (F) 4 weeks after step (E), administering the antibody to the patient in an amount of 6 mg/kg of body weight of the patient; and
  (G) in consecutive intervals of 4 weeks after step (F), administering the antibody to the patient in an amount of 10 mg/kg of body weight of the patient.

In other words, Protocol (2) comprises administering a first dose of recombinant, fully human anti-amyloid beta monoclonal antibody to the patient in an amount of 1 mg/kg of body weight of the patient, followed by a second dose in an amount of 1 mg/kg of body weight four weeks after the first dose. In four week intervals after the second dose, antibody doses 3 and 4 are administered to the patient in an amount of 3 mg/kg of body weight. In four week intervals after administration of dose 4, doses 5 and 6 of the antibody are administered to the patient in an amount of 6 mg/kg of body weight. And then, four weeks after administration of dose 6, antibody dose 7 is administered to the patient in an amount of 10 mg/kg of body weight.

Protocol (2) may comprise a total of 14 doses administered about 4 weeks apart over about 52 weeks, optionally continuing to dose about every 4 weeks thereafter, to thereby treat AD with reduced susceptibility of the patient to amyloid related imaging abnormalities (ARIA). In other words, four weeks after the administration of dose 7, doses 8-14 may be administered to the patient in an amount of 10 mg/kg body weight in four week intervals. In some embodiments, the antibody continues to be administered to the patient in an amount of 10 mg/kg of body weight every 4 weeks to at least week 76. In other words, in some embodiments, the method comprises administering doses 8-20 to the patient in an amount of 10 mg/kg body weight in four week intervals following dose 7. In some embodiments, following dose 7, the antibody is administered to the patient in an amount of 10 mg/kg of body weight every 4 weeks indefinitely. In some embodiments, after the last dose at 10 mg/kg body weight, the amount of antibody is reduced to 3 mg/kg body weight and is administered to the patient in 12 week intervals. In some embodiments, this reduced dose is initially administered to the patient 12 weeks after week 52 (i.e., 12 weeks after dose 14); in other embodiments, this reduced dose is initially administered to the patient 12 weeks after week 76 (i.e., 12 weeks after dose 20). In some embodiments, four weeks after the last dose at 10 mg/kg body weight, the amount of antibody administered to the patient is reduced to 1 mg/kg body weight every 4 weeks. In some embodiments, this reduced dose begins four weeks after week 52 (i.e., four weeks after dose 14); in other embodiments, this reduced dose begins four weeks after week 76 (i.e., four weeks after dose 20).

Protocol (2) is especially well suited for the treatment of ApoE4 non-carriers. In any of the alternative embodiments of Protocol (2), the antibody may comprise a heavy chain variable region (VH) and a light chain variable region (VL), wherein the VH comprises a first complementarity determining region (VHCDR1) with the amino acid sequence SEQ ID NO:3, a VHCDR2 with the amino acid sequence SEQ ID NO:4, and a VHCDR3 with the amino acid sequences SEQ ID NO:5, and wherein the VL comprises a VLCDR1 with the amino acid sequence SEQ ID NO:6, a VLCDR2 with the amino acid sequence SEQ ID NO:7, and a VLCDR3 with the amino acid sequence SEQ ID NO:8. In preferred embodiments of Protocol (2), the antibody comprises a human IgG1 constant region. In particularly preferred embodiments of Protocol (2), the VH comprises SEQ ID NO:1 and the VL comprises SEQ ID NO:2.

This invention provides another particularly preferred protocol, designated Protocol (3), for the treatment of ApoE4 carriers. This embodiment according to the invention comprises:
(A) administering the recombinant, fully human anti-amyloid beta monoclonal antibody to the patient in an amount of 1 mg/kg of body weight of the patient;
(B) 4 weeks after step (A), administering the antibody to the patient in an amount of 1 mg/kg of body weight of the patient; and
(C) in consecutive intervals of 4 weeks after step (B), administering the antibody to the patient in an amount of 3 mg/kg of body weight of the patient.

In other words, Protocol (3) comprises administering a first dose of a recombinant, fully human anti-amyloid beta monoclonal antibody to the patient in an amount of 1 mg/kg of body weight of the patient. Four weeks after the first dose, a second dose of the antibody is administered to the patient in an amount of 1 mg/kg of body weight. And then, 4 weeks after the second dose, dose 3 of the antibody is administered to the patient in an amount of 3 mg/kg of body weight.

Protocol 3 may comprise a total of 14 doses administered about 4 weeks apart over about 52 weeks, optionally continuing to dose about every 4 weeks thereafter, to thereby treat AD with reduced susceptibility of the patient to amyloid related imaging abnormalities (ARIA). In other words, four weeks after the administration of dose 3, doses 4-14 may be administered to the patient in an amount of 3 mg/kg body weight in four week intervals. In some embodiments, the antibody continues to be administered to the patient in an amount of 3 mg/kg of body weight every 4 weeks to at least week 76. In other words, in some embodiments, the method comprises administering doses 4-20 to the patient in an amount of 3 mg/kg body in four week intervals following dose 3. In some embodiments, following dose 3, the antibody is administered to the patient in an amount of 3 mg/kg of body weight every 4 weeks indefinitely. In some embodiments, after a prescribed period, the amount of antibody administered to the patient may be reduced to 3 mg/kg body weight every 12 weeks. In some embodiments, the 12 week dosing intervals begin after week 52 (i.e., after dose 14); in other embodiments, the 12 week dosing intervals begin after week 76 (i.e., after dose 20). In some embodiments, after a prescribed period, the amount of antibody administered to the patient may be reduced to 1 mg/kg body weight every 4 weeks. In some embodiments, this reduced dose begins four weeks after week 52 (i.e., four weeks after dose 14); in other embodiments, this reduced dose begins four weeks after week 76 (i.e., four weeks after dose 20).

Protocol (3) may be used with ApoE4 carriers as determined by ApoE genotyping. In any of the alternative embodiments of Protocol (3), the antibody may comprise a heavy chain variable region (VH) and a light chain variable region (VL), wherein the VH comprises a first complementarity determining region (VHCDR1) with the amino acid sequence SEQ ID NO:3, a VHCDR2 with the amino acid sequence SEQ ID NO:4, and a VHCDR3 with the amino acid sequences SEQ ID NO:5, and wherein the VL comprises a VLCDR1 with the amino acid sequence SEQ ID NO:6, a VLCDR2 with the amino acid sequence SEQ ID NO:7, and a VLCDR3 with the amino acid sequence SEQ ID NO:8. In preferred embodiments of Protocol (3), the antibody comprises a human IgG1 constant region. In particularly preferred embodiments of Protocol (3), the VH comprises SEQ ID NO:1 and the VL comprises SEQ ID NO:2.

Another particularly preferred protocol according to the invention, designated Protocol (4), comprises:
(A) administering the recombinant, fully human anti-amyloid beta monoclonal antibody to the patient in an amount of 1 mg/kg of body weight of the patient;
(B) 4 weeks after step (A), administering the antibody to the patient in an amount of 1 mg/kg of body weight of the patient;
(C) 4 weeks after step (B), administering the antibody to the patient in an amount of 3 mg/kg of body weight of the patient;
(D) 4 weeks after step (C), administering the antibody to the patient in an amount of 3 mg/kg of body weight of the patient; and
(E) 4 weeks after step (D), administering the antibody to the patient in an amount of 6 mg/kg of body weight of the patient.

In other words, Protocol (4) comprises administering a first dose of recombinant, fully human anti-amyloid beta monoclonal antibody to the patient in an amount of 1 mg/kg of body weight of the patient, followed by a second dose in an amount of 1 mg/kg of body weight four weeks after the first dose. In four week intervals after the second dose, doses 3 and 4 are administered to the patient in an amount of 3 mg/kg of body weight. And then, four weeks after administration of dose 4, dose 5 of the antibody is administered to the patient in an amount of 6 mg/kg of body weight.

Protocol (4) may comprise a total of 14 doses administered about 4 weeks apart over about 52 weeks, optionally continuing to dose about every 4 weeks thereafter, to thereby treat AD with reduced susceptibility of the patient to amyloid related imaging abnormalities (ARIA). In other words, four weeks after the administration of dose 5, doses 6-14 may be administered to the patient in an amount of 6 mg/kg body weight in four week intervals. In some embodiments, the antibody continues to be administered to the patient in an amount of 6 mg/kg of body weight every 4 weeks to at least week 76. In other words, in some embodiments, the method comprises administering doses 6-20 to the patient in an amount of 6 mg/kg body weight in four week intervals following dose 5. In some embodiments, following dose 5, the antibody is administered to the patient in an amount of 6 mg/kg of body weight every 4 weeks indefinitely. In some embodiments, after the last dose at 6 mg/kg body weight, the amount of antibody administered to the patient is reduced to 3 mg/kg body weight every 12 weeks. In some embodiments, this reduced dose is initially administered to the patient 12 weeks after week 52 (i.e., 12 weeks after dose 14); in other embodiments, this reduced dose is initially administered to the patient 12 weeks after week 76 (i.e., 12 weeks after dose 20). In some embodiments, after the last dose at 10 mg/kg body weight, the amount of antibody administered to the patient is reduced to 1 mg/kg body weight every 4 weeks. In some embodiments, this reduced dose begins four weeks after week 52 (i.e., four weeks after dose 14); in other embodiments, this reduced dose begins four weeks after week 76 (i.e., four weeks after dose 20).

In any of the embodiments of Protocol (4), the antibody may comprise a heavy chain variable region (VH) and a light chain variable region (VL), wherein the VH comprises a first complementarity determining region (VHCDR1) with the amino acid sequence SEQ ID NO:3, a VHCDR2 with the amino acid sequence SEQ ID NO:4, and a VHCDR3 with the amino acid sequences SEQ ID NO:5, and wherein the VL comprises a VLCDR1 with the amino acid sequence SEQ ID NO:6, a VLCDR2 with the amino acid sequence SEQ ID NO:7, and a VLCDR3 with the amino acid sequence SEQ ID NO:8. In preferred embodiments of Protocol (4), the antibody comprises a human IgG1 constant region. In particularly preferred embodiments of Protocol (4), the VH comprises SEQ ID NO:1 and the VL comprises SEQ ID NO:2.

Yet another particularly preferred protocol according to the invention, designated as Protocol (5), comprises:
(A) administering the recombinant, fully human anti-amyloid beta monoclonal antibody to the patient in an amount of 1 mg/kg of body weight of the patient;
(B) 4 weeks after step (A), administering the antibody to the patient in an amount of 1 mg/kg of body weight of the patient;
(C) 4 weeks after step (B), administering the antibody to the patient in an amount of 3 mg/kg of body weight of the patient;
(D) 4 weeks after step (C), administering the antibody to the patient in an amount of 3 mg/kg of body weight of the patient;
(E) 4 weeks after step (D), administering the antibody to the patient in an amount of 3 mg/kg of body weight of the patient;
(F) 4 weeks after step (E), administering the antibody to the patient in an amount of 3 mg/kg of body weight of the patient;
(G) in consecutive intervals of 4 weeks after step (F), administering the antibody to the patient in an amount of 6 mg/kg of body weight of the patient;
(H) in consecutive intervals of 4 weeks after step (G), administering the antibody to the patient in an amount of 6 mg/kg of body weight of the patient;
(I) in consecutive intervals of 4 weeks after step (H), administering the antibody to the patient in an amount of 6 mg/kg of body weight of the patient;
(J) in consecutive intervals of 4 weeks after step (I), administering the antibody to the patient in an amount of 6 mg/kg of body weight of the patient;
(K) in consecutive intervals of 4 weeks after step (J), administering the antibody to the patient in an amount of 6 mg/kg of body weight of the patient; and
(L) in consecutive intervals of 4 weeks after step (K), administering the antibody to the patient in an amount of 10 mg/kg of body weight of the patient.

In other words, Protocol 5 comprises administering a first dose of recombinant, fully human anti-amyloid beta monoclonal antibody to the patient in an amount of 1 mg/kg of body weight of the patient, followed by a second dose in an amount of 1 mg/kg of body weight four weeks after the first dose. In four week intervals after the second dose, antibody doses 3, 4, 5, and 6 are administered to the patient in an amount of 3 mg/kg of body weight. In four week intervals after administration of dose 6, doses 7, 8, 9, 10, and 11 are administered to the patient in an amount of 6 mg/kg of body weight. And then, four weeks after administration of dose 11, dose 12 of the antibody is administered to the patient in an amount of 10 mg/kg of body weight.

Protocol (5) may comprise a total of 14 doses administered about 4 weeks apart over about 52 weeks, optionally continuing to dose about every 4 weeks thereafter, to thereby treat AD with reduced susceptibility of the patient to amyloid related imaging abnormalities (ARIA). In other words, four weeks after the administration of dose 12, doses 13-14 may be administered to the patient in an amount of 10 mg/kg body weight in four week intervals. In some embodiments, the antibody continues to be administered to the patient in an amount of 10 mg/kg of body weight every 4 weeks to at least week 76. In other words, in some embodiments, the method comprises administering doses 13-20 to the patient in an amount of 6 mg/kg body weight in four week intervals following dose 12. In some embodiments, following dose 12, the antibody is administered to the patient in an amount of 10 mg/kg of body weight every 4 weeks indefinitely. In some embodiments, after the last dose at 10 mg/kg body weight, the amount of antibody administered to the patient is reduced to 3 mg/kg body weight every 12 weeks. In some embodiments, this reduced dose is initially administered to the patient 12 weeks after week 52 (i.e., 12 weeks after dose 14); in other embodiments, this reduced dose is initially administered to the patient 12 weeks after week 76 (i.e., 12 weeks after dose 20). In some embodiments, after the last dose at 10 mg/kg body weight, the amount of antibody administered to the patient is reduced to 1 mg/kg body weight every 4 weeks. In some embodiments, this reduced dose begins four weeks after week 52 (i.e., four weeks after dose 14); in other embodiments, this reduced dose begins four weeks after week 76 (i.e., four weeks after dose 20).

In any of the embodiments of Protocol (5), the antibody may comprise a heavy chain variable region (VH) and a light chain variable region (VL), wherein the VH comprises a first complementarity determining region (VHCDR1) with the amino acid sequence SEQ ID NO:3, a VHCDR2 with the amino acid sequence SEQ ID NO:4, and a VHCDR3 with the amino acid sequences SEQ ID NO:5, and wherein the VL comprises a VLCDR1 with the amino acid sequence SEQ ID NO:6, a VLCDR2 with the amino acid sequence SEQ ID NO:7, and a VLCDR3 with the amino acid sequence SEQ ID NO:8. In preferred embodiments of Protocol (5), the antibody comprises a human IgG1 constant region. In particularly preferred embodiments of Protocol (5), the VH comprises SEQ ID NO:1 and the VL comprises SEQ ID NO:2.

Figure 10:
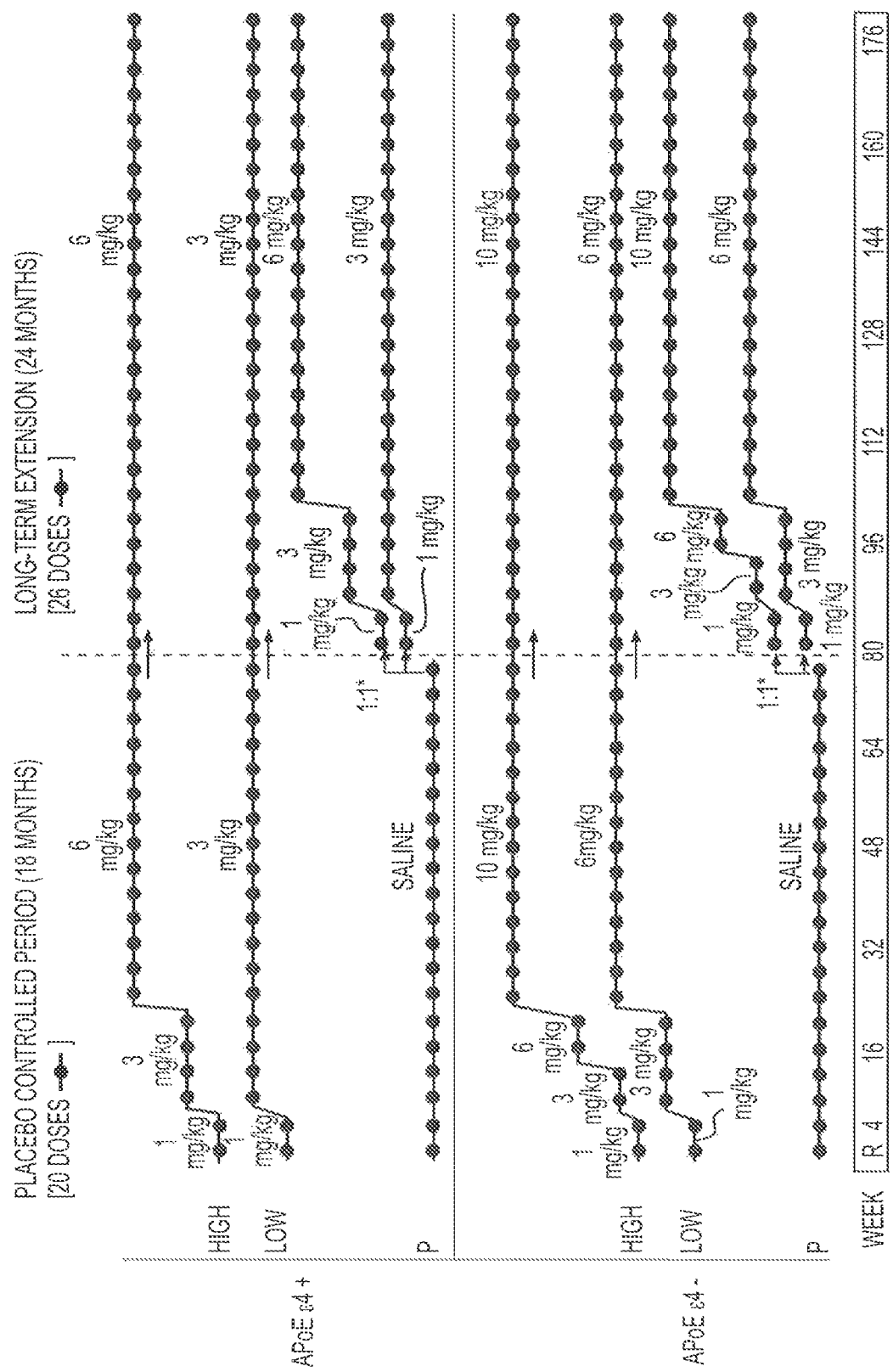
FIG. 10 depicts selected dosing schedules for ApoE4 carriers and non-carriers.

Exemplary dosing schemes for ApoE4 carriers and non-carriers are described in Table 10 in Example 8 and in FIG. 10.

These particularly preferred protocols optimize efficacy with safety requirements. In preferred embodiments of the invention, the patient's susceptibility to vasogenic edema (VE) is reduced, or the patient's susceptibility to cerebral microhemorrhages (mH) is reduced, or both VE and mH are reduced in the patient.

Variations of these preferred protocols are also possible. A dosing scheme of multiple doses of 1 mg/kg of the patient's body weight at periodic intervals between doses, followed by multiple doses of 3 mg/kg at periodic intervals between doses can be employed. For example, a dosing scheme comprises 2 doses of 1 mg/kg of the patient's body weight at intervals of 4 weeks between doses, followed by 4 doses of 3 mg/kg at intervals of 4 weeks between doses. Another example of this dosing scheme comprises 2 doses of 1 mg/kg of the patient's body weight at intervals of 4 weeks between doses, followed by multiple doses of 3 mg/kg at intervals of 4 weeks between doses until treatment is terminated. Another example of this dosing scheme comprises 4 doses of 1 mg/kg of the patient's body weight at intervals of 4 weeks between doses, followed by multiple doses of 3 mg/kg at intervals of 4 weeks between doses until treatment is terminated. Given that ARIA generally occurs between doses 2 and 5, this abbreviated protocol can provide an additional margin of safety. In this event, it will not be necessary for patients to continue to titrate to 6 mg/kg, but rather escalation of the dose can be stopped at about 3 mg/kg of the patient's body weight.

Another variation of these preferred protocols comprises a dosing scheme of multiple doses of 1 mg/kg of the patient's body weight at periodic intervals between doses, followed by multiple doses of 3 mg/kg at periodic intervals between doses can be employed, and finally multiple doses of 6 mg/kg of the patient's body weight at periodic intervals between doses until treatment is terminated. An example of this dosing scheme comprises 2 doses of 1 mg/kg of the patient's body weight at intervals of 4 weeks between doses, followed by 4 doses of 3 mg/kg at intervals of 4 weeks between doses can be employed, and finally multiple doses of 6 mg/kg of the patient's body weight until the treatment is terminated.

In a further embodiment of the invention, titration of the monoclonal antibody to the patient can be dispensed with if the patient exhibits the appropriate responses without the titration steps. In this event, for example, an ApoE4 carrier can be administered a dose of the monoclonal antibody of 1 mg/kg or 3 mg/kg of the patient's body weight, and an ApoE4 non-carrier can be administered a dose of 3 mg/kg or 6 mg/kg or 10 mg/kg of the patient's body weight. A total of 14 doses can be administered about 4 weeks apart over about 52 weeks, optionally continuing to dose about every 4 weeks thereafter, to thereby treat AD with reduced susceptibility of the patient to amyloid related imaging abnormalities (ARIA).

Compositions

The antibody BIIB037 can be formulated as a pharmaceutical composition. The pharmaceutical compositions employed in the present invention can be formulated according to methods well known in the art; see, for example, Remington: The Science and Practice of Pharmacy (2000) by the University of Sciences in Philadelphia, ISBN 683-306472. The compositions can further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc.

Furthermore, the pharmaceutical composition may comprise additional agents. For example, for use in the treatment of Alzheimer's disease the additional agent can be selected from the group consisting of small organic molecules, other anti-Abeta antibodies, anti-Tau antibodies, and combinations thereof.

Administration of the compositions can be effected in different ways, e.g., by intravenous, intraperitoneal, subcutaneous, intramuscular, topical, or intradermal administration.

Measurement and Reduction in the Symptoms of AD

Measurement of the risk, existence, severity, and progression of Alzheimer's disease can be determined by clinical diagnosis over time; assessment of the global functional level of the patient; evaluation of the daily living capacities or behavioral deficits; volumetric analysis of brain structures; in vivo measurement of pathological deposits of abnormal proteins in brain (e.g. PET beta-amyloid imaging), or biochemical variables in body fluids (e.g. tau proteins or Abeta peptides); and by comparison to the natural course/history of the disease.

The following clinical assessments can be employed in determining the stage of Alzheimer's disease in the patient: CDR, FCSRT, Neuropsychiatric Inventory-Questionnaire (NPI-Q), and a neuropsychological test battery comprising Rey Auditory Verbal Learning Test (RAVLT) Immediate and Delayed Recall, Wechsler Memory Scale (WMS) Verbal Pair Associate Learning Test Immediate and Delayed Recall, Delis-Kaplan Executive Function System Verbal Fluency Conditions 1 and 2, and the Wechsler Adult Intelligence Scale Fourth Edition Symbol Search and Coding Subsets; and the Cognitive Drug Research computerized test battery.

A preferred diagnostic regime comprises determining the change from baseline on the Clinical Dementia Rating (CDR) Scale, a neuropsychological test battery, Cognitive Drug Research computerized test battery, the Free and Cued Selective Reminding Test (FCSRT), Mini Mental State Examination (MMSE), Columbia Suicide Severity Rating Scale (C-SSRS), and Neuropsychiatric Inventory-Questionnaire (NPI-Q).

Biomarkers have emerged as essential for defining AD and for staging of the disease along its spectrum. Biomarker phenotypes can bridge the gap between clinical phenotypes and neuropathology phenotypes, such as amyloid plaques, neurofibrillary tangles, inflammation, and neurodegeneration. Biomarkers of AD include ApoE isotype, CSF Aβ42, amyloid PET, CSF Tau, and hippocampal volumetric (HCV) MRI.

Amyloid plaque burden in certain areas of the brain can be measured by 18F-AV-45 PET. 18F-AV-45 is an amyloid ligand developed by Avid Radiopharmaceuticals (Philadelphia, Pa.). It binds to fibrillar Aβ with a high affinity (Kd=3.1 nM). Results with 18F-AV-45 PET imaging have shown that patients with AD have selective retention of tracer in cortical areas expected to be high in amyloid deposition, whereas healthy controls have shown rapid washout from these areas, with only minimal cortical tracer retention. A significant difference in mean uptake of 18F-AV-45 has been observed between AD and age-matched control subjects. Test-retest variance of 18F-AV-45 PET imaging is low (less than 5%) in both AD patients and cognitively healthy controls. Visual interpretation of the 18F-AV-45 PET images and mean quantitative estimates of cortical uptake correlate with presence and quantity of amyloid pathology at autopsy as measured by immunohistochemistry and silver stain neuritic plaque score [Clark et al. 2011].

Radiation dosimetry of 18F-AV-45 is in the range of typical PET ligands. The average human whole body effective dose is estimated to be 0.019 mSv/MBq. A dose of 370 MBq per injection has also been shown to yield good imaging results.

Patients with AD have characteristic reductions in FDG PET measurements of regional glucose metabolism, which are related to progressive impairment of cognitive function [Landau 2011; Mielke 1994]. The effect of BIIB037 in halting the progression of glucose metabolic deficit can be periodically assessed using FDG PET measurements. Radiation dosimetry of FDG is in the range of typical PET ligands. The average human whole body effective dose is estimated to be 0.019 mSv/MBq. The standard FDG imaging protocol uses a dose of 185 MBq per injection. In this invention, patients can typically receive up to 185 MBq with each scan.

Measurement of Aβ1-42 and T-Tau or P-Tau levels in CSF are gaining acceptance as predictive biomarkers of AD. Evidence suggests that Tau aggregation pathology is a very early event in pathogenesis. Duyckaerts (2011) Lancet Neurol. 10, 774-775, and Braak et al., (2013), Acta Neuropath., 126:631-41.

Alzheimer's disease-related biomarkers can also be employed. These include, but are not limited to, pyroglutamate-Aβ, Aβ40, and Aβ42 in blood, and total Tau, phospho-Tau, pyroglutamate-Aβ Aβ40, and Aβ42 in CSF.

Morphometric MRI measures can also aid in the assessment of AD. These include whole brain volume, hippocampal volume, ventricle volume, and cortical gray matter volume. Cerebral blood flow as measured by ASL-MRI and functional connectivity as measured by tf-fMRI can be included in the assessment protocols.

Use of antibody BIIB037 for the treatment of Alzheimer's disease patients according to the invention results in an improvement in one or more of these parameters over baseline measurements or at least prevents or slows the progression of AD from one stage to the next stage.

Measurement and Reduction of ARIA

Alzheimer's disease patients generally respond to the monoclonal antibody in a dose dependent manner. Therefore, it is advantageous to use high doses for maximum effectiveness. But the incidence or rate of ARIA can increase in certain patient populations when doses of the antibody are increased. This invention makes it possible to reduce the incidence of ARIA in susceptible patients undergoing treatment for Alzheimer's disease, especially those patients receiving high doses of the monoclonal antibody, as well as ApoE4 carriers. In particular, this invention makes it possible to reduce the incidence of amyloid related imaging abnormalities-edema (ARIA-E), or a reduce the incidence of amyloid related imaging abnormalities-hemorrhage or hemosiderosis (ARIA-H), or reduce both ARIA-E and ARIA-H.

Amyloid-related imaging abnormalities (ARIA), including edema (ARIA-E) and microhemorrhage or hemosiderosis (ARIA-H), are readily detectable by MRI (i.e., fluid attenuated inversion recovery (FLAIR/T2 for ARIA-E and T2*/gradient echo for ARIA-H). [Sperling 2012]. Susceptibility weighted imaging (SWI), an MRI technique potentially more sensitive than T2*/gradient echo in detecting ARIA-H [Sperling 2011], can also be employed.

Signs of vasogenic edema include hyperintense signal on T2-weighted and FLAIR sequences generally confined to the white matter and often associated with gyral swelling. Symptoms of vasogenic edema when present include headache, worsening cognitive function, alteration of consciousness, seizures, unsteadiness, and vomiting.

Patients who develop mild ARIA-E with no clinical symptoms at any time during treatment can continue at their current dose. MRIs can be obtained approximately every 4 weeks until the ARIA-E has resolved. An MMSE should be periodically administered to the patient until the ARIA-E resolves.

Treatment of patients who develop moderate or severe ARIA-E with no clinical symptoms at any time should be suspended. If on repeat follow-up MRIs, obtained approximately every 4 weeks, the ARIA-E has resolved and the subject remains asymptomatic, the patient may resume treatment, but at the next lower dose level. Patients should periodically receive an MMSE until the ARIA-E resolves before resuming dosing.

Patients who develop mild, moderate, or severe ARIA-E accompanied by moderate, severe, or serious clinical symptoms at any time should permanently discontinue treatment.

ARIA-H is monitorable by MRI and believed to be an imaging finding without clinical correlate (i.e., patients are asymptomatic) [Sperling 2011]. Specifically, hemorrhage is detectable using MRI sequences of gradient echo, T1-weighted, T2-weighted, and FLAIR. Microhemorrhage is usually asymptomatic, whereas macrohemorrhage typically has focal signs and symptoms reflecting the area of the affected brain as well as non-specific symptoms that include those for vasogenic edema. The frequency of MRI acquisition is driven by safety monitoring needs.

Patients who develop asymptomatic ARIA-H (<4 incident microhemorrhages) at any time during the treatment may continue with treatment at the current dose. Repeat MRI should be obtained at approximately 2-week intervals until deemed stable. Subjects should periodically be administered an MMSE until the ARIA-H is deemed stable.

Treatment of patients who develop ARIA-H (<4 incident microhemorrhages) accompanied by mild clinical symptoms, or subjects with single incident hemosiderosis (also referred to as superficial siderosis), who are asymptomatic or have mild clinical symptoms, should be suspended. Repeat MRI should be obtained at approximately 2-week intervals until deemed stable. Once the ARIA-H (microhemorrhage/hemosiderosis) is deemed stable and the clinical symptoms have resolved, the patient may resume treatment, but at the next lower dose level. Patients should periodically be administered an MMSE until the ARIA-H/hemosiderosis is deemed stable.

Subjects who develop ARIA-H (<4 incident microhemorrhages) accompanied by moderate, severe, or serious clinical symptoms, >4 incident microhemorrhages, any incident macrohemorrhage, or >1 incident hemosiderosis at any time, should permanently discontinue treatment.

Example 1

Toxicology Study of BIIB037 In Vivo

The Tg2576 mouse and cynomolgus monkey were used for BIIB037 toxicology evaluation. Of the 2 species, the Tg2576 mouse is considered the primary pharmacologically relevant species given that these mice accumulate amyloid plaques in the cerebral parenchyma and vasculature.

In addition to the standard histopathologic evaluation in mice, Perls staining of hemosiderin (a breakdown product of hemoglobin) was performed to quantify microhemorrhage. Microhemorrhage has been observed both as a background finding in transgenic mouse models of AD [Winkler et al. 2001], including Tg2576 mice [Kumar-Singh et al. 2005], and as a drug-related finding in transgenic mice treated with some anti-Aβ antibodies [Pfeifer et al. 2002; Racke et al. 2005; Wilcock and Colton 2009].

Example 2

Short Term Study of BIIB037 In Vivo

In a 13-week study, Tg2576 mice were administered weekly IV doses of 10 or 70 mg/kg of ch12F6A, or 500 mg/kg of either ch12F6A or BIIB037. Minimal to mild acute hemorrhage was observed in 2 mice dosed at ≥70 mg/kg/week as assessed by the standard histopathologic staining. Additional findings included a slight increase in the incidence and/or severity of meningeal vascular inflammation in mice treated at ≥70 mg/kg/week compared with control animals, and the occurrence of thrombosis in 2 animals dosed at 500 mg/kg/week. At the end of a 6-week drug-free recovery period, the incidence and severity of findings observed in ch12F6A and BIIB037-treated mice were within the range observed in the control group throughout the study.

In addition to standard histopathology of the brain, presence of microhemorrhage was evaluated by Perls staining; no significant differences in microhemorrhage were observed between ch12F6A/BIIB037 and control treated groups after 13 weeks of dosing.

The increased incidence and/or severity of meningeal vascular inflammation and acute hemorrhage observed at or greater than 70 mg/kg/week contributed towards the no observed adverse effect level (NOAEL) determination of 10 mg/kg/week.

Example 3

Longer Term Study of BIIB037 In Vivo

In a 6-month study, Tg2576 mice were administered weekly IV doses of 10 or 40 mg/kg of ch12F6A, or 250 mg/kg of either ch12F6A or BIIB037. There were no treatment-related changes in any of the parameters evaluated during the main and recovery periods, with the exception of a slight increase in the combined incidence and/or severity of meningeal/cerebral vascular inflammation and vascular thickening in the brains of main and early death animals treated with chimeric 12F6A (ch12F6A) comprising murine constant domains at doses ≥40 mg/kg, and an increase in area of micro hemorrhage in a subset of the 250 mg/kg ch12F6A-treated animals.

There were no treatment-related findings, nor increase in the incidence and/or severity of meningeal/cerebral vascular inflammation and/or vascular thickening in Tg2576 mice that received weekly intravenous injection administration of 250 mg/kg BIIB037 and no statistically significant difference in the number of foci and/or percent area of microhemorrhage in the brain of animals receiving ch12F6A or BIIB037.

After a 6-week recovery period, the incidence and/or severity of the vascular inflammation or thickening was similar across treated and control groups. Although a potential treatment-related exacerbation of these changes cannot be totally excluded, the vascular inflammation, thickening, and possible exacerbated microhemorrhage in the brain were considered of equivocal relationship to treatment and potentially due to the age-related degenerative changes inherent to the disease model alone. Consequently, the NOAEL is 250 mg/kg/week for this study.

No treatment-related findings were observed in a 4-week monkey study, the NOAEL was 300 mg/kg/week.

In summary, the toxicology evaluation for BIIB037 identified a toxicity profile consistent with binding of the antibody to deposited Aβ.

Example 4

Reduction of Amyloid Beta In Vivo

In Tg2576 mice, a dose-dependent reduction in cerebral amyloid was observed after chronic dosing with ch12F6A (0.3 mg/kg to 30 mg/kg). A significant amyloid reduction was observed at 3 mg/kg, deemed the minimal effective dose, and efficacy appeared to reach a plateau between 10 mg/kg and 30 mg/kg. The no observed adverse effect level (NOAEL) obtained from a 13-week Tg2576 mouse toxicology study (10 mg/kg/week) was used for the purpose of safety margin determination.

BIIB037 mean steady state exposure in humans (calculated as $AUC_{0-4wk}$) at 1 and 3 mg/kg is projected to be approximately one-twelfth and one-fourth the nonclinical NOAEL dose exposure (calculated as $AUC_{0-4wk}$) observed in the 13-week mouse toxicology study. BIIB037 mean steady state exposure following a 10 mg/kg dose is projected to be similar to NOAEL dose exposures. The highest dose, 30 mg/kg, is projected to achieve mean steady state exposures 2- to 3-times the NOAEL exposure and one-third the exposure at the 70 mg/kg dose where slight increases in the severity of meningeal vascular inflammation and incidences of cerebral hemorrhage were observed.

Example 5

Clinical Experience with BIIB037

The first clinical study is a Phase 1, randomized, blinded, placebo-controlled single ascending dose (SAD) study of the safety, tolerability, and pharmacokinetics (PK) of BIIB037 in subjects with mild to moderate AD. Fifty-three subjects were enrolled in the SAD study.

The starting dose of BIIB037 was 0.3 mg/kg, increasing to 60 mg/kg, a dose predicted to provide a mean exposure (AUCinf) that does not exceed the mean exposure in Tg2576 mice given 500 mg/kg (AUCTAU=402000 μg*hr/mL). Doses up to 30 mg/kg (0.3, 1, 3, 10, 20, and 30 mg/kg) were generally well tolerated.

Two serious adverse events (SAEs) of symptomatic amyloid related imaging abnormalities-edema (ARIA-E), and one adverse event (AE) of asymptomatic ARIA-E were reported in the 60 mg/kg cohort. Further enrollment into the 60 mg/kg cohort was terminated per study protocol. No deaths or withdrawals due to AEs were reported in the SAD study. Serum exposures of BIIB037 have demonstrated linearity with doses up through 30 mg/kg.

Example 6

A. Phase 1b Clinical Study of BIIB037 in Human AD Subjects

A Phase 1b clinical trial was conducted. The trial was a randomized, blinded, placebo-controlled, ascending dose study of BIIB037 in prodromal to mild AD subjects and positive amyloid scans. The primary endpoint of the trial was safety. Secondary endpoints included assessment of the effect on cerebral amyloid plaque content as measured by 18F-AV-45 PET imaging. Change from baseline in 18F-AV-45 PET signal was assessed in certain brain areas. Exploratory endpoints assessed cognition in the subjects. Subjects received 1, 3, 6, or 10 mg/kg of BIIB037 based on the patient's body weight, or placebo.

B. Pre-Specified Interim Analysis #1

Pre-specified Interim Analysis #1 provided 26 week data for the 1, 3, and 10 mg/kg groups and the placebo group.

The AD subjects were randomized into 4 groups, placebo, those receiving BIIB037 at 1 mg/kg of the patient's body weight, those receiving BIIB037 at 3 mg/kg of body weight, and those receiving BIIB037 at 10 mg/kg of body weight. There were approximately 31 subjects in each group. The average age of the subjects was about 72 years (mean). Apo E4 carriers comprised to 63%, 61%, 66%, and 63%, of the groups, respectively.

The clinical stage of AD in the subjects was assessed. Subjects with prodromal AD comprised to 47%, 32%, 44%, and 41% of the groups, respectively. Subjects with mild AD comprised to 53%, 68%, 56%, and 59% of the groups, respectively.

A static PET acquisition protocol was employed. Tracer was injected into each subject and a single scan was conducted. The tracer was AV45, a PET ligand targeting fibrillar Aβ plaques.

The results of the amyloid PET imaging protocol were expressed as a standard update value ratio, which is a measure of the uptake of the β-amyloid ligand used for PET imaging and corresponds to the amount of β-amyloid present. The standardized uptake value ratio normalizes the PET signal by taking a ratio of a target region over a reference region. In the target region, specific binding and change in binding signal reflect treatment-induced modulation of pharmacology. In the reference region, nonspecific binding indicates no effect of the treatment.

A dose-dependent reduction of amyloid was observed. There was a statistically significant reduction observed at 3 mg/kg and at 10 mg/kg at week 26. The effect appeared to continue to week 54 based on a small subset of subjects. There was no obvious ApoE modification of the observed effects. Greater effects were observed in subjects with higher baseline standard update value ratios.

Safety and tolerability of the treatment were assessed. Adverse events were generally mild or moderate. Headache was the most common adverse event and appeared to be dose-dependent. There were no significant changes in chemistry, hematology, urinalysis, ECGs, or vital signs. Twenty seven subjects exhibited ARIA-E or ARIA-E/H.

Higher incidence of ARIA was observed with higher BIIB037 doses and with Apo E4 carriage. Homozygous and heterozygous ε4-carriers appeared to be at a similar risk for ARIA.

The onset of ARIA-E usually occurred early in the course of treatment. ARIA-E occurred at doses of 1 and 3 mg/kg after 3-5 doses (week 18 or week 10). No case was detected after the fifth dose. ARIA-E occurred at doses of 6 and 10 mg/kg after 2 doses (week 6) and at week 30. Imaging findings generally resolved in 4-12 weeks, indicating that ARIA-E was reversible.

All subjects with ARIA-H events also had ARIA-E events. The incidence of ARIA-E was greater than the incidence of ARIA-H in each of the 3 mg/kg and 10 mg/kg treatment groups. The incidence of each event in the group receiving the 1 mg/kg doses was the same.

C. Pre-Specified Interim Analysis #2

Pre-specified Interim Analysis #2 provided 54 week data for the 1, 3, and 10 mg/kg groups and the placebo group, as well as 26 week data for the 6 mg/kg group.

FIG. 1 shows the mean PET composite standardized uptake ratio values (SUVR) by time point based on observed data for each of the treatment groups. FIG. 1 shows that there was a reduction in amyloid burden in each of the treatment groups receiving antibody BIIB037 from baseline to week 26. There was a further reduction in amyloid burden in each of the treatment groups receiving BIIB037 between week 26 and week 54. The placebo group did not exhibit a corresponding reduction in amyloid burden.

FIG. 1 also shows that the reduction of amyloid burden by administration of BIIB037 was dose-dependent. Higher doses of BIIB037 were accompanied by a greater amyloid reduction in the brain using the amyloid scan. A similar effect was not observed in the placebo group.

Figure 2:
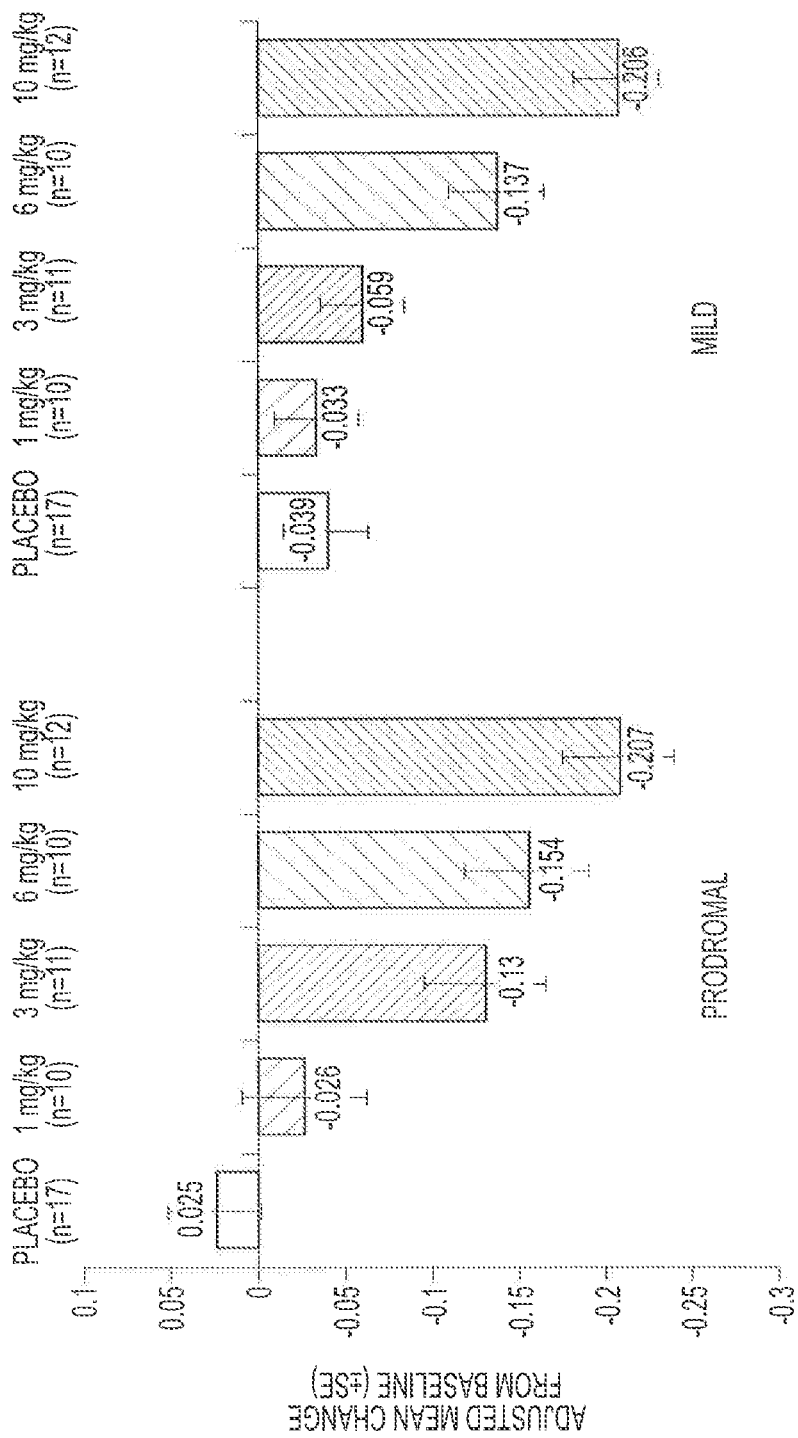
FIG. 2 shows the adjusted mean change from baseline PET composite SUVR of the subjects by baseline clinical stage, namely, prodromal or mild AD.

FIG. 2 shows the adjusted mean change from baseline PET composite SUVR at week 26 by baseline clinical stage, namely, prodromal or mild AD. FIG. 2 is based on observed data. FIG. 2 shows that amyloid reduction was dose-dependent in the amyloid scans.

Figure 3:
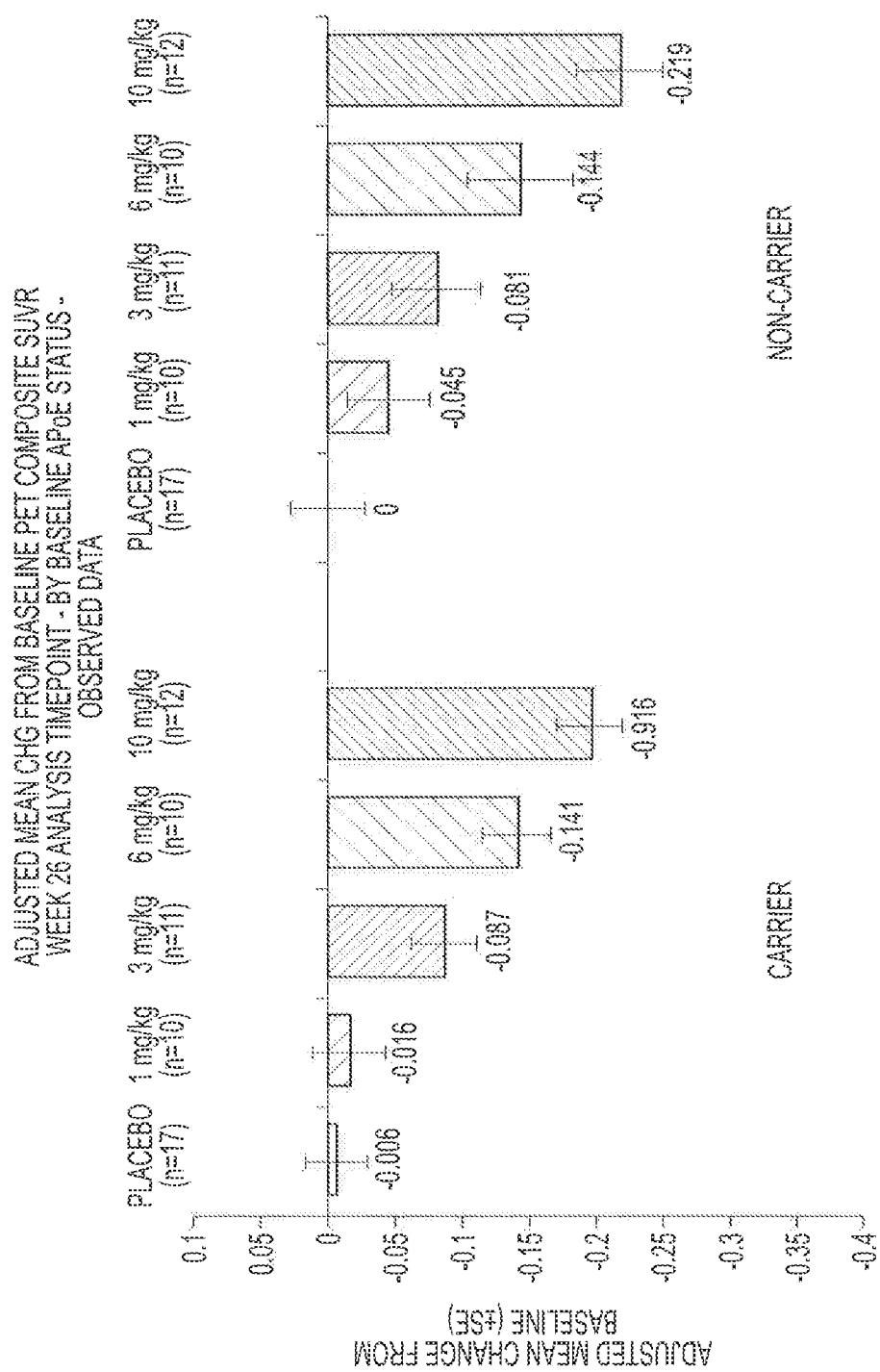
FIG. 3 shows the adjusted mean change from baseline PET composite SUVR by baseline ApoE4 status of the subjects.

FIG. 3 shows the reduction in amyloid burden by ApoE4 status of the subjects. Both the carrier group and the non-carrier group showed a reduction in amyloid burden compared to the placebo. The reduction was dose-dependent in each case.

The incidence of ARIA-E and/or ARIA-H in the study was estimated. The results are shown in FIG. 4. The incidence of ARIA in ApoE4 carriers and ApoE4 non-carriers are also reported in FIG. 4. The incidence was dose-dependent and the ApoE4 carriage dependent at 6 and 10 mg/kg. The onset of ARIA-E was usually early in the course of treatment. ARIA-E was, in general, reversible. ARIA-H was stable. Imaging findings generally resolved in 4-12 weeks.

D. Clinical Assessment of Patient Cognition

Clinical assessments were employed as indicators of changes in the symptoms of Alzheimer's disease in the patients treated. Specifically, changes from baseline were determined on the Clinical Dementia Rating (CDR) Scale and the Mini Mental State Examination (MMSE). The results of these assessments based on observed data are summarized in FIGS. 5 and 6.

Figure 5:
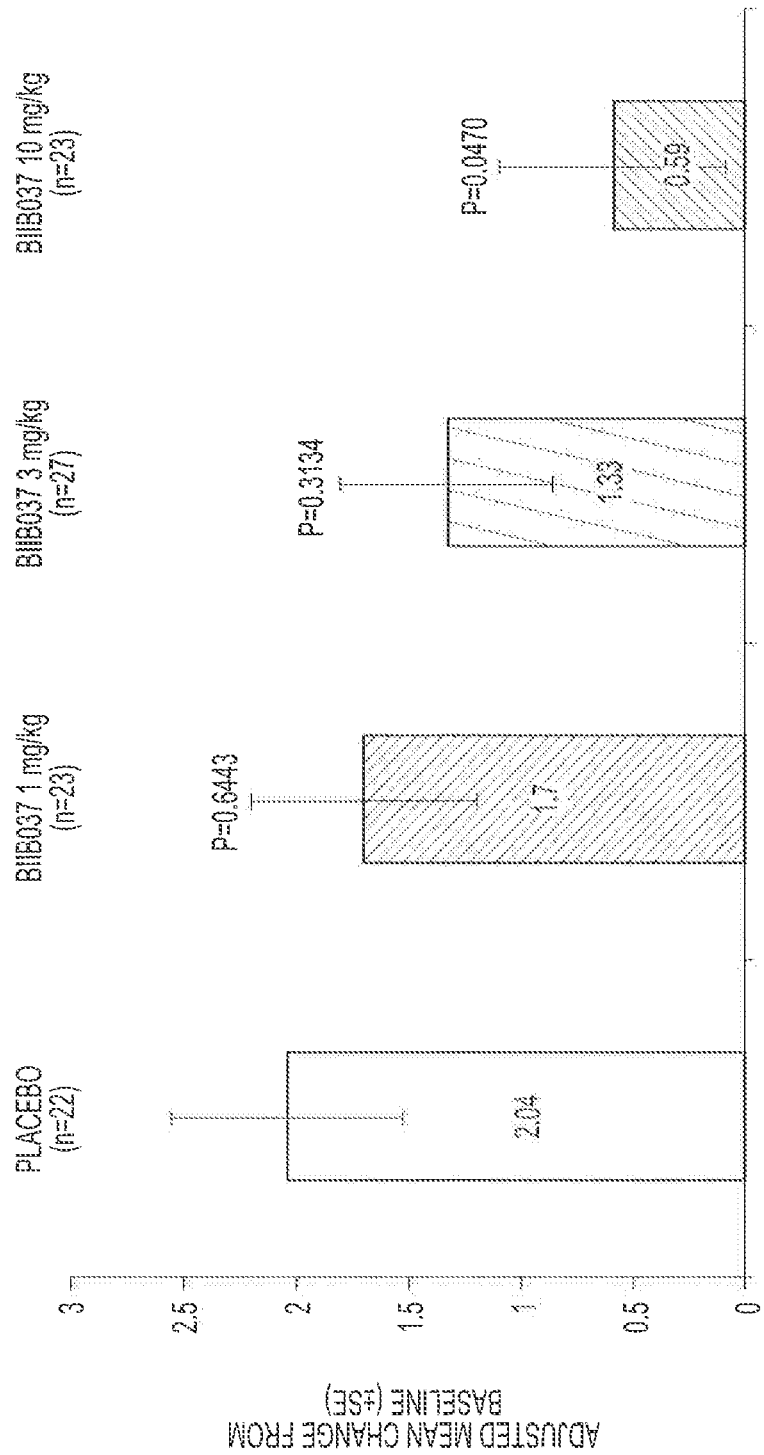
FIG. 5 shows the adjusted mean change from baseline Clinical Dementia Rating Sum of Boxes (CDR-SB) for patients dosed every 4 weeks for 54 weeks with placebo, or 1 mg/kg, 3 mg/kg, or 10 mg/kg of antibody BIIB037.

FIG. 5 shows the adjusted mean change from baseline CDR-SB for patients receiving a placebo compared with patient populations receiving 1 mg/kg, 3 mg/kg, or 10 mg/kg of antibody BIIB037. Measurements were made at week 54 of treatment with the specified doses.

Figure 6:
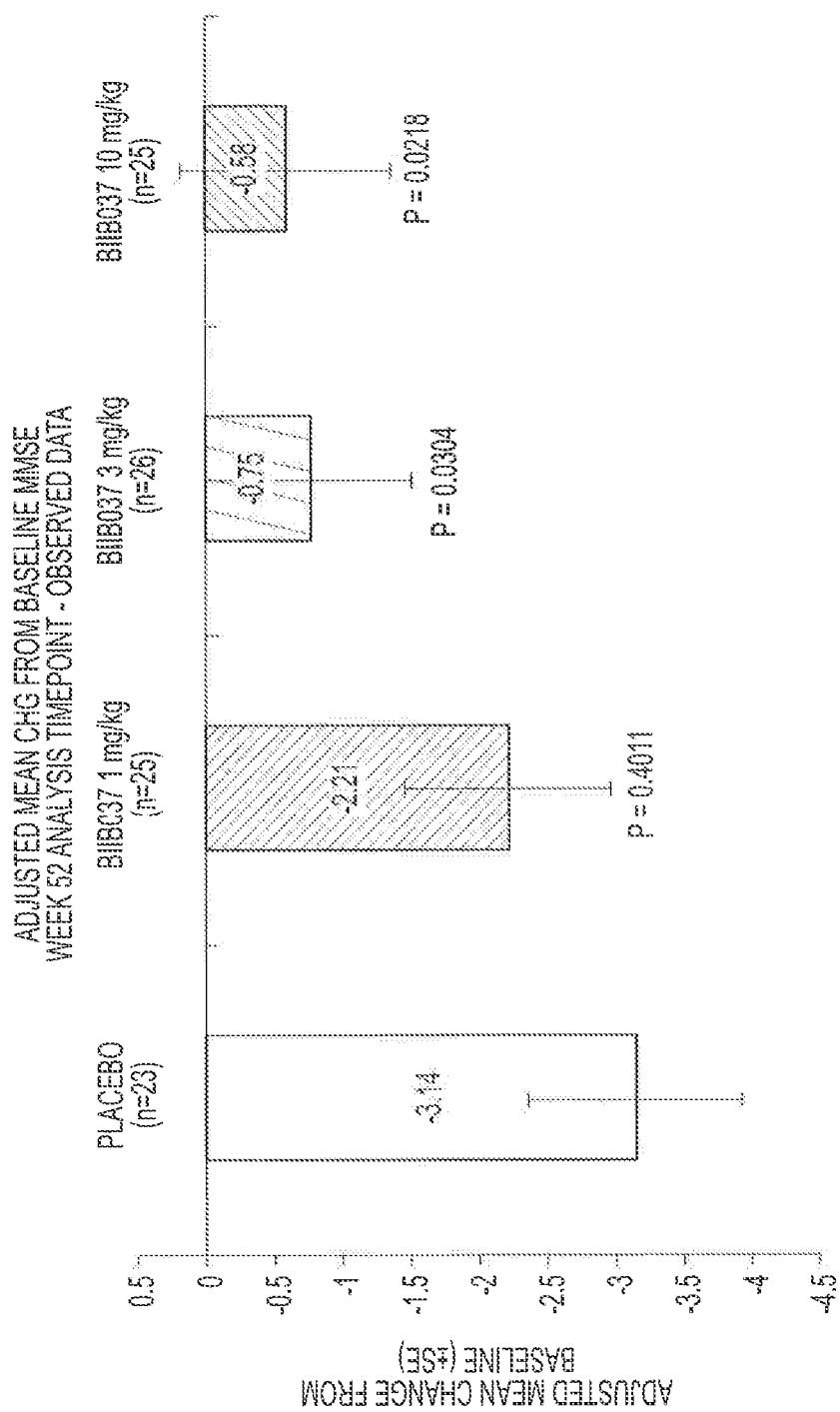
FIG. 6 shows the adjusted mean change from baseline Mini Mental State Examination (MMSE)+standard error (SE) for patients dosed every 4 weeks for 54 weeks with placebo, or 1 mg/kg, 3 mg/kg, or 10 mg/kg of antibody BIIB037.
Figure 7A:
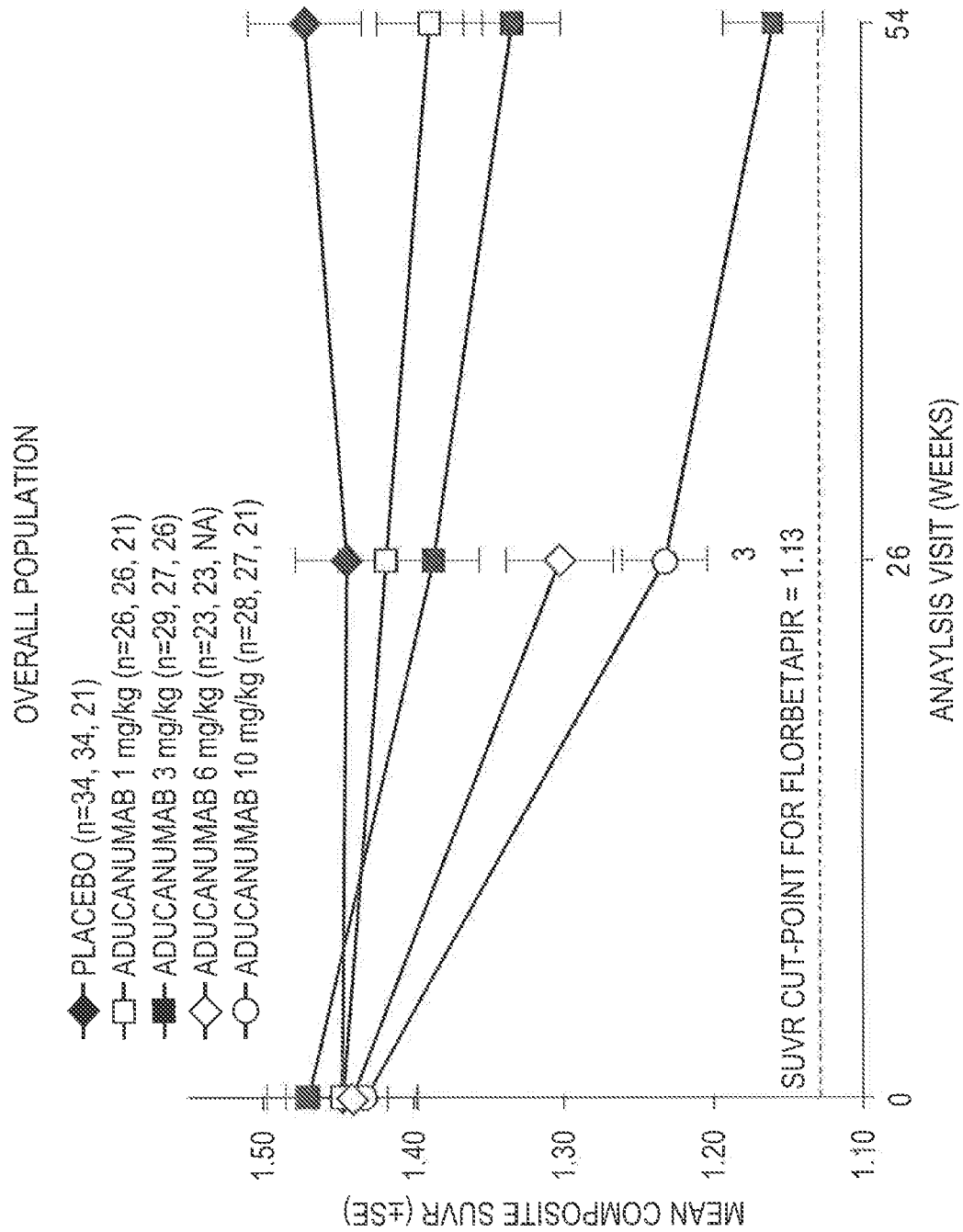
FIGS. 7A-7F show amyloid plaque reduction with aducanumab.
Figure 7B:
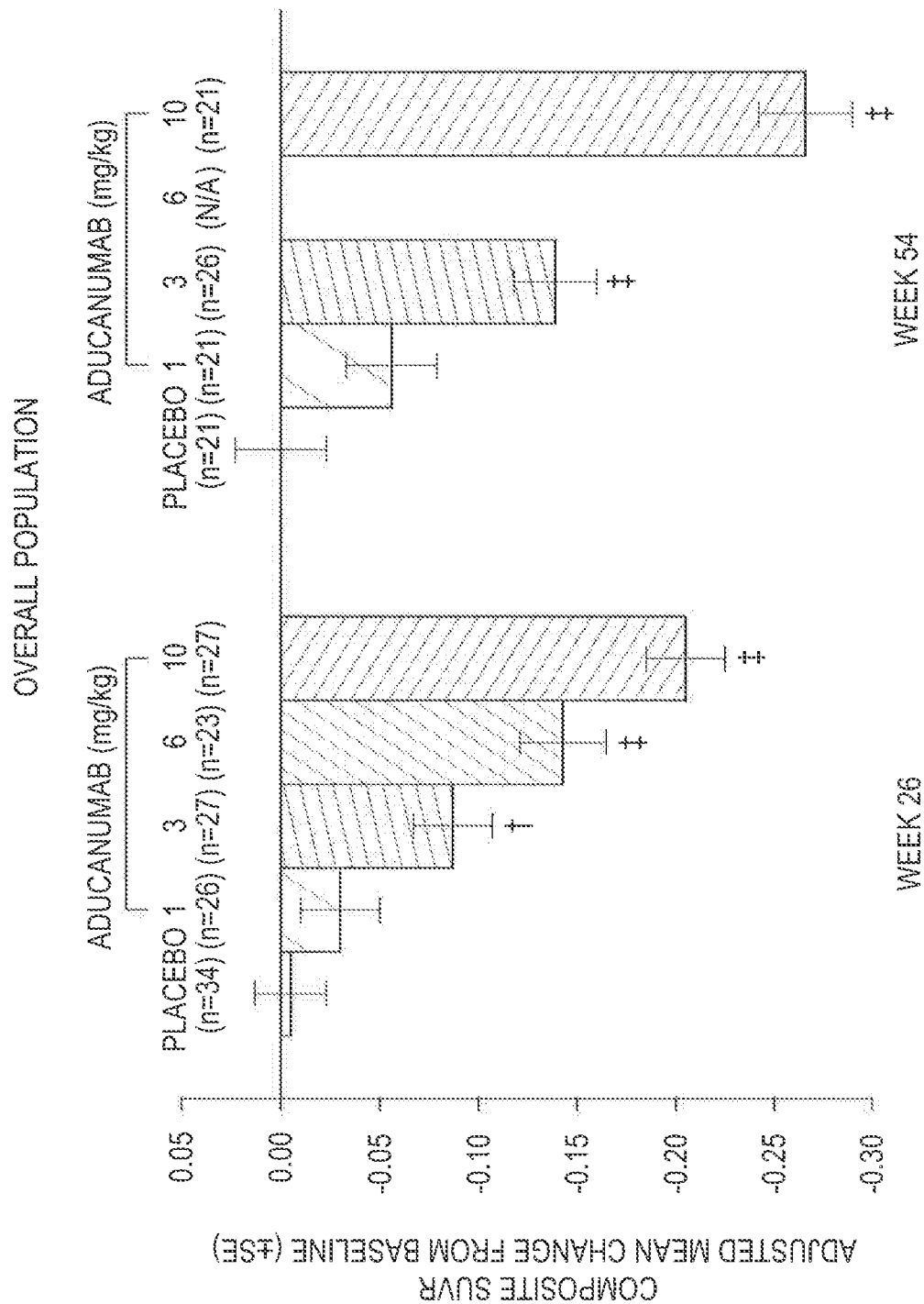
Figure 7C:
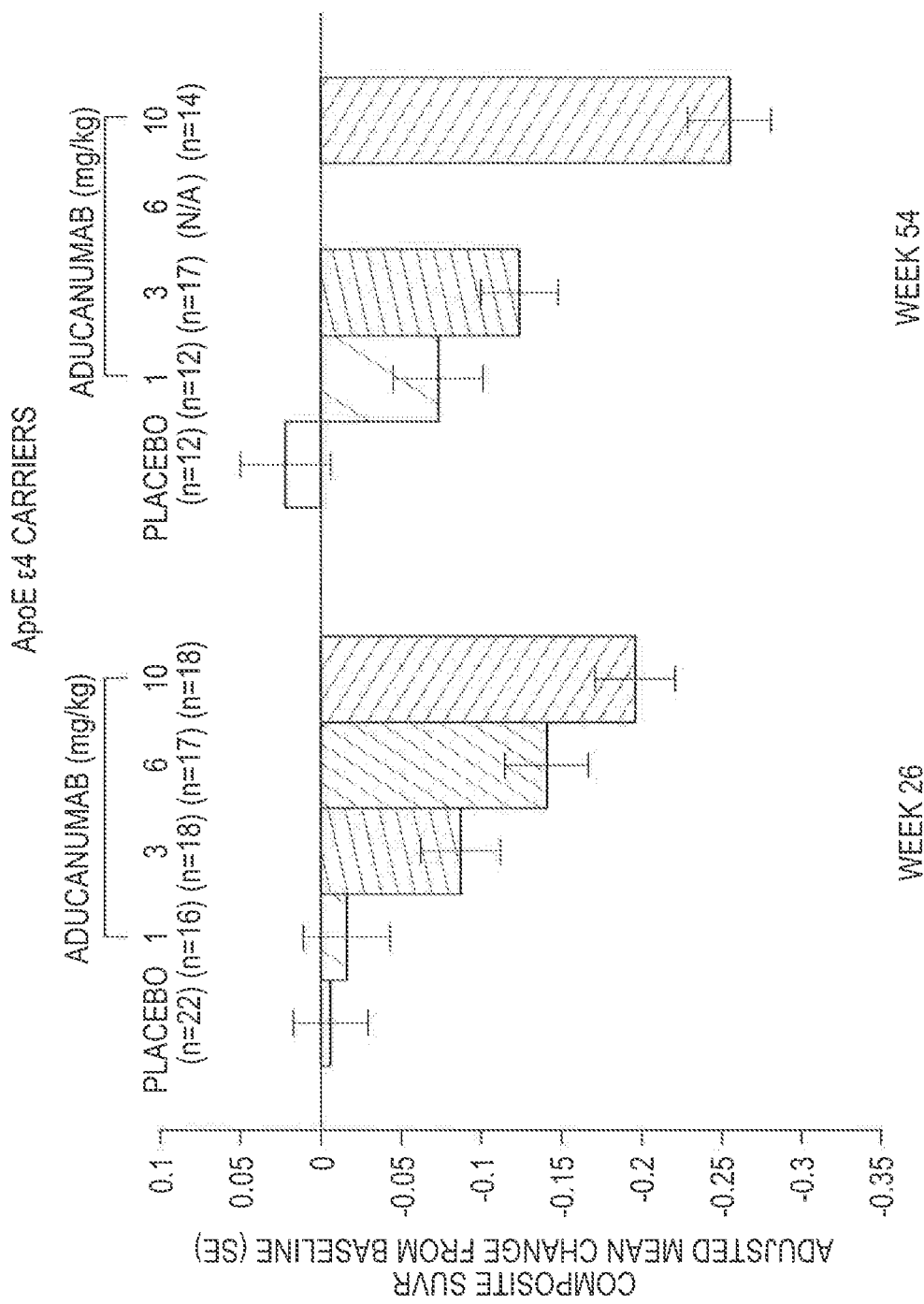
Figure 7D:
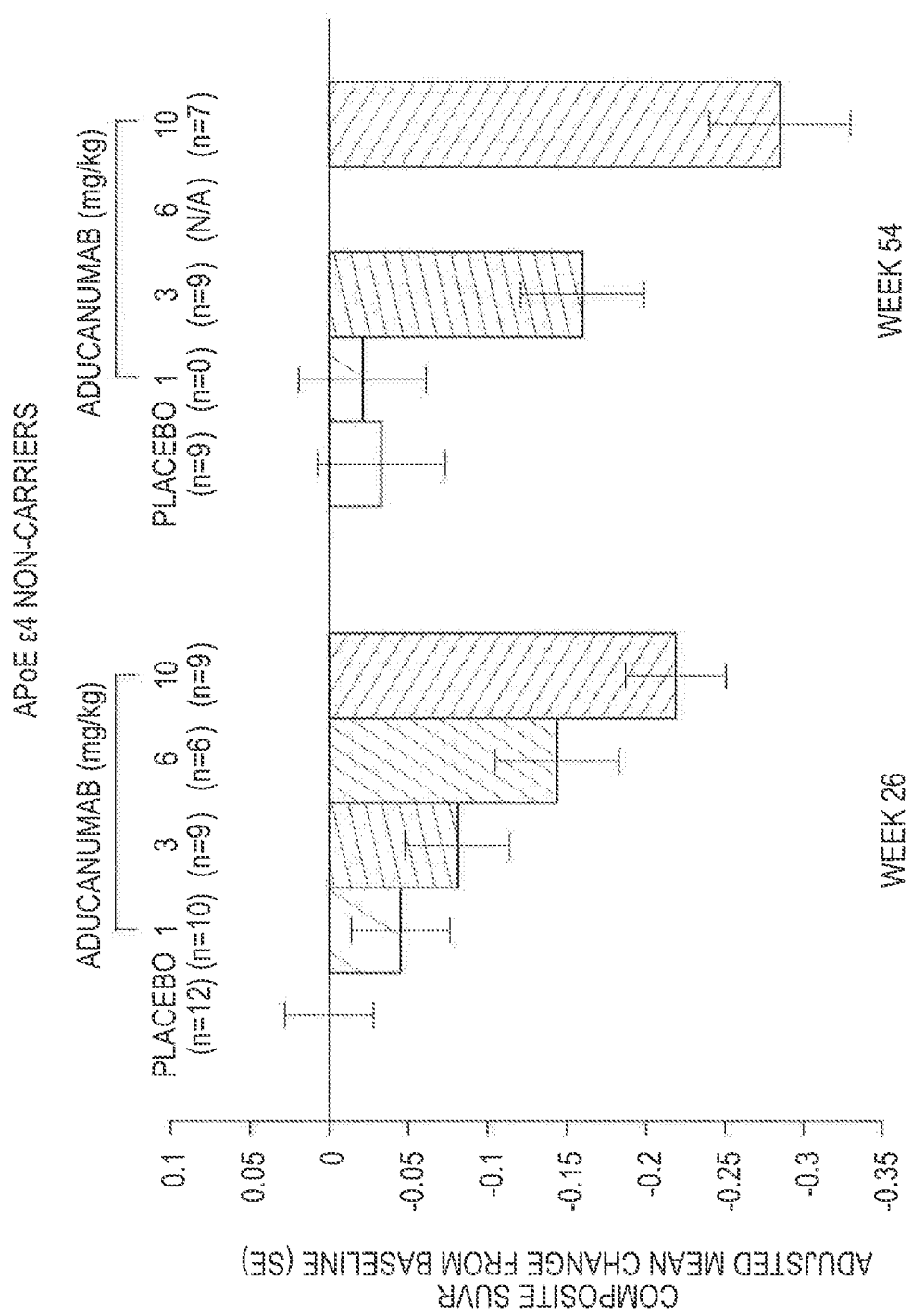
Figure 7E:
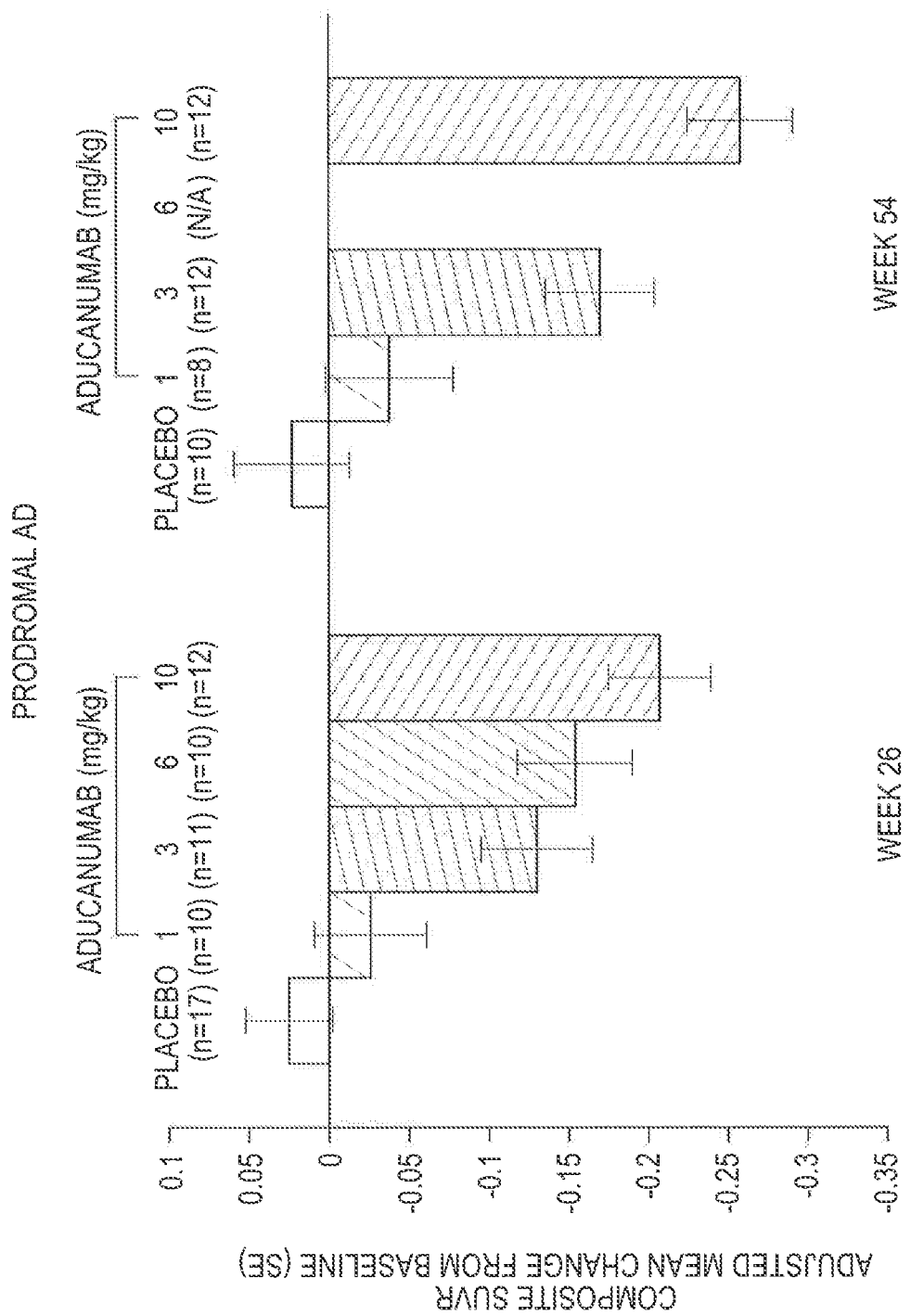
Figure 7F:
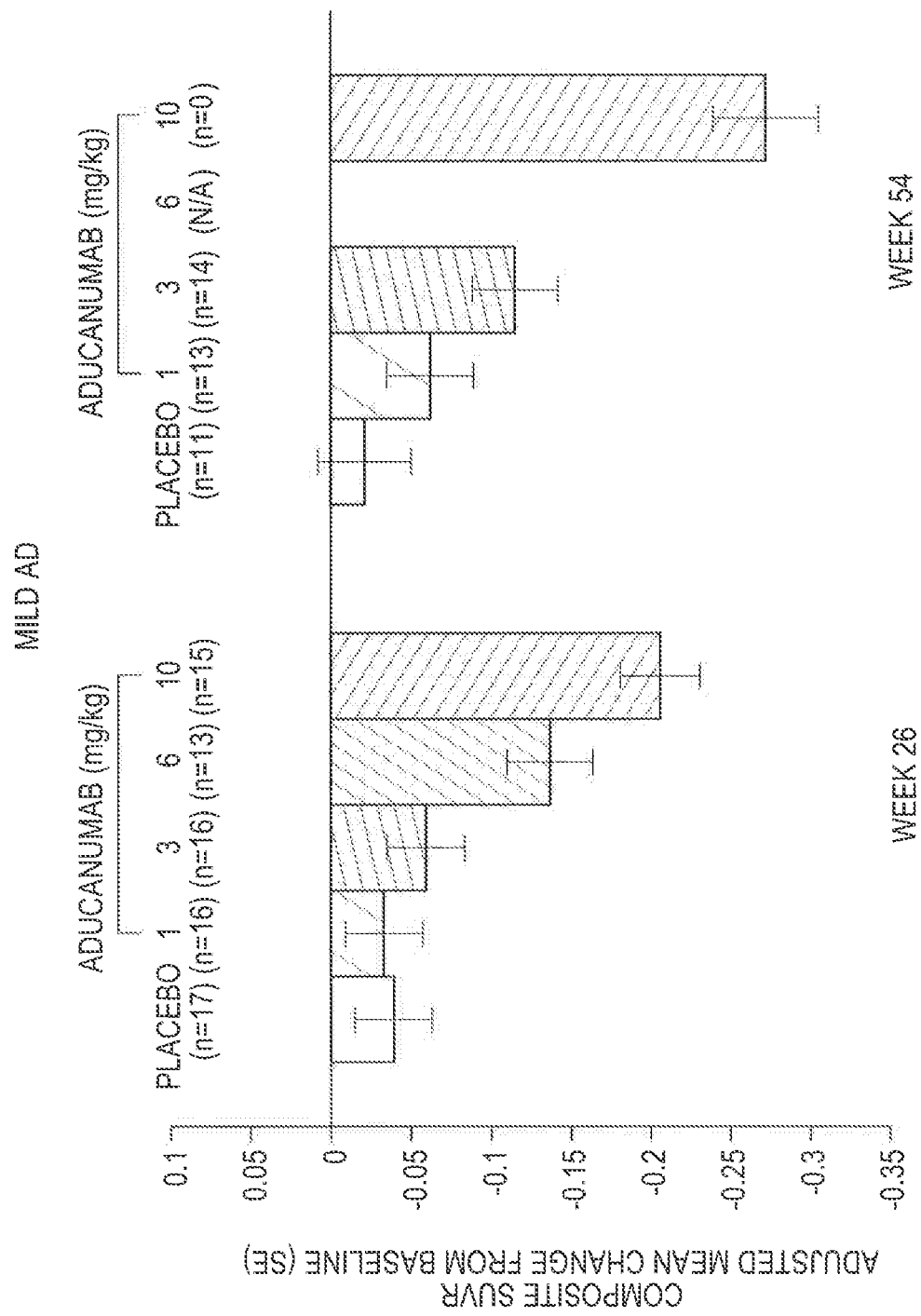

FIG. 6 shows the adjusted mean change from baseline MMSE for patients receiving a placebo compared with patient populations receiving 1 mg/kg, 3 mg/kg, or 10 mg/kg of antibody BIIB037. Measurements were made at week 54 of treatment with the specified doses.

Example 7

Randomized, Double-Blind, Placebo-Controlled, Phase 1b Study of Aducanumab (BIIB037), an Anti-Aβ Monoclonal Antibody, in Patients with Prodromal or Mild Alzheimer's Disease: Interim Results by Disease Stage and ApoE ε4 Status Aducanumab (BIIB037) is a human monoclonal antibody selective for aggregated forms of beta-amyloid (A(3) peptide, including soluble oligomers and insoluble fibrils. A single ascending dose study of aducanumab demonstrated acceptable safety and in patients with mild-to-moderate AD at does up to 30 mg/kg. This Phase 1b study evaluated the safety, tolerability, pharmacrokinetics (PK), and pharmacodynamics of aducanumab in patients with prodromal or mild AD.

The objective was to present interim safety and Aβ removal (change in florbetapir [18-AV-45] positron emission tomography [PET] results) with aducanumab by disease stage and ApoE ε4 status.

Study Design

PRIME is a multicenter, randomized, double-blind, placebo-controlled, multiple-dose study [NCT01677572].

Patients were aged 50-90 years, had stable concomitant medications, had a Mini-Mental State Examination (MMSE) score ≥20 and met clinical and radiologic criteria as follows:

Prodromal AD: MMSE 24-30 spontaneous memory complaint; total free recall score ≤27 of the Free and Cued Selective Reminding Test; a global Clinical Dementia Rating (CDR) score of 0.5; absence of significant levels of impairment in other cognitive domains; essentially preserved activities of daily living and absence of dementia; had a positive florbetapir PET scan by visual assessment.

Mild AD: MMSE 20-26; global CDR 0.5 or 1.0; meeting National Institute on Aging and Alzheimer's Association core clinical criteria for probable AD; had a positive florbetapir PET scan by visual assessment.

Figure 14:
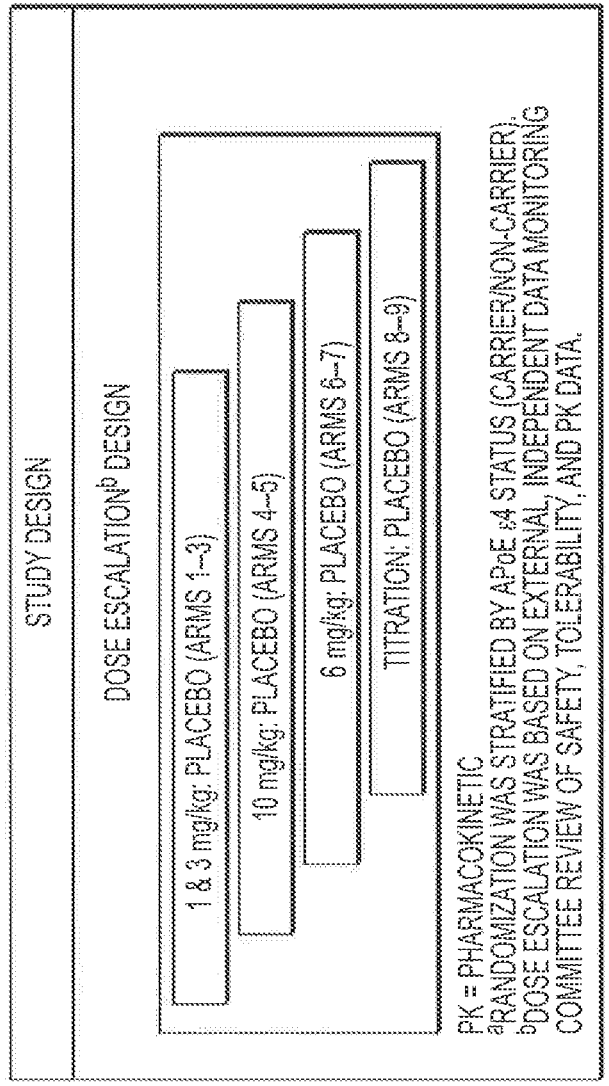
FIG. 14 depicts the study design for PRIME, a multi-center, randomized, double-blind, placebo-controlled, multidose-study. Patients (planned N=188) were randomized to 1 of 9 treatment arms (target enrollment: n=30 per active treatment arm) in a staggered, ascending dose design at a ratio of 3:1 active vs. placebo.
Figure 16:
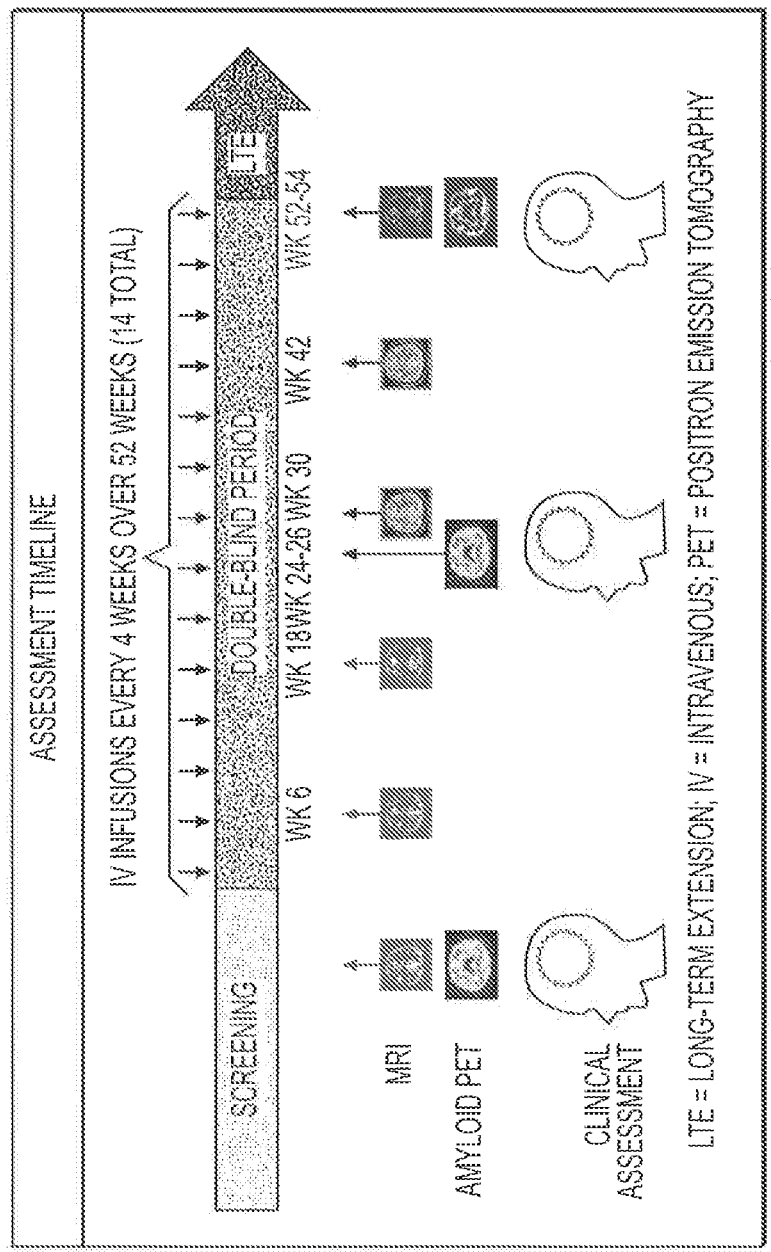
FIG. 16 provides the PRIME assessment timeline. Data were analyzed to Week 54 for the 1, 3, and 10 mg/kg arms and to Week 30 for the 6 mg/kg arm.

The PRIME study design is shown in FIG. 14. Patients (planned N=188) were randomized to 1 of 9 treatment arms (target enrollment: n=30 per active treatment arm) in a staggered, ascending dose design at a ratio of 3:1 active vs. placebo. Primary and secondary endpoints are presented in FIG. 15. ThePRIME assessment timeline is shown in FIG. 16. PRIME is ongoing. For interim analysis, data were analyzed to Week 54 for the 1, 3, and 10 mg/kg arms and to Week 30 for the 6 mg/kg arm.

Patients

Figure 17:
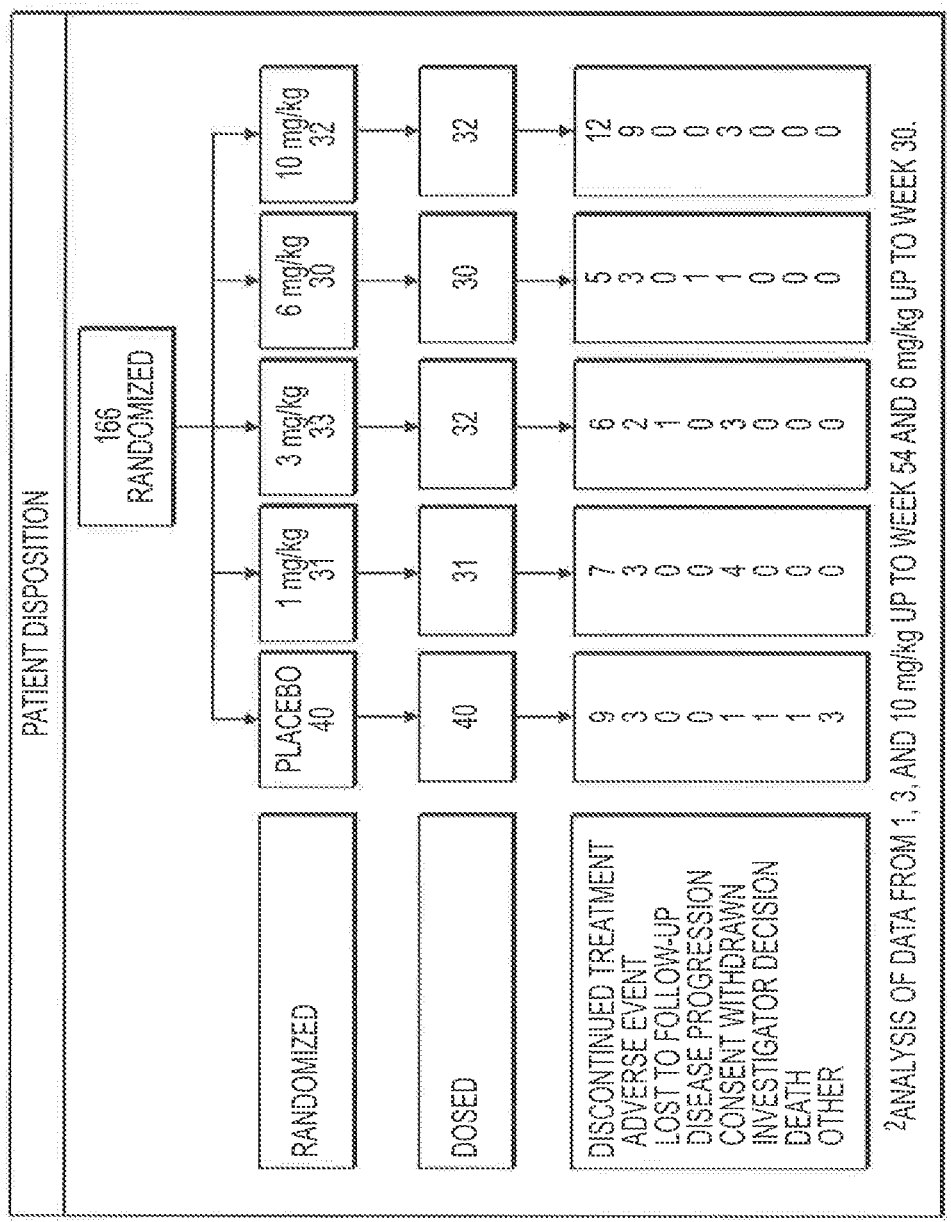
FIG. 17 depicts patient disposition in the PRIME study. Of the 166 patients randomized, 165 were dosed; 107 (65%) were ApoE ε4 carriers, and 68 (41%) had prodromal AD.

Of the 166 patients randomized, 165 were dosed; 107 (65%) were ApoE ε4 carriers, and 68 (41%) had prodromal AD. Patient disposition is shown in FIG. 17. Baseline demographic and disease characteristics were generally well balanced across treatment groups as shown in FIG. 18.

Safety

Adverse events (AE) were reported in 84%-98% of patients across treatment groups. The most common AE and serious AE (SAE) were amyloid-related imaging abnormalities (ARIA; based on MRI) (Table 9); other AEs/SAES were consistent with the patient population. FIG. 19 provides a summary of ARIA findings and patient disposition following E ARIA-E.

Three deaths were reported (2 with placebo, 1 with aducanumab 10 mg/kg); none were considered treatment related (2 occurred after study discontinuation).

Incidence of isolated ARIA-edema (ARIA-E) was dose- and ApoE ε4-status-dependent (FIG. 19):

Overall incidence of ARIA-E among ApoE ε4 carriers was 5%, 5%, 43%, and 55% for 1, 3, 6, and 10 mg/kg aducanumab, respectively, versus 0% for placebo.

Corresponding incidence among ApoE ε4 non-carriers was 0%, 9%, 11%, and 17% versus 0%.

Incidence of isolated ARIA-microhemorrhange/hemosiderosis (ARIA-H) was similar across doses and ApoE ε4 status (data not shown).

Based on small sample sizes, there was no apparent difference in incidence of ARIA-E between subjects with prodromal or mild AD when accounting for ApoE ε4 status (FIG. 19).

Most (92%) ARIA-E events were observed within the first 5 doses; 65% of ARIA-E events were asymptomatic.

When present, symptoms typically resolved within 4 weeks.

Mill findings typically solved within 4-12 weeks.

The majority of patients (54%) who developed ARIA-E continued treatment (93% of those who continued did so at a reduced dose); no patients developed recurrent ARIA-E. Treatment discontinuations in patients with ARIA-E were consistent across mild and prodromal subgroups (data not shown).

There were no significant changes in chemistry, hematology, urinalysis, electrocardiogram, or vital signs.

Brain Aβ Plaque Reduction

Brain Aβ plaque reduction was evaluated by composite SUVR from a volume of 6 regions; frontal, parietal, lateral temporal, sensorimotor, anterior cingulate, and posterior cingulate.

Dose- and time-dependent reductions in brain Aβ plaque (evidenced by SUVR reduction) at weeks 26 and 54 were generally consistent across mild and prodromal AD subgroups and across ApoE ε4 carriers and non-carriers within the doses tested as shown in FIG. 7.

Clinical Endpoints

Figure 8:
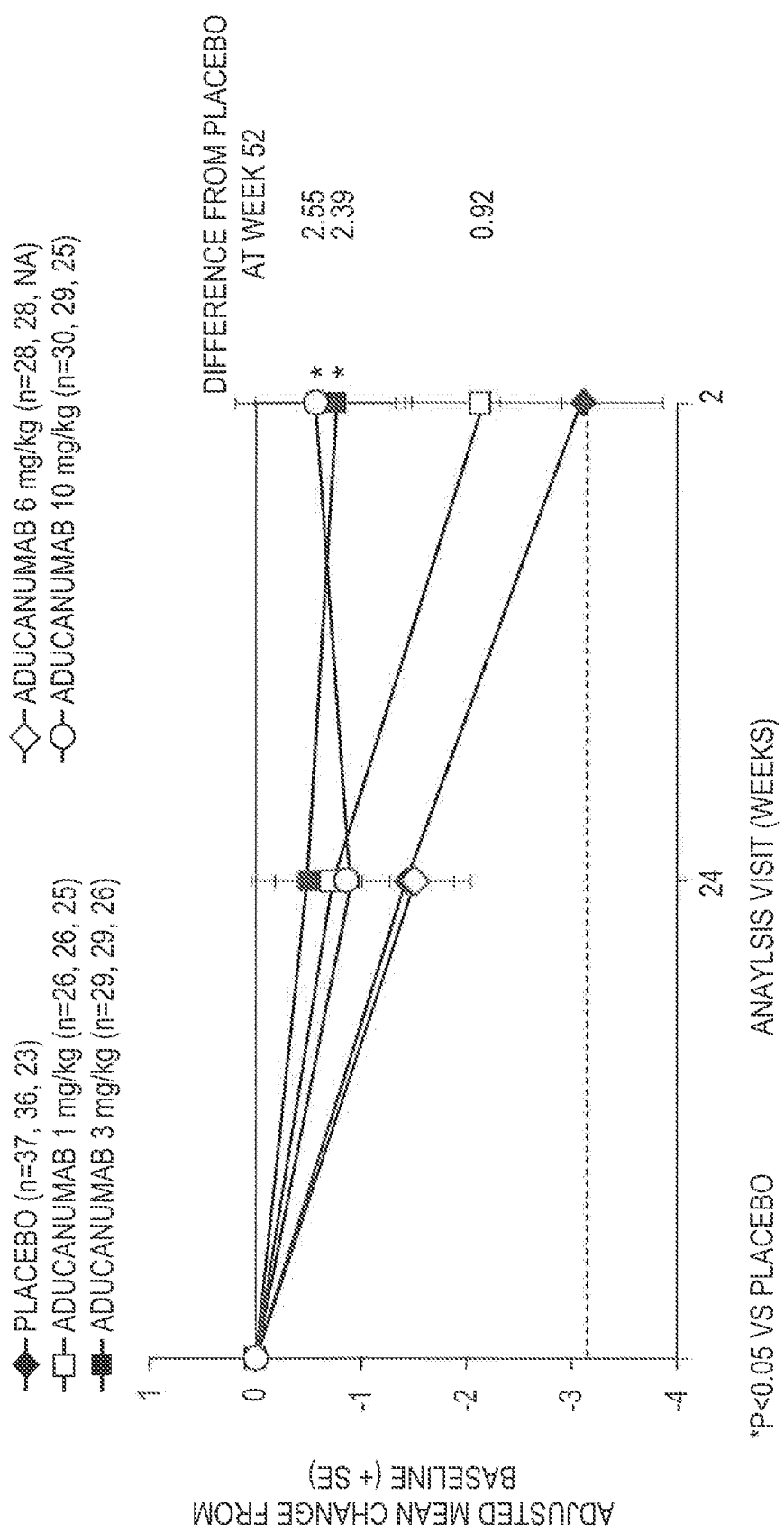
FIG. 8 shows the effect of aducanumab on MMSE.
Figure 9:
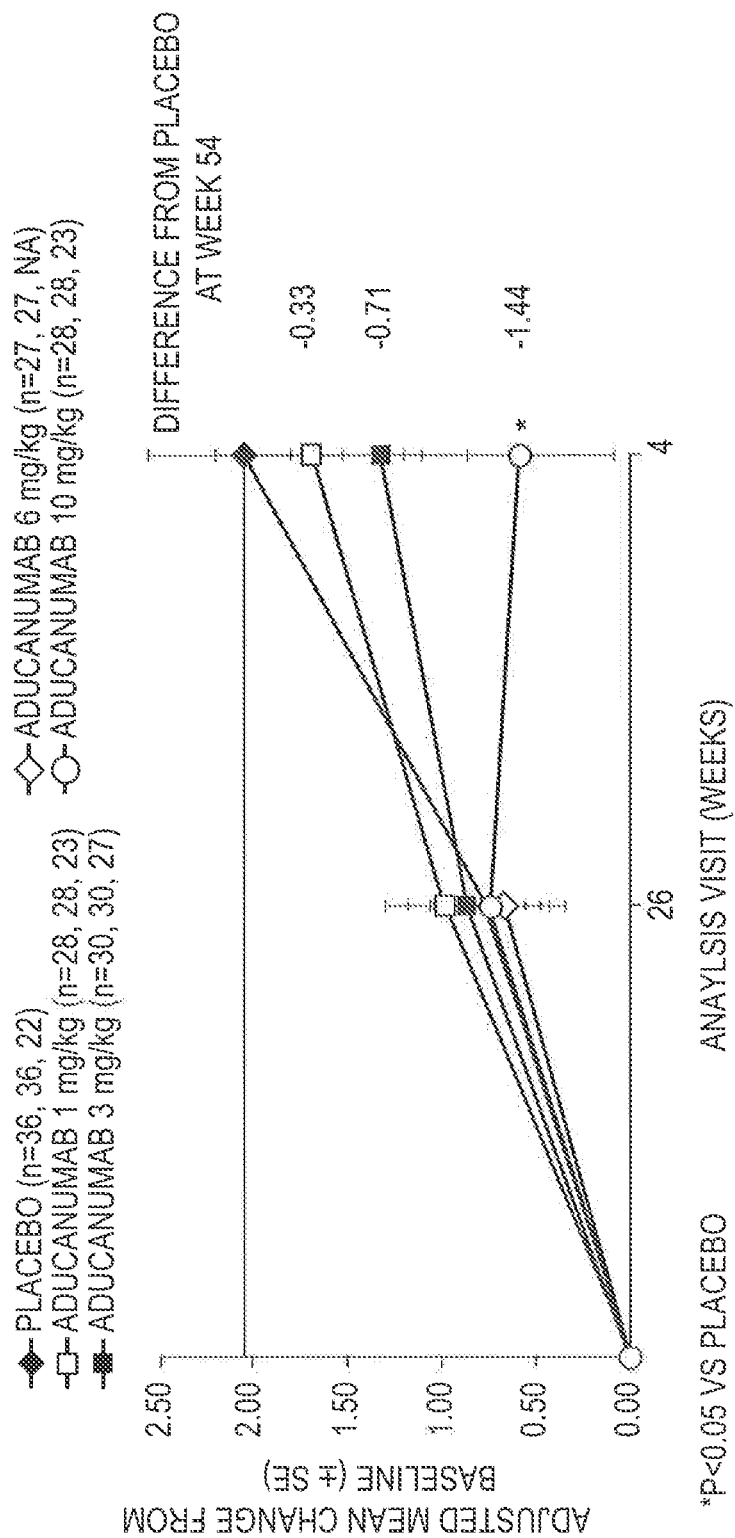
FIG. 9 shows the effect of aducanumab on CDR-SB.

There was statistically significant dose-dependent slowing of decline on the exploratory endpoints, MMSE (FIG. 8) and CDR-sb (FIG. 9) at 1 year.

Conclusions

There was a significant dose-and time-dependent reduction of brain Aβ plaques as measured by PET Imaging versus placebo. This effect was evident at 6 months and 1 year of treatment.

The pattern of the aducanumab effect versus placebo on Aβ plaque reduction was generally consistent across disease stage and ApoE ε4 status.

A statistically significant dose-dependent slowing of decline on MMSE and CDR-sb was observed at 1 year.

Aducanumab demonstrated an acceptable safety profile over 54 weeks. ARIA was the main safety and tolerability finding and was able to be monitored and managed. The incidence of ARIA was dose- and ApoE-ε4-status-dependent. ARIA was usually observed early in the course of treatment and was asymptomatic or with mild, transient symptoms.

Interim Analysis #3

Interim Analysis #3 includes data to 54 weeks for the 6 mg/kg arm and the corresponding placebo arm (which is incorporated into the pooled placebo population for the analysis).

Brain Aβ Plaque Reduction

Figure 11:
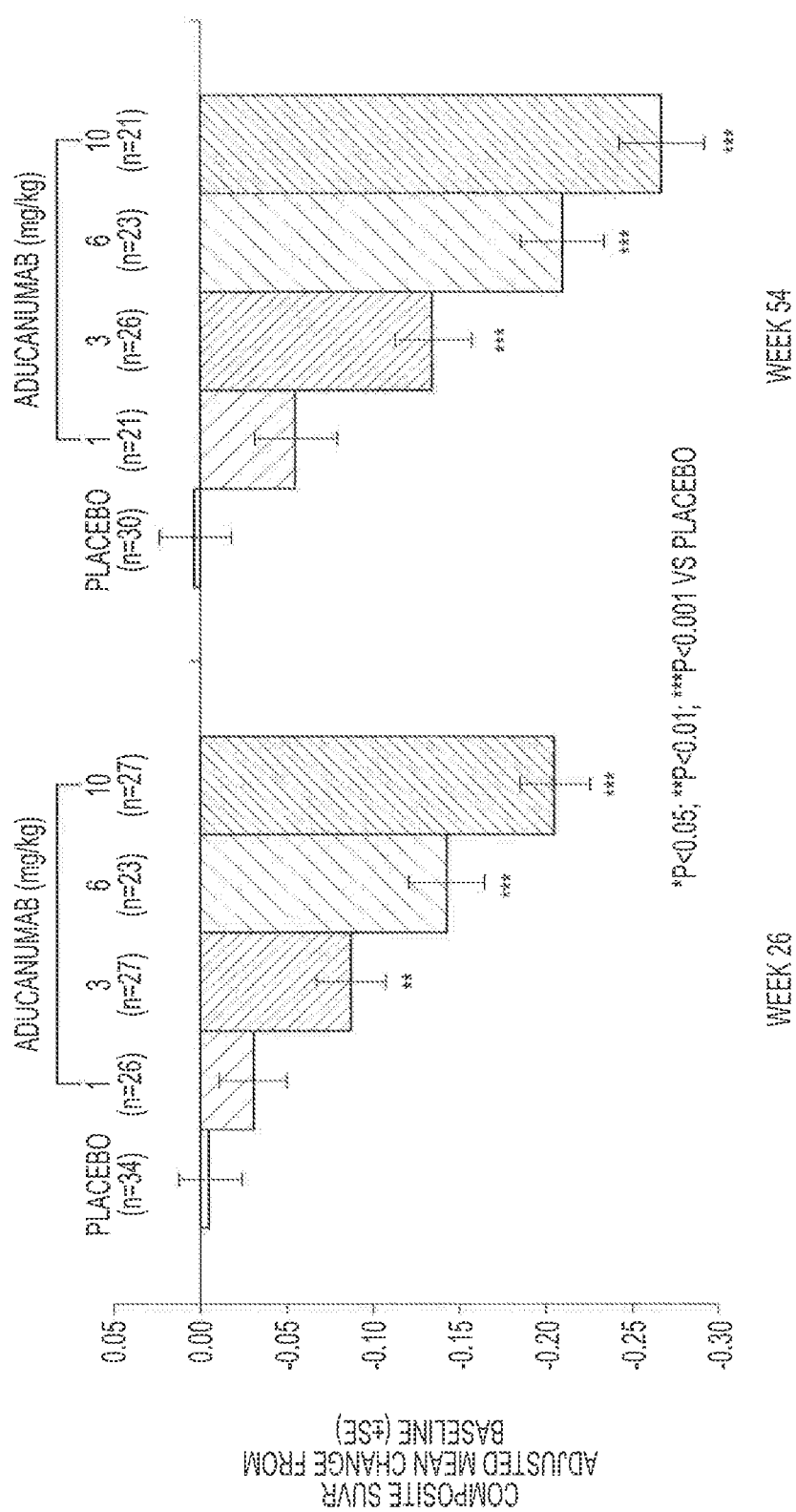
FIG. 11 demonstrates the ability of aducanumab to reduce amyloid plaque.

Brain Aβ plaque reduction was evaluated by composite SUVR from a volume of 6 regions; frontal, parietal, lateral temporal, sensorimotor, anterior cingulate, and posterior cingulate. As shown in FIG. 11, there was a dose-dependent reduction in brain Aβ plaque (evidenced by SUVR reduction) at week 54.

Clinical Endpoints

Figure 12:
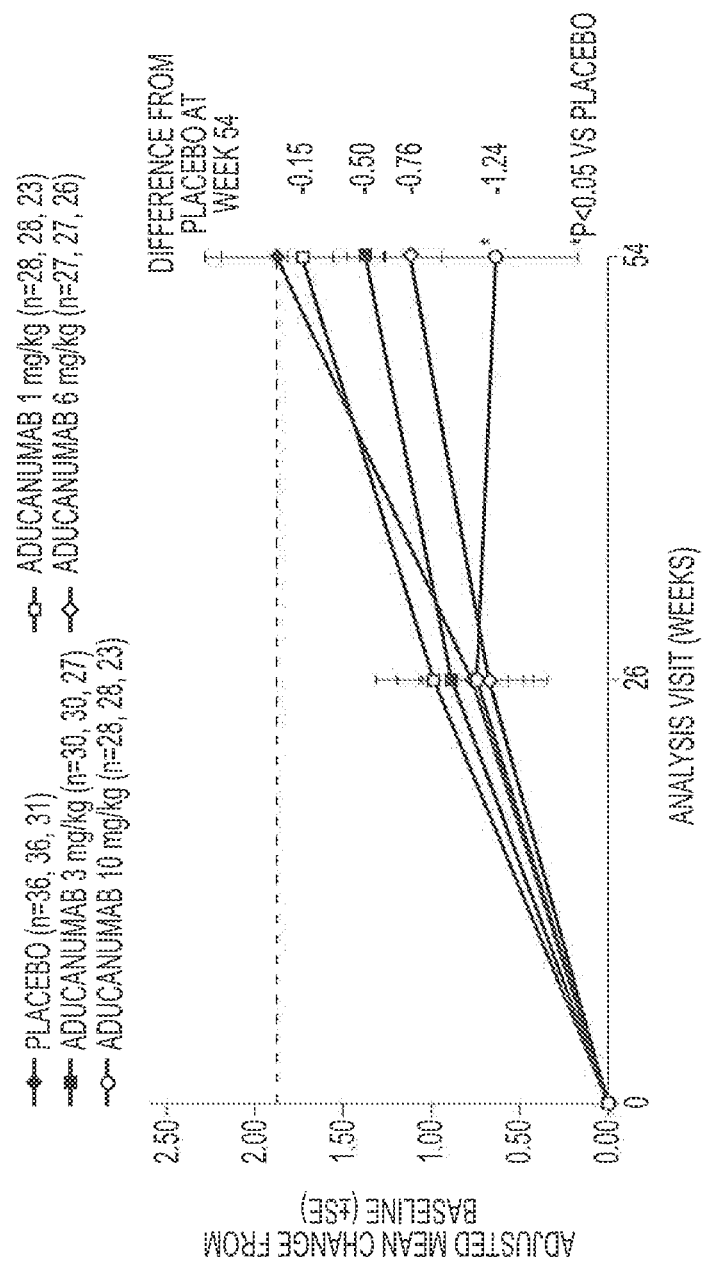
FIG. 12 demonstrates a slowing of decline on CDR-SB with aducanumab.
Figure 13:
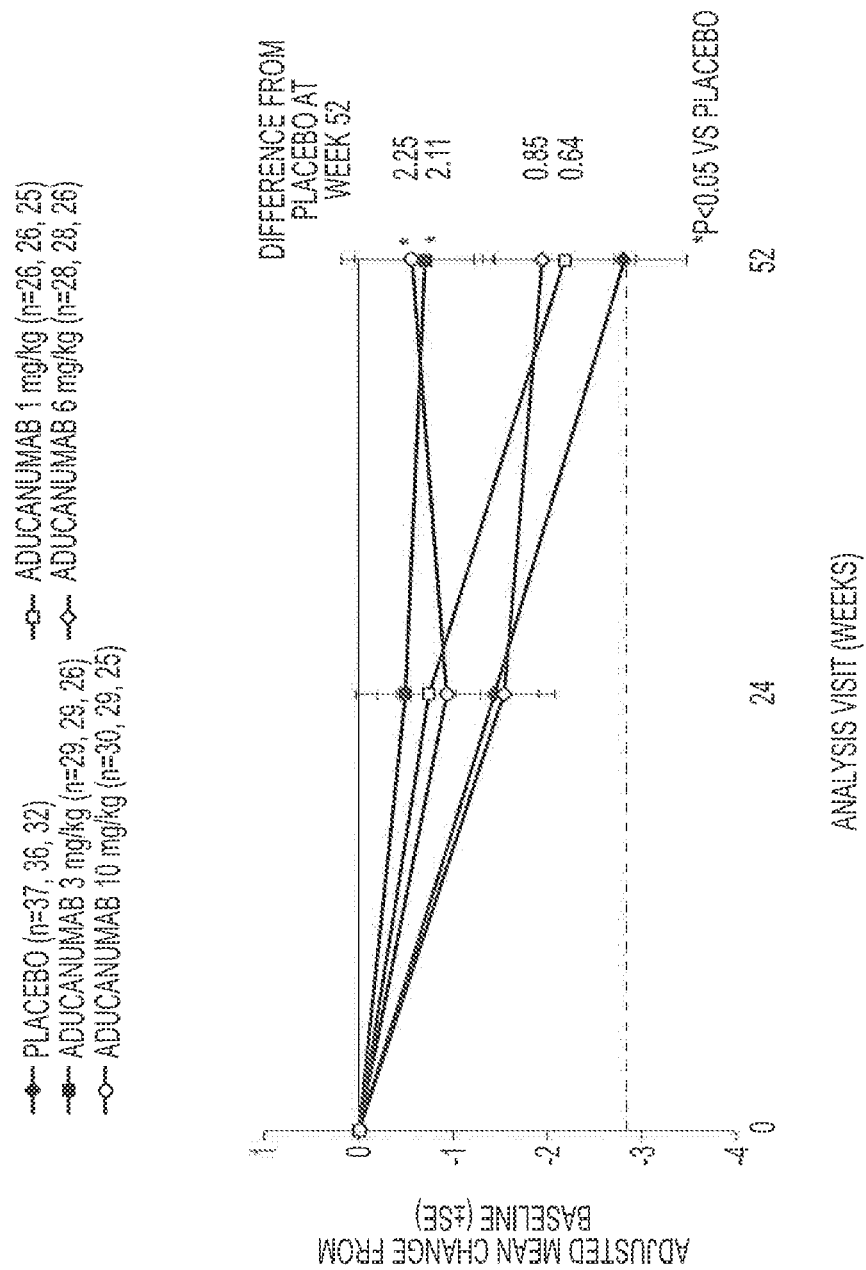
FIG. 13 demonstrates a slowing of decline on MMSE with aducanumab.

There was statistically significant dose-dependent slowing of decline on the exploratory endpoints, MMSE (FIG. 13) and CDR-sb (FIG. 12) at 1 year.

Example 8

Phase 3 Multicenter, Randomized, Double-Blind, Placebo-Controlled, Parallel-Group Study to Evaluate the Efficacy and Safety of Aducanumab (BIIB037) in Subjects with Early Alzheimer's Disease A study is conducted to assess the efficacy and safety of aducanumab compared with placebo in subjects with early AD including subjects with mild cognitive impairment (MCI) due to AD and a subset of mild AD.

The dosing regimen selected for this study was based on the observed PK and PD relationship for removal of brain amyloid and effect on CDR-SB and MMSE, safety, tolerability, and PD data.

The dose- and time-dependent reduction of brain amyloid burden observed with aducanumab treatment was statistically significant at doses of 3, 6 and 10 mg/kg after 6 months of dosing and at 3 and 10 mg/kg after 12 months of dosing. The effect on mean decrease from baseline in CDR-SB after 12 months of dosing was observed at both 3 and 10 mg/kg, with statistical significance achieved at 10 mg/kg. The effect on mean decrease from baseline in MMSE score was statistically significant at 3 and 10 mg/kg. These data indicate that 3 mg/kg is an acceptable dose; however, given the dose-dependent nature of these observations, the use of higher doses (6 and 10 mg/kg) offers greater benefit at acceptable risk.

ARIA has been identified as an event that may occur with anti-amyloid targeting drug candidates and is considered an event of special interest. To date, the incidence of ARIA has been observed to be both dose and ApoE ε4 carriage dependent, especially at the highest doses.

To maximize the dose-dependent amyloid reduction and effect on CDR-SB and MMSE that have been observed with doses of 3 mg/kg and higher while maintaining ARIA incidence, severity, and related discontinuation rate within acceptable levels, a titration regimen is employed.

Given the tolerability and apparent efficacy of aducanumab, the doses using a titration regimen are 3 and 6 mg/kg for ApoE ε4 carriers, and 6 and 10 mg/kg for ApoE ε4 non-carriers. Titration starts at 1 mg/kg and escalates to 3, 6 and 10 mg/kg as detailed below.

Dosing Scheme

Placebo-Controlled Period

Doses are administered approximately 4 weeks apart, over approximately 76 weeks (a total of 20 doses). Based upon their ApoE ε4 carrier status, subjects are assigned to 1 of 3 treatment groups (450 subjects each) in a 1:1:1 ratio (aducanumab low dose:aducanumab high dose:placebo) as follows (see Table 4 and FIG. 10):

ApoE ε4 Carrier
Low dose (3 mg/kg)
1 mg/kg for the first 2 doses, 3 mg/kg thereafter
High dose (6 mg/kg)
1 mg/kg for the first 2 doses, 3 mg/kg for the next 4 doses, and 6 mg/kg thereafter
Placebo
Saline infusion
ApoE ε4 Non-Carrier
Low dose (6 mg/kg)
1 mg/kg for the first 2 doses, 3 mg/kg for the next 4 doses, and 6 mg/kg thereafter
High dose (10 mg/kg)
1 mg/kg for the first 2 doses, 3 mg/kg for the next 2 doses, 6 mg/kg for the next 2 doses, and 10 mg/kg thereafter
Placebo
Saline infusion

TABLE 4

Dosing Scheme for Aducanumab by Regimen

| Regimen | | Dose (Month) | | | | | | |
|---|---|---|---|---|---|---|---|---|
| | | 1 | 2 | 3 | 4 | 5 | 6 | 7 to 20 |
| | | Dose (mgkg) | | | | | | |
| ApoE ε4 (+) | Low Dose | 1 | 1 | 3 | 3 | 3 | 3 | 3 |
| | High Dose | 1 | 1 | 3 | 3 | 3 | 3 | 6 |
| | Placebo | | | | saline | | | |
| ApoE ε4 (−) | Low Dose | 1 | 1 | 3 | 3 | 3 | 3 | 6 |
| | High Dose | 1 | 1 | 3 | 3 | 6 | 6 | 10 |
| | Placebo | | | | saline | | | |

Dosing Scheme Modification

The dosing scheme can be modified in the following circumstances:

Safety and tolerability of the high dose
If any of the high doses (10 mg/kg in ApoE ε4 non-carriers and 6 mg/kg in ApoE ε4 carriers) is not acceptable, enrollment for the high dose group(s) can be terminated and subjects not replaced. Subjects who have already been randomized to the discontinued dose are down-dosed to the next available dose according to their ApoE ε4 carrier status.
Titration
If titration is not beneficial, it is eliminated, and subsequently subjects who are ApoE ε4 carriers receive a fixed dose of 3 or 6 mg/kg and non-carriers can receive 6 or 10 mg/kg.

Long-Term Extension (LTE)

Subjects who received aducanumab in the placebo-controlled period and who enter the LTE continue to receive the same dose of aducanumab that they were on at the end of the placebo-controlled period. Subjects are dosed using the same regimen described for the placebo-controlled period (see Table 4 and FIG. 10). Modifications to the dosing scheme (i.e. termination of high dose groups and replacement of titration with fixed dosing are implemented in the LTE.

The efficacy of monthly doses of the aducanumab in slowing cognitive and functional impairment is measured by changes in the CDR-SB score.

A secondary measure is to assess the effect of monthly doses of aducanumab on clinical progression as measured by the MMSE. The endpoint that relates to this measure is change from baseline in MMSE score at Week 78.

Another secondary measure is to assess the effect of monthly doses of aducanumab on clinical progression as measured by ADAS-Cog 13. The endpoint that relates to this measure is change from the baseline in ADAS-Cog 13 score at Week 78.

Another secondary measure is to assess the effect of monthly doses of aducanumab on clinical progression as measured by ADCS-ADL-MCI. The endpoint that relates to this measure is change from baseline in ADCS-ADL-MCI score at Week 78.

REFERENCES

Albert M S, et al., The diagnosis of mild cognitive impairment due to Alzheimer's disease: recommendations from the National Inst. on Aging-Alzheimer's Association workgroups on diagnostic guidelines for Alzheimer's disease. Alzheimer's & Dement 2011; 7:270-9.

Alzheimer's Association. 2010 Alzheimer's disease facts and figures. Alzheimers Dement. 2010 March; 6(2):158-94.

Alzheimer's Disease International. World Alzheimer Report 2010: The global economic impact of dementia. London: Alzheimer's Disease International 2010.

Amieva H, Le Goff M, Millet X, et al. Prodromal Alzheimer's disease: successive emergence of the clinical symptoms. Ann Neurol. 2008; 64(5):492-8.

Birks J. Cholinesterase inhibitors for Alzheimer's disease. Cochrane Database Syst Rev. 2006(1):1-94. Art. No.: CD005593. DOI: 10.1002/14651858.CD005593.

Black R S, Sperling R A, Safirstein B, Motter R N, Pallay A, Nichols A, et al. A single ascending dose study of bapineuzumab in patients with Alzheimer disease. Alzheimer Dis Assoc Disord. 2010 April-June; 24(2):198-203. [PMC free article] [PubMed]

Clark C M, Schneider J A, Bedell B J et al. Use of florbetapir-PET for imaging β-anyloid pathology. JAMA 2011 January; 305(3):275-283.

Delacourte A, Sergeant N, Champain D, et al. Nonoverlapping but synergetic tau and APP pathologies in sporadic Alzheimer's disease. Neurology. 2002; 59(3):398-407.

Dubois B, Feldman H H, Jacova C, et al. Revising the definition of Alzheimer's disease: a new lexicon. Lancet Neurol. 2010; 9(11):1118-27.

Jack C R, Knopman D S, Jagust W J, et al. Hypothetical model of dynamic biomarkers of the Alzheimer's pathological cascade. Lancet Neurol. 2010; 9(1):119-28.

Goos J D, Henneman W J, Sluimer J D, Vrenken H, Shoimer I C, Barkhof F, et al. Incidence of cerebral microbleeds: a longitudinal study in a memory clinic population. Neurology. 2010 Jun. 15; 74(24):1954-60. [PubMed]

Gregory G C, Halliday G M. What is the dominant Abeta species in human brain tissue? A review. Neurotox Res. 2005; 7(1-2):29-41.

Hampel H, Shen Y, Walsh D M et al. Biological markers of amyloid beta-related mechanisms in Alzheimer's disease. Exp Neurol 2010 June; 223(2):334-46.

Hardy J, Selkoe D J. The amyloid hypothesis of Alzheimer's disease: progress and problems on the road to therapeutics. Science 2002 Jul. 19; 297(5580):353-6.

Hock C, Konietzko U, Streffer J R, et al. Antibodies against beta-amyloid slow cognitive decline in Alzheimer's disease. Neuron. 2003; 38(4):547-54.

Kumar-Singh S, Pirici D, McGowan E et al. Dense-core plaques in Tg2576 and PSAPP mouse models of Alzheimer's disease are centered on vessel walls. American Journal of Pathology 2005 August; 167(2):527-43.

Landau S M, Harvey D, Madison C M, et al. Associations between cognitive, functional, and FDG-PET measures of decline in AD and MCI. Neurobiol Aging. 2011 July; 32(7):1207-18.

McKhann G M, V. diagnosis of dementia due to Alzheimer's disease: Recommendations from the National Inst. on Aging-Alzheimer's Association workgroups on diagnostic guidelines for Alzheimer's disease. Alzheimer's & Dementia 7 (2011) 263-269.

McShane R, Areosa Sastre A, Minakaran N. Memantine for dementia. Cochrane Database Syst Rev. 2006(2): CD003154.

Meyer-Luehmann M, Mielke M, Spires-Jones T L et al. A reporter of local dendritic translocation shows plaque-related loss of neural system function in APP-transgenic mice. J Neurosci 2009 Oct. 7; 29(40):12636-40.

Mielke R, Pietrzyk U, Jacobs A, et al. HMPAO SPET and FDG PET in Alzheimer's disease and vascular dementia: comparison of perfusion and metabolic pattern. Eur J Nucl Med. 1994 October; 21(10):1052-60.

Nakata-Kudo Y, Mizuno T, Yamada K, Shiga K, Yoshikawa K, Mori S, et al. Microbleeds in Alzheimer disease are more related to cerebral amyloid angiopathy than cerebrovascular disease. Dement Geriatr Cogn Disord. 2006; 22(1):8-14. [PubMed]

Nelson P T, Abner E L, Schmitt F A et al. Brains with medial temporal lobe neurofibrillary tangles but no neuritic amyloid plaques are a diagnostic dilemma but may have pathogenetic aspects distinct from Alzheimer disease. J Neuropathol Exp Neurol 2009 July; 68(7):774-84.

Pfeifer M, Boncristiano S, Bondolfi L et al. Cerebral hemorrhage after passive anti-Abeta immunotherapy. Science 2002 Nov. 15; 298(5597):1379.

Racke M M, Boone L I, Hepburn D L et al. Exacerbation of cerebral amyloid angiopathy-associated microhemorrhage in amyloid precursor protein transgenic mice by immunotherapy is dependent on antibody recognition of deposited forms of amyloid beta. J Neurosci 2005 Jan. 19; 25(3):629-36.

Salloway S, Sperling R, Gilman S, Fox N C, Blennow K, Raskind M, et al. A phase 2 multiple ascending dose trial of bapineuzumab in mild to moderate Alzheimer disease. Neurology. 2009 Nov. 18; [PMC free article] [PubMed]

Selkoe D J. Resolving controversies on the path to Alzheimer's therapeutics. Nat Med. 2011; 17(9):1060-5.

Siemers E, Friedrich S, Dean R, Sethuraman G, Demattos R, Jennings D, et al. Safety, tolerability and biomarker effects of an Aβ monoclonal antibody administered to patients with Alzheimer's disease. Alzheimer's and Dementia. 2008; 4(Suppl 2):T774.

Sperling R, Salloway S, Fox N, Barackos J, Morris K, Francis G, et al., editors. Risk Factors and Clinical Course Associated with Vasogenic Edema in a Phase II Trial of Bapineuzumab. American Academy of Neurology; Seattle, Wash.: 2009.

Sperling R A, Jack Jr C R, Black S E, et al. Amyloid-related imaging abnormalities in amyloid-modifying therapeutic trials: Recommendations from the Alzheimer's Association Research Roundtable Workgroup. Alzheimer's and Dementia. 2011; 7(4):367-85.

Sperling R, Salloway S, Brooks D J, et al. Amyloid-related imaging abnormalities in patients with Alzheimer's disease treated with bapineuzumab: a retrospective analysis. Lancet Neurol. 2012; 11(3):241-9.

Wilcock O M, Colton C A. Immunotherapy, vascular pathology, and microhemorrhages in transgenic mice. CNS & neurological disorders drug targets 2009 March; 8(1):50-64.

Winkler D T, Bondolfi L, Herzig M C et al. Spontaneous hemorrhagic stroke in a mouse model of cerebral amyloid angiopathy. J Neurosci 2001 Mar. 1; 21(5):1619-27.

Sevigny J. et al. Presented at: 13$^{th}$ International Geneva/Springfield Symposium on Advances in Alzheimer Therapy, March 26-29, 2-14, Geneva Switzerland Ostrowitzki S., et al. *Arch Neurol.* 2012; 69:198-207.

Landau S M, et al. *J. Nucl Med.* 2013; 540-77

---

What is claimed is:

1. A method for treating Alzheimer's disease in a human patient in need thereof, comprising:
sequentially administering multiple doses of a recombinant, fully human, anti-amyloid beta monoclonal antibody in increasing amounts over a period of time to the human patient, wherein multiple doses of 1 mg antibody/kg of body weight of the human patient are administered to the human patient at intervals of about 4 weeks, multiple doses of 3 mg antibody/kg of body weight of the human patient are administered to the human patient at intervals of about 4 weeks, multiple doses of 6 mg antibody/kg of body weight of the human patient are administered to the human patient at intervals of about 4 weeks, and multiple doses of 10 mg antibody/kg of body weight of the human patient are administered to the human patient at intervals of about 4 weeks, wherein the antibody comprises a heavy chain variable region (VH) and a light chain variable region (VL), wherein the VH comprises a complementarity determining region1 (VHCDR1) with the amino acid sequence set forth in SEQ ID NO:3, a VHCDR2 with the amino acid sequence set forth in SEQ ID NO:4, and a VHCDR3 with the amino acid sequence set forth in SEQ ID NO:5, and wherein the VL comprises a VLCDR1 with the amino acid sequence set forth in SEQ ID NO:6, a VLCDR2 with the amino acid sequence set forth in SEQ ID NO:7, and a VLCDR3 with the amino acid sequence set forth in SEQ ID NO:8.

2. The method of claim 1, wherein:
the VH comprises the amino acid sequence set forth in SEQ ID NO:1, and
the VL comprises the amino acid sequence set forth in SEQ ID NO:2.

3. The method of claim 2, wherein administration is performed intravenously.

4. The method of claim 2, wherein the human patient has mild Alzheimer's disease.

5. The method of claim 2, wherein the human patient has prodromal Alzheimer's disease.

6. The method of claim 2, wherein the human patient has confirmed amyloid pathology.

7. The method of claim 2, wherein the antibody comprises a human IgG1 constant region.

8. The method of claim 7, wherein the human patient has mild Alzheimer's disease.

9. The method of claim 7, wherein the human patient has prodromal Alzheimer's disease.

10. The method of claim 7, wherein the human patient has confirmed amyloid pathology.

11. The method of claim 7, wherein administration is performed intravenously.

12. The method of claim 1, further comprising administering the antibody to the human patient in four week intervals indefinitely in an amount of 10 mg antibody/kg of body weight of the human patient.

13. The method of claim 12, wherein the VH comprises the amino acid sequence set forth in SEQ ID NO:1, and the VL comprises the amino acid sequence set forth in SEQ ID NO:2.

14. The method of claim 13, wherein the antibody comprises a human IgG1 constant region.

15. The method of claim 1, wherein the human patient has mild Alzheimer's disease.

16. The method of claim 1, wherein the human patient has prodromal Alzheimer's disease.

17. The method of claim 1, wherein the human patient has confirmed amyloid pathology.

18. The method of claim 17, wherein amyloid pathology is confirmed by positron emission tomography (PET) beta-amyloid imaging.

19. The method of claim 1, wherein administration is performed intravenously.

20. The method of claim 1, comprising detecting a biomarker selected from the group consisting of pyroglutamate-Aβ, Aβ40, and Aβ42 in blood of the human patient.

21. The method of claim 1, comprising detecting a biomarker selected from the group consisting of total Tau, phospho-Tau, pyroglutamate-Aβ Aβ40, and Aβ42 in cerebrospinal fluid of the human patient.

22. A method for treating Alzheimer's disease in a human patient in need thereof, comprising:
(A) administering a first dose of a recombinant, fully human anti-amyloid beta monoclonal antibody to the human patient in an amount of 1 mg antibody/kg of body weight of the human patient, followed by a second dose in an amount of 1 mg antibody/kg of body weight of the human patient four weeks after the first dose;
(B) in four week intervals after the second dose, administering doses 3 and 4 to the human patient in an amount of 3 mg antibody/kg of body weight of the human patient; and
(C) in four week intervals after administration of dose 4, administering doses 5 and 6 of the antibody to the human patient in an amount of 6 mg antibody/kg of body weight of the human patient; and
(D) four weeks after administration of dose 6, administering dose 7 of the antibody to the human patient in an amount of 10 mg antibody/kg of body weight of the human patient,
wherein the antibody comprises a VH and a VL, wherein the VH comprises a VHCDR1 with the amino acid sequence set forth in SEQ ID NO:3, a VHCDR2 with the amino acid sequence set forth in SEQ ID NO:4, and a VHCDR3 with the amino acid sequence set forth in SEQ ID NO:5, and wherein the VL comprises a VLCDR1 with the amino acid sequence set forth in SEQ ID NO:6, a VLCDR2 with the amino acid sequence set forth in SEQ ID NO:7, and a VLCDR3 with the amino acid sequence set forth in SEQ ID NO:8.

23. The method of claim 22, further comprising, in four week intervals after dose 7, administering doses 8-14 of the antibody to the human patient in an amount of 10 mg antibody/kg of body weight of the human patient.

24. The method of claim 22, wherein the VH comprises the amino acid sequence set forth in SEQ ID NO:1, and the VL comprises the amino acid sequence set forth in SEQ ID NO:2.

25. The method of claim 24, wherein administration is performed intravenously.

26. The method of claim 24, wherein the human patient has mild Alzheimer's disease.

27. The method of claim 24, wherein the human patient has prodromal Alzheimer's disease.

28. The method of claim 24, wherein the human patient has confirmed amyloid pathology.

29. The method of claim 24, wherein the antibody comprises a human IgG1 constant region.

30. The method of claim 29, wherein the human patient has mild Alzheimer's disease.

31. The method of claim 29, wherein the human patient has prodromal Alzheimer's disease.

32. The method of claim 29, wherein the human patient has confirmed amyloid pathology.

33. The method of claim 29, wherein administration is performed intravenously.

34. The method of claim 22, further comprising, in four week intervals after dose 7, administering doses 8-20 of the antibody to the human patient in an amount of 10 mg antibody/kg of body weight of the human patient.

35. The method of claim 34, wherein the VH comprises the amino acid sequence set forth in SEQ ID NO:1, and the VL comprises the amino acid sequence set forth in SEQ ID NO:2.

36. The method of claim 35, wherein the antibody comprises a human IgG1 constant region.

37. The method of claim 36, wherein the human patient has mild Alzheimer's disease.

38. The method of claim 36, wherein the human patient has prodromal Alzheimer's disease.

39. The method of claim 36, wherein the human patient has confirmed amyloid pathology.

40. The method of claim 36, wherein administration is performed intravenously.

41. The method of claim 22, further comprising, in four week intervals after dose 7, administering the antibody to the human patient indefinitely in an amount of 10 mg antibody/kg of body weight of the human patient.

42. The method of claim 41, wherein the VH comprises the amino acid sequence set forth in SEQ ID NO:1, and the VL comprises the amino acid sequence set forth in SEQ ID NO:2.

43. The method of claim 42, wherein the antibody comprises a human IgG1 constant region.

44. The method of claim 22, wherein the human patient has mild Alzheimer's disease.

45. The method of claim 22, wherein the human patient has prodromal Alzheimer's disease.

46. The method of claim 22, wherein the human patient has confirmed amyloid pathology.

47. The method of claim 22, wherein administration is performed intravenously.

48. A method for treating Alzheimer's disease in a human patient in need thereof, comprising:
  (A) administering a first dose of a recombinant, fully human anti-amyloid beta monoclonal antibody to the human patient in an amount of 1 mg antibody/kg of body weight of the human patient, followed by a second dose in an amount of 1 mg antibody/kg of body weight of the human patient four weeks after the first dose;
  (B) in four week intervals after the second dose, administering doses 3, 4, 5, and 6 of the antibody to the human patient in an amount of 3 mg antibody/kg of body weight of the human patient; and
  (C) in four week intervals after administration of dose 6, administering doses 7, 8, 9, 10, and 11 of the antibody to the human patient in an amount of 6 mg antibody/kg of body weight of the human patient; and
  (D) four weeks after administration of dose 11, administering dose 12 of the antibody to the human patient in an amount of 10 mg antibody/kg of body weight of the human patient,
  wherein the antibody comprises a VH and a VL, wherein the VH comprises a VHCDR1 with the amino acid sequence set forth in SEQ ID NO:3, a VHCDR2 with the amino acid sequence set forth in SEQ ID NO:4, and a VHCDR3 with the amino acid sequence set forth in SEQ ID NO:5, and wherein the VL comprises a VLCDR1 with the amino acid sequence set forth in SEQ ID NO:6, a VLCDR2 with the amino acid sequence set forth in SEQ ID NO:7, and a VLCDR3 with the amino acid sequence set forth in SEQ ID NO:8.

49. The method of claim 48, further comprising, in four week intervals after dose 12, administering dose 13 and dose 14 of the antibody to the human patient in an amount of 10 mg antibody/kg of body weight of the human patient.

50. The method of claim 48, further comprising, in four week intervals after dose 12, administering doses 13-20 of the antibody to the human patient in an amount of 10 mg antibody/kg of body weight of the human patient.

51. The method of claim 50, wherein the VH comprises the amino acid sequence set forth in SEQ ID NO:1, and the VL comprises the amino acid sequence set forth in SEQ ID NO:2.

52. The method of claim 48, further comprising, in four week intervals after dose 12, administering the antibody to the human patient indefinitely in an amount of 10 mg antibody/kg of body weight of the human patient.

53. The method of claim 52, wherein the VH comprises the amino acid sequence set forth in SEQ ID NO:1, and the VL comprises the amino acid sequence set forth in SEQ ID NO:2.

54. The method of claim 48, wherein the VH comprises the amino acid sequence set forth in SEQ ID NO:1, and the VL comprises the amino acid sequence set forth in SEQ ID NO:2.

55. The method of claim 54, wherein the human patient has mild Alzheimer's disease.

56. The method of claim 54, wherein the human patient has prodromal Alzheimer's disease.

57. The method of claim 54, wherein the human patient has confirmed amyloid pathology.

58. The method of claim 54, wherein administration is performed intravenously.

59. The method of claim 54, wherein the antibody comprises a human IgG1 constant region.

60. The method of claim 48, wherein the human patient has mild Alzheimer's disease.

61. The method of claim 48, wherein the human patient has prodromal Alzheimer's disease.

62. The method of claim 48, wherein the human patient has confirmed amyloid pathology.

63. The method of claim 48, wherein administration is performed intravenously.

* * * * *

UNITED STATES PATENT AND TRADEMARK OFFICE
CERTIFICATE OF CORRECTION

Page 1 of 1

PATENT NO. : 10,842,871 B2
APPLICATION NO. : 15/531960
DATED : November 24, 2020
INVENTOR(S) : James L. Ferrero, Leslie Lugene Williams and Jeffrey Joseph Sevigny It is certified that error appears in the above-identified patent and that said Letters Patent is hereby corrected as shown below:

In the Claims

Column 36
Claim 21, Line 3, delete "-Aβ" and insert -- -Aβ, -- therefor.

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 8

<210> SEQ ID NO 1
<211> LENGTH: 124
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Thr Ala Val Tyr Tyr Cys
                 85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
            100                 105

<210> SEQ ID NO 3
<211> LENGTH: 5
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(5)
<223> OTHER INFORMATION: Denomination of CDR protein sequences in Kabat
      Nomenclature of NI-101.11 and NI-101.12F6A Vh, CDR1

<400> SEQUENCE: 3

Ser Tyr Gly Met His
 1               5

<210> SEQ ID NO 4
<211> LENGTH: 17
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(17)
<223> OTHER INFORMATION: Denomination of CDR protein sequences in Kabat
      Nomenclature of NI-101.11 and NI-101.12F6A Vh, CDR2

<400> SEQUENCE: 4

Val Ile Trp Phe Asp Gly Thr Lys Lys Tyr Tyr Thr Asp Ser Val Lys
 1               5                  10                  15

Gly
```

```
<210> SEQ ID NO 5
<211> LENGTH: 15
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(15)
<223> OTHER INFORMATION: Denomination of CDR protein sequences in Kabat
      Nomenclature of NI-101.11and NI-101.12F6A Vh, CDR3

<400> SEQUENCE: 5

Asp Arg Gly Ile Gly Ala Arg Arg Gly Pro Tyr Tyr Met Asp Val
1               5                   10                  15

<210> SEQ ID NO 6
<211> LENGTH: 11
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.10, NI-101.11 and NI-101.12F6A Vkappa, CDR1

<400> SEQUENCE: 6

Arg Ala Ser Gln Ser Ile Ser Ser Tyr Leu Asn
1               5                   10

<210> SEQ ID NO 7
<211> LENGTH: 7
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.10, NI-101.11 and NI-101.12F6A Vkappa, CDR2

<400> SEQUENCE: 7

Ala Ala Ser Ser Leu Gln Ser
1               5

<210> SEQ ID NO 8
<211> LENGTH: 9
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of NI-101.10, NI-101.11 and NI-101.12F6A Vkappa, CDR3

<400> SEQUENCE: 8

Gln Gln Ser Tyr Ser Thr Pro Leu Thr
1               5
```